United States Patent
Seehra et al.

(10) Patent No.: US 6,500,853 B1
(45) Date of Patent: Dec. 31, 2002

(54) INHIBITORS OF PHOSPHOLIPASE ENZYMES

(75) Inventors: Jasbir S. Seehra, Lexington, MA (US); John C. McKew, Arlington, MA (US); Frank Lovering, Acton, MA (US); Jean E. Bemis, Arlington, MA (US); YiBin Xiang, Acton, MA (US); Lihren Chen, Cambridge, MA (US); John L. Knopf, Acton, MA (US)

(73) Assignee: Genetics Institute, LLC, Cambridge, MA (US)

( * ) Notice: Subject to any disclaimer, the term of this patent is extended or adjusted under 35 U.S.C. 154(b) by 48 days.

(21) Appl. No.: 09/686,616

(22) Filed: Oct. 11, 2000

Related U.S. Application Data

(63) Continuation-in-part of application No. 09/256,062, filed on Feb. 24, 1999, now abandoned.
(60) Provisional application No. 60/113,674, filed on Feb. 28, 1998.

(51) Int. Cl.$^7$ .................. A61K 31/405; C07D 209/210
(52) U.S. Cl. ..................... 514/415; 548/509; 548/250; 514/339; 514/381; 546/277.4
(58) Field of Search ................. 514/415, 339, 514/381; 548/509, 250; 546/277.4

(56) References Cited

U.S. PATENT DOCUMENTS

| | | |
|---|---|---|
| 3,271,416 A | 9/1966 | Shen et al. |
| 3,629,284 A | 12/1971 | Yamamoto et al. |
| 3,669,987 A | 6/1972 | Sato et al. |
| 3,884,919 A | 5/1975 | Birchall et al. |
| 4,192,880 A | 3/1980 | Tsukamato et al. |
| 4,235,871 A | 11/1980 | Papahadjopoulos et al. |
| 4,271,263 A | 6/1981 | Goettert et al. |
| 4,501,728 A | 2/1985 | Geho et al. |
| 4,654,360 A | 3/1987 | Greenhouse et al. |
| 4,734,421 A | 3/1988 | Hammond et al. |
| 4,737,323 A | 4/1988 | Martin et al. |
| 4,772,703 A | 9/1988 | Musser et al. |
| 4,837,028 A | 6/1989 | Allen et al. |
| 4,894,386 A | 1/1990 | Brown et al. |
| 4,920,140 A | 4/1990 | Shroot et al. |
| 4,957,932 A | 9/1990 | Young et al. |
| 5,084,575 A | 1/1992 | Kreft et al. |
| 5,141,950 A | 8/1992 | Nakane et al. |
| 5,166,170 A | 11/1992 | Tegeler et al. |
| 5,212,195 A | 5/1993 | Clark et al. |
| 5,218,124 A | 6/1993 | Failli et al. |
| 5,250,565 A | 10/1993 | Brooks et al. |
| 5,288,743 A | 2/1994 | Brooks et al. |
| 5,314,880 A | 5/1994 | Whittaker et al. |
| 5,319,097 A | 6/1994 | Holohan et al. |
| 5,322,776 A | 6/1994 | Knofp et al. |
| 5,332,755 A | 7/1994 | Butler et al. |
| 5,354,677 A | 10/1994 | Knopf et al. |
| 5,391,758 A | 2/1995 | Bernstein et al. |
| 5,420,289 A | 5/1995 | Musser et al. |
| 5,424,329 A | 6/1995 | Boschelli et al. |
| 5,434,150 A | 7/1995 | Austel et al. |
| 5,446,059 A | 8/1995 | Rocher et al. |
| 5,459,152 A | 10/1995 | Summers et al. |
| 5,482,960 A | 1/1996 | Berryman et al. |
| 5,482,963 A | 1/1996 | Holohan et al. |
| 5,486,525 A | 1/1996 | Summers et al. |
| 5,504,216 A | 4/1996 | Holohan et al. |
| 5,567,711 A | 10/1996 | Sheppard et al. |
| 5,578,634 A | 11/1996 | Bach et al. |
| 5,599,930 A | 2/1997 | Romero et al. |
| 5,654,305 A | 8/1997 | Sheppard et al. |
| 5,654,326 A | 8/1997 | Bach et al. |
| 5,684,034 A | 11/1997 | Bach et al. |
| 5,741,804 A | 4/1998 | Keenan et al. |

FOREIGN PATENT DOCUMENTS

| | | |
|---|---|---|
| CH | 484111 | 1/1970 |
| EP | 0337766 | 10/1989 |
| EP | 0337767 | 10/1989 |
| FR | 2152377 | 4/1973 |
| JP | 46038784 | 11/1971 |
| WO | 9106537 | 5/1991 |
| WO | 9203132 | 3/1992 |
| WO | 9513266 | 5/1995 |
| WO | 9637467 | 11/1996 |
| WO | 9637469 | 11/1996 |
| WO | 9713751 | 4/1997 |
| WO | 9808818 | 3/1998 |

OTHER PUBLICATIONS

Smith, W. *Biochem. J.* 1989, 259, 315.
Wasserman, S. *Hospital Practice* 1988, 49.
Chang, J. et al. *Biochemical Pharmacology* 1987, 36, 2429.
Dennis, E. *Drug Development Research* 2987, 10, 205.
Seilhamer, J. et al. *J. Bio. Chem.* 1989, 10, 5335.
Kramer, R. et al. *J. Bio. Chem.* 1989, 10, 5768.

(List continued on next page.)

*Primary Examiner*—Ceila Chang
*Assistant Examiner*—Sonya Wright
(74) *Attorney, Agent, or Firm*—Joseph M. Mazzarese

(57) ABSTRACT

This invention concerns compounds and pharmaceutical compositions useful for treating or preventing inflammatory conditions in a mammal, the methods comprising administration of novel pharmaceutically useful compounds of the general formulae:

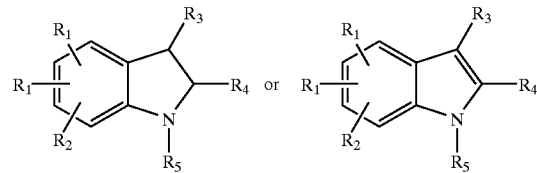

or pharmaceutically acceptable salts thereof, wherein $R_1$–$R_5$ are as defined in the specification.

19 Claims, No Drawings

OTHER PUBLICATIONS

Kanda, A. et al. *Biochem. and Biophys. Research Comm.* 1989, 163, 42.
Burch, R. et al. *Proc. Natl. Acad. Sci. USA* 1987, 84, 6374.
Leslie, C. et al. *Bioch. et Biophys. Acta* 1988, 963, 476.
Bligh, E. et al. *Can. J. Biochem. Physiol.* 1959, 37, 911.
Kutkevicius, S. et al. *Chem. Abstract* 1982, 96: 85391.
Gadient et al. *Chem. Abstract* 1980, 93: 71555.
Griffin, R. et al. *Chem. Abstract* 1997, 126: 212151.
Yamaguchi *Chem. Abstract* 1996, 124: 329940b.
Geban et al. *Chem. Abstract* 1996, 124: 219398y.
Aldrich Catalogue, 1994, pp. 1116.
Cox et al. *Chem. Abstract* 1988, 108:94553.
Rao et al., *Chem. Abstract* l1980, 93: 167168t.
Inoue et al. *Chem. Abstract* 1975, 82: 16840.
Kuranari et al. *Chem. Abstract* 1968, 68: 29698y.
Aka et al. *Chem. Abstract* 1967, 66: 95044s.
Samuelsson et al. *Science* 1987, 1237, 1171.
Ramesha, C. et al. *Anal. Biochem.* 1991, 192, 173.
Chen et al., *Chem. Abstracts,* 1994, 121: 124872.
Yamamoto et al., *Chem. Abstracts,* 1972, 76: 25103.
Dillard et al., *J. Med. Chem.,* 1996, 39, 5137–5158.

INHIBITORS OF PHOSPHOLIPASE ENZYMES

This application is a continuation-in-part of U.S. Ser. No. 09/256,062, filed Feb. 24, 1999, now abandoned which claims the benefit of U.S. Provisional Application No. 60/113,674, which was converted from U.S. patent application Ser. No. 09/030,592, filed Feb. 28, 1998, pursuant to a petition filed under 37 C.F.R. 1.53(c)(2)(i).

BACKGROUND OF THE INVENTION

The present invention relates to chemical inhibitors of the activity of various phospholipase enzymes, particularly phospholipase $A_2$ enzymes.

Leukotrienes and prostaglandins are important mediators of inflammation, each of which classes contributes to the development of an inflammatory response in a different way. Leukotrienes recruit inflammatory cells such as neutrophils to an inflamed site, promote the extravasation of these cells and stimulate release of superoxide and proteases which damage the tissue. Leukotrienes also play a pathophysiological role in the hypersensitivity experienced by asthmatics [See, e.g. B. Samuelson et al., *Science*, 237:1171–76 (1987)]. Prostaglandins enhance inflammation by increasing blood flow and therefore infiltration of leukocytes to inflamed sites. Prostaglandins also potentiate the pain response induced by stimuli.

Prostaglandins and leukotrienes are unstable and are not stored in cells, but are instead synthesized [W. L. Smith, *Biochem. J.*, 259:315–324 (1989)] from arachidonic acid in response to stimuli. Prostaglandins are produced from arachidonic acid by the action of COX-1 and COX-2 enzymes. Arachidonic acid is also the substrate for the distinct enzyme pathway leading to the production of leukotrienes.

Arachidonic acid which is fed into these two distinct inflammatory pathways is released from the sn-2 position of membrane phospholipids by phospholipase $A_2$ enzymes (hereinafter $PLA_2$). The reaction catalyzed by $PLA_2$ is believed to represent the rate-limiting step in the process of lipid mediated biosynthesis and the production of inflammatory prostaglandins and leukotrienes. When the phospholipid substrate of $PLA_2$ is of the phosphotidyl choline class with an ether linkage in the sn-1 position, the lysophospholipid produced is the immediate precursor of platelet activating factor (hereafter called PAF), another potent mediator of inflammation [S. I. Wasserman, Hospital Practice, 15:49–58 (1988)].

Most anti-inflammatory therapies have focussed on preventing production of either prostglandins or leukotrienes from these distinct pathways, but not on all of them. For example, ibuprofen, aspirin, and indomethacin are all NSAIDs which inhibit the production of prostaglandins by COX-1/COX-2, but have no effect on the inflammatory production of leukotrienes from arachidonic acid in the other pathways. Conversely, zileuton inhibits only the pathway of conversion of arachidonic acid to leukotriense, without affecting the production of prostaglandins. None of these widely-used anti-inflammatory agents affects the production of PAF.

Consequently the direct inhibition of the activity of $PLA_2$ has been suggested as a useful mechanism for a therapeutic agent, i.e., to interfere with the inflammatory response. [See, e.g., J. Chang et al, *Biochem. Pharmacol.*, 36:2429–2436 (1987)].

A family of $PLA_2$ enzymes characterized by the presence of a secretion signal sequenced and ultimately secreted from the cell have been sequenced and structurally defined. These secreted $PLA_2$s have an approximately 14 kD molecular weight and contain seven disulfide bonds which are necessary for activity. These $PLA_2$s are found in large quantities in mammalian pancreas, bee venom, and various snake venom. [See, e.g., references 13–15 in Chang et al, cited above; and E. A. Dennis, *Drug Devel. Res.*, 10:205–220 (1987).] However, the pancreatic enzyme is believed to serve a digestive function and, as such, should not be important in the production of the inflammatory mediators whose production must be tightly regulated.

The primary structure of the first human non-pancreatic $PLA_2$ has been determined. This non-pancreatic $PLA_2$ is found in platelets, synovial fluid, and spleen and is also a secreted enzyme. This enzyme is a member of the aforementioned family. [See, J. J. Seilhamer et al, *J. Biol. Chem.*, 264:5335–5338 (1989); R. M. Kramer et al, *J. Biol. Chem.*, 264:5768–5775 (1989); and A. Kando et al, *Biochem. Biophys. Res. Comm.*, 163:42–48 (1989)]. However, it is doubtful that this enzyme is important in the synthesis of prostaglandins, leukotrienes and PAF, since the non-pancreatic $PLA_2$ is an extracellular protein which would be difficult to regulate, and the next enzymes in the biosynthetic pathways for these compounds are intracellular proteins. Moreover, there is evidence that $PLA_2$ is regulated by protein kinase C and G proteins [R. Burch and J. Axelrod, *Proc. Natl. Acad. Sci. U.S.A.*, 84:6374–6378 (1989)] which are cytosolic proteins which must act on intracellular proteins. It would be impossible for the non-pancreatic $PLA_2$ to function in the cytosol, since the high reduction potential would reduce the disulfide bonds and inactivate the enzyme.

A murine $PLA_2$ has been identified in the murine macrophage cell line, designated RAW 264.7. A specific activity of 2 mols/min/mg, resistant to reducing conditions, was reported to be associated with the approximately 60 kD molecule. However, this protein was not purified to homogeneity. [See, C. C. Leslie et al, *Biochem. Biophys. Acta.*, 963:476–492 (1988)]. The references cited above are incorporated by reference herein for information pertaining to the function of the phospholipase enzymes, particularly $PLA_2$.

A cytosolic phospholipase $A_2$ (hereinafter "$cPLA_2$") has also been identified and cloned. See, U.S. Pat. Nos. 5,322,776 and 5,354,677, which are incorporated herein by reference as if fully set forth. The enzyme of these patents is an intracellular $PLA_2$ enzyme, purified from its natural source or otherwise produced in purified form, which functions intracellularly to produce arachidonic acid in response to inflammatory stimuli.

It is now desirable to identify pharmaceutically useful compounds which inhibit the actions of these phospholipase enzymes for use in treating or preventing inflammatory conditions, particularly where inhibition of production of prostaglandins, leukotrienes and PAF are all desired results. There remains a need in the art for an identification of such anti-inflammatory agents for therapeutic use in a variety of disease states.

Numerous pieces of evidence have supported the central role of $cPLA_2$ in lipid mediator biosynthesis: $cPLA_2$ is the only enzyme which is highly selective for phospholipids containing arachidonic acid in the sn-2 position (Clark et al., 1991, 1995; Hanel & Gelb, 1993); activation of $cPLA_2$ or its increased expression have been linked with increased leukotriene and prostaglandin synthesis (Lin et al., 1992a, 1992b, 1993); and following activation, $cPLA_2$ translocates to the nuclear membrane, where it is co-localized with the cyclooxygenase and lipoxygenase that metabolize arachidonate to prostaglandins and leukotrienes (Schievella et al., 1995; Glover et al., 1995). Although these data are compelling, the most definitive evidence for the central role of cPLA$_2$ in eicosanoid and PAF production came from mice made deficient in cPLA$_2$ through homologous recombination (Uozumi et al., 1997; Bonventre et al., 1997). Peritoneal macrophages derived from these animals failed to make leukotrienes, prostaglandins, or PAF. The cPLA$_2$ deficient mice have also been informative of the role of cPLA$_2$ in disease, since these mice are resistant to bronchial hyperreactivity in an anaphylaxis model used to mimic asthma (Uozumi et al., 1997). Thus, despite the size of the phospholipase A$_2$ superfamily, cPLA$_2$ is essential for prostaglandin, leukotriene, and PAF production.

Clark, J. D., Lin, L.-L., Kriz, R. W., Ramesha, C. S., Sultzman, L. A., Lin, A. Y., Milona, N., and Knopf, J. L. (1991). A novel arachidonic acid-selective cytosolic PLA$_2$ contains a Ca$^{2+}$-dependent translocation domain with homology to PKC and GAP. Cell 65,1043–1051. Hanel, A. M., and Gelb, M. H. (1993). Processive interfacial catalysis by mammalian 85-kilodalton phospholipase A$_2$ enzymes on product-containing vesicles: application to the determination of substrate preferences. Biochemistry 32, 5949–5958.

Lin, L.-L., Lin, A. Y., and DeWitt, D. L. (1992a) IL-1 induces the accumulation of cPLA2 and the release of PGE$_2$ in human fibroblasts. J. Biol. Chem. 267, 23451–23454. Lin, L.-L., Lin, A. Y., and Knopf, J. L. (1992b) Cytosolic phospholipase A$_2$ is coupled to hormonally regulated release of arachidonic acid. Proc. Natl. Acad. Sci. USA 89, 6147–6151. Lin, L.-L., Wartmann, M., Lin, A. Y., Knopf, J. L., Seth, A., and Davis, R. J. (1993) cPLA$_2$ is phosphorylated and activated by MAP kinase. Cell 72, 269–278.

Glover, S., de Carvalho, M., Bayburt, T., Jonas, M., Chi, E., Leslie, E., and Gelb, M. (1995) Translocation of the 85-kDa phospholipase A$_2$ from cytosol to the nuclear envelope in rat basophilic leukemia cells stimulated with calcium ionophore or IgE/antigen. J. Biol. Chem. 270, 15359–15367. Schievella, A. R., Regier, M. K., Smith, W. L., and Lin, L.-L. (1995). Calcium-mediated translocation of cytosolic phospholipase A$_2$ to the nuclear envelope and endoplasmic reticulum. J. Biol. Chem. 270, 30749–30754.

Uozumi, N., Kume, K., Nagase, T., Nakatani, N., Ishii, S., Tashiro, F., Komagata, Y., Maki, K., Ikuta, K., Ouchi, Y., Miyazaki, J.-i., & Shimizu, T. (1997). Role of cytosolic phospholipase A$_2$ in allergic response and parturition. Nature 390, 618–622. Bonventre, J. V., Huang, Z., Reza Taheri, M., O'Leary, E., Li, E., Moskowitz, M. A., and Sapirstein, A. (1997) Reduced fertility and postischaeric brain injury in mice deficient in cytosolic phospholipase A$_2$. Nature 390, 622–625.

SUMMARY OF THE INVENTION

Compounds of this invention have the following formulae:

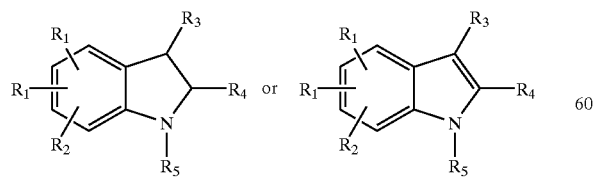

wherein:
R$_1$ and R$_1$, are independently selected from H, halogen, —CF$_3$, —OH, —C$_1$–C$_{10}$ alkyl, preferably —C$_1$–C$_6$ alkyl, —S—C$_1$–C$_{10}$ alkyl, preferably —S—C$_1$–C$_6$ alkyl, C$_1$–C$_{10}$ alkoxy, preferably C$_1$–C$_6$ alkoxy, —CN, —NO$_2$, —NH$_2$, phenyl, —O-phenyl, —S-phenyl, benzyl, —O-benzyl, —S-benzyl; or a ring moiety of the groups a), b) or c), below, directly bonded to the indole ring or bonded to the indole ring by a —S—, —O— or —(CH$_2$)$_n$— bridge;

a) a five-membered heterocyclic ring containing one or two ring heteroatoms selected from N, S or O including, but not limited to, furan, pyrrole, thiophene, imidazole, pyrazole, isothiazole, isoxazole, pyrrolidine, pyrroline, imidazolidine, pyrazolidine, pyrazole, pyrazoline, imidazole, tetrazole, oxathiazole, the five-membered heterocyclic ring being optionally substituted by from 1 to 3 substituents selected from halogen, C$_1$–C$_{10}$ alkyl, preferably C$_1$–C$_6$ alkyl, C$_1$–C$_{10}$ alkoxy, preferably C$_1$–C$_6$ alkoxy, —NO$_2$, —NH$_2$, —CN, —CF$_3$; or b) a six-membered heterocyclic ring containing one, two or three ring heteroatoms selected from N, S or O including, but not limited to, pyran, pyridine, pyrazine, pyrimidine, pyridazine, piperidine, piperazine, tetrazine, thiazine, thiadizine, oxazine, or morpholine, the six-membered heterocyclic ring being optionally substituted by from 1 to 3 substituents selected from halogen, C$_1$–C$_{10}$ alkyl, preferably C$_1$–C$_6$ alkyl, C$_1$–C$_{10}$ alkoxy, preferably C$_1$–C$_6$ alkoxy, —CHO, —NO$_2$, —NH$_2$, —CN, —CF$_3$ or —OH; or c) a bicyclic ring moiety optionally containing from 1 to 3 ring heteroatoms selected from N, S or O including, but not limited to benzofuran, chromene, indole, isoindole, indoline, isoindoline, napthalene, purine, indolizine, indazole, quinoline, isoquinoline, quinolizine, quinazoline, cinnoline, phthalazine, or napthyridine, the bicyclic ring moiety being optionally substituted by from 1 to 3 substituents selected from halogen, C$_1$–C$_{10}$ alkyl, preferably C$_1$–C$_6$ alkyl, C$_1$–C$_{10}$ alkoxy, preferably C$_1$–C$_6$ alkoxy, —CHO, —NO$_2$, —NH$_2$, —CN, —CF$_3$ or —OH; or d) a moiety of the formulae:

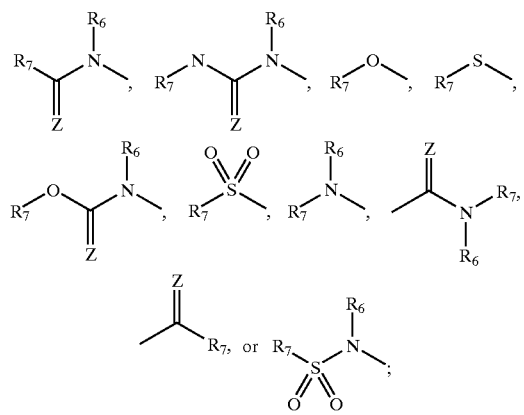

Z is O or S;

R$_6$ is selected from the relevant members of the group H, —CF$_3$, C$_1$–C$_{10}$ alkyl, preferably C$_1$–C$_6$ alkyl, C$_1$–C$_{10}$ alkoxy, preferably C$_1$–C$_6$ alkoxy, phenyl, —O-phenyl, —S-phenyl, benzyl, —O-benzyl, or —S-benzyl, the phenyl and benzyl rings of these groups being optionally substituted by from 1 to 3 substituents selected from halogen, C$_1$–C$_{10}$ alkyl, preferably C$_1$–C$_6$ alkyl, $C_1$–$C_{10}$ alkoxy, preferably $C_1$–$C_6$ alkoxy, —CHO, —$NO_2$, —$NH_2$, —CN, —$CF_3$, or —OH;

$R_7$ is selected from —$(CH_2)_n$—COOH, —$(CH_2)_n$—N—($C_1$–$C_6$ alkyl)$_2$, —$(CH_2)$—NH—($C_1$–$C_6$ alkyl), —$CF_3$, $C_1$–$C_6$ alkyl, $C_3$–$C_5$ cycloalkyl, $C_1$–$C_6$ alkoxy, —NH—($C_1$–$C_6$ alkyl), —N—($C_1$–$C_6$ alkyl)$_2$, pyridinyl, thienyl, furyl, pyrrolyl, quinolyl, $(CH_2)_n$ phenyl, phenyl, —O-phenyl, benzyl, —O-benzyl, adamantyl, or morpholinyl, —$(CH_2)_n$-phenyl-O-phenyl, —$(CH_2)_n$-phenyl-$CH_2$-phenyl, —$(CH_2)_n$-O-phenyl-$CH_2$-phenyl, —$(CH_2)_n$-phenyl-(O—$CH_2$-phenyl)$_2$, the rings of these groups being optionally substituted by from 1 to 3 substituents selected from halogen, $C_1$–$C_6$ alkyl, $C_1$–$C_6$ alkoxy, —$NH_2$, —$NO_2$, —$CF_3$,$CO_2$H, or —OH; or a) a five-membered heterocyclic ring containing one or two ring heteroatoms selected from N, S or O including, but not limited to, furan, pyrrole, thiophene, imidazole, pyrazole, isothiazole, isoxazole, pyrrolidine, pyrroline, imidazolidine, pyrazolidine, pyrazole, pyrazoline, imidazole, tetrazole, oxathiazole, the five-membered heterocyclic ring being optionally substituted by from 1 to 3 substituents selected from halogen, $C_1$–$C_{10}$ alkyl, preferably $C_1$–$C_6$ alkyl, $C_1$–$C_{10}$ alkoxy, preferably $C_1$–$C_6$ alkoxy, —$NO_2$, —$NH_2$, —CN, or —$CF_3$; or b) a six-membered heterocyclic ring containing one, two or three ring heteroatoms selected from N, S or O including, but not limited to, pyran, pyridine, pyrazine, pyrimidine, pyridazine, piperidine, piperazine, tetrazine, thiazine, thiadizine, oxazine, or morpholine, the six-membered heterocyclic ring being optionally substituted by from 1 to 3 substituents selected from halogen, $C_1$–$C_{10}$ alkyl, preferably $C_1$–$C_6$ alkyl, $C_1$–$C_{10}$ alkoxy, preferably $C_1$–$C_6$ alkoxy, —CHO, —$NO_2$, —$NH_2$, —CN, —$CF_3$ or —OH; or c) a bicyclic ring moiety containing from 8 to 10 ring atoms and optionally containing from 1 to 3 ring heteroatoms selected from N, S or O including, but not limited to benzofuran, chromene, indole, isoindole, indoline, isoindoline, napthalene, purine, indolizine, indazole, quinoline, isoquinoline, quinolizine, quinazoline, cinnoline, phthalazine, or napthyridine, the bicyclic ring moiety being optionally substituted by from 1 to 3 substituents selected from halogen, $C_1$–$C_{10}$ alkyl, preferably $C_1$–$C_6$ alkyl, $C_1$–$C_{10}$ alkoxy, preferably $C_1$–$C_6$ alkoxy, —CHO, —$NO_2$, —$NH_2$, —CN, —$CF_3$ or —OH;

n is an integer from 0 to 3;

$R_2$ is selected from H, halogen, —CN, —CHO, —$CF_3$, —OH, $C_1$–$C_{10}$ alkyl, preferably $C_1$–$C_6$ alkyl, $C_1$–$C_{10}$ alkoxy, preferably $C_1$–$C_6$ alkoxy, —CHO, —CN, —$NO_2$, —$NH_2$, —NH—$C_1$–$C_6$ alkyl, —N($C_1$–$C_6$ alkyl)$_2$, —N—$SO_2$—$C_1$–$C_6$ alkyl, or —$SO_2$—$C_1$–$C_6$ alkyl;

$R_3$ is selected from —COOH, —C(O)—COOH, —$(CH_2)_n$—C(O)—COOH, —$(CH_2)_n$—COOH, $(CH_2)_n$—CH=CH—COOH, —$(CH_2)_n$-tetrazole,

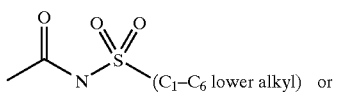

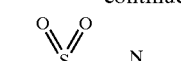

or a moiety selected from the formulae —$L^1$—$M^1$;

wherein $L^1$ is a bridging or linking moiety selected from a chemical bond, —$(CH_2)_n$—, —S—, —O—, —$SO_2$—, —C(O)—, —$(CH_2)_n$—C(O)—, —$(CH_2)_n$—C(O)—$(CH_2)_n$—, —$(CH_2)_n$—O—$(CH_2)_n$—, —C(Z)—N($R_6$)—, —C(Z)—N($R_6$)—$(CH_2)_n$—, —C(O)—C(Z)—N($R_6$)—, —C(O)—C(Z)—N($R_6$)—$(CH_2)_n$—, —C(Z)—NH—$SO_2$—, —C(Z)—NH—$SO_2$—$(CH_2)_n$—, —$(CH_2)_n$—S—$(CH_2)_n$—, —$(CH_2)_n$—SO—$(CH_2)_n$—, —$(CH_2)_n$—$SO_2$—$(CH_2)_n$—, or —$(CH_2)_n$—CH=CH—$(CH_2)_n$—O—;

n is an integer from 0 to 3

$M^1$ is selected from the group of —COOH, —$(CH_2)_n$—COOH, —$(CH_2)_n$—C(O)—COOH, tetrazole,

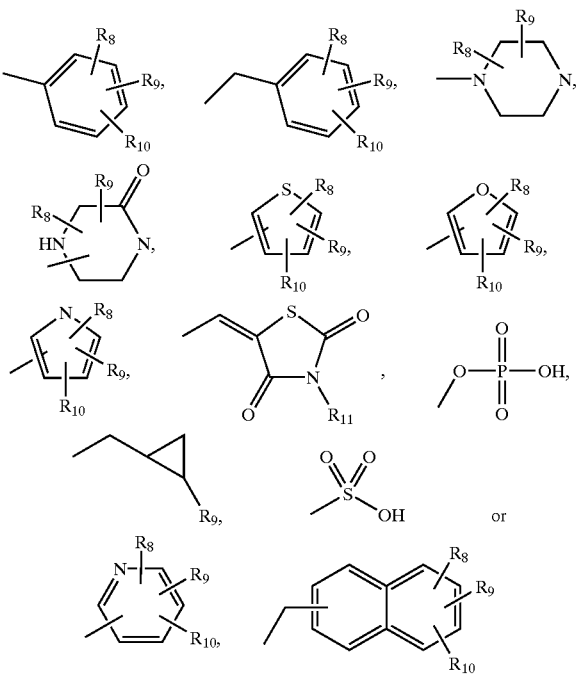

$R_8$, in each appearance, is independently selected from H, —COOH, —$(CH_2)_n$—COOH, —$(CH_2)_n$—C(O)—COOH, tetrazole, —C(O)—$NH_2$, —$(CH_2)_n$—C(O)—$NH_2$,

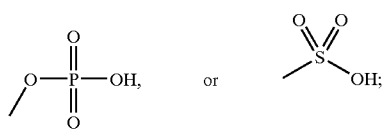

$R_9$ is selected from H, halogen, —$CF_3$, —OH, —COOH, —$(CH_2)_n$—COOH, —$(CH_2)_n$—C(O)—COOH, —$C_1$–$C_6$ alkyl, —O—$C_1$–$C_6$ alkyl, —O—$(CH_2)_n$—COOH, —O—$CH_2$—C=C—COOH, —O—C≡C—$CH_2$—COOH, —NH($C_1$–$C_6$ alkyl), —N($C_1$–$C_6$ alkyl)$_2$, —N—C(O)—$(CH_2)_n$—COOH, —N—$SO_2$—$(CH_2)_n$—COOH, —C(O)—N—$(CH_2)_n$—COOH;

$R_{10}$ is selected from the group of H, halogen, —$CF_3$, —OH, —$(CH_2)_n$—COOH, —$(CH_2)_n$—C(O)—COOH, —$C_1$–$C_6$ alkyl, —O—$C_1$–$C_6$ alkyl, —O—($C_1$–$C_6$ alkyl)—(OH)$_n$, —NH($C_1$–$C_6$ alkyl), —N($C_1$–$C_6$ alkyl)$_2$, —N—C(O)—N—($C_1$–$C_6$ alkyl)-(OH)$_2$,

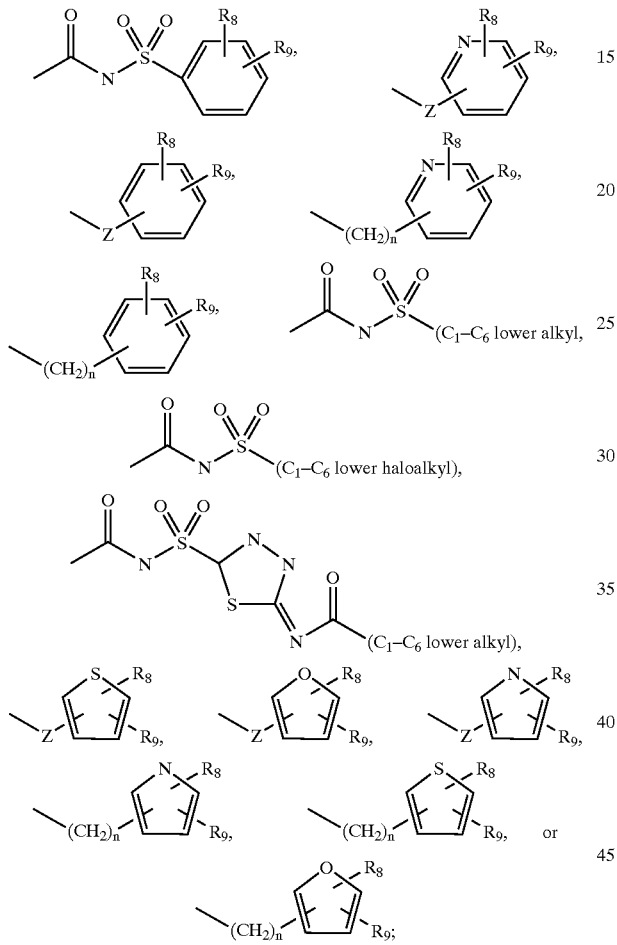

$R_{11}$ is selected from H, $C_1$–$C_6$ lower alkyl, $C_1$–$C_6$ cycloalkyl, —$CF_3$, —COOH, —$(CH_2)_n$—COOH, —$(CH_2)_n$—C(O)—COOH,

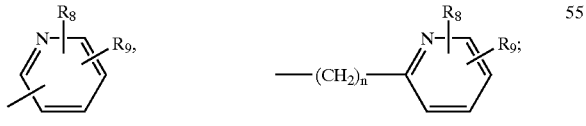

with a proviso that the complete moiety at the indole or indoline 3-position created by any combination of $R_3$, $L^1$, M, $R_8$, $R_9$, $R_{10}$, and/or $R_{11}$ shall contain at least one acidic moiety selected from or containing a carboxylic acid, a tetrazole, or a moiety of the formulae: —C(O)—$NH_2$, —$(CH_2)_n$—C(O)—$NH_2$,

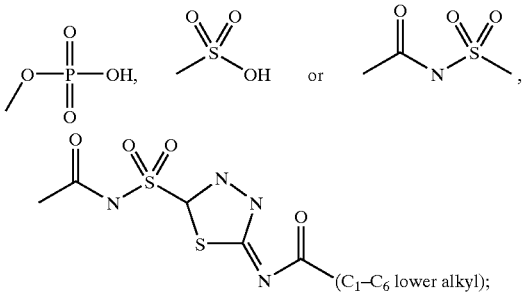

n is an integer from 0 to 3;

$R_4$ is selected from H, —$CF_3$, $C_1$–$C_6$ lower alkyl, $C_1$–$C_6$ lower alkoxy, $C_3$–$C_{10}$ cycloalkyl, —$C_1$–$C_6$ alkyl-$C_3$—$C_{10}$ cycloalkyl, —CHO, halogen, or a moiety of the formula —$L^2$—$M^2$:

$L^2$ indicates a linking or bridging group of the formulae —$(CH_2)_n$—, —S—, —O—, —C(O)—, —$(CH_2)_n$—C(O)—, —$(CH_2)_n$—C(O)—$(CH_2)_n$—, —$(CH_2)_n$—O—$(CH_2)_n$—, or —$(CH_2)_n$—S—$(CH_2)_n$—, C(O)C(O)X, or —$(CH_2)_n$—N—$(CH_2)_n$;

where X is O or N n is an integer from 0 to 3

$M^2$ is selected from:

a) H, the group of $C_1$–$C_6$ lower alkyl, $C_1$–$C_6$ lower alkoxy, $C_3$–$C_{10}$ cycloalkyl, phenyl or benzyl, the cycloalkyl, phenyl or benzyl rings being optionally substituted by from 1 to 3 substituents selected from halogen, $C_1$–$C_{10}$ alkyl, preferably $C_1$–$C_6$ alkyl, $C_1$–$C_{10}$ alkoxy, preferably $C_1$–$C_6$ alkoxy, —$NO_2$, —$NH_2$, —CN, or —$CF_3$; or b) a five-membered heterocyclic ring containing one or two ring heteroatoms selected from N, S or O including, but not limited to, furan, pyrrole, thiophene, imidazole, pyrazole, isothiazole, isoxazole, pyrrolidine, pyrroline, imidazolidine, pyrazolidine, pyrazole, pyrazoline, imidazole, tetrazole, oxathiazole, the five-membered heterocyclic ring being optionally substituted by from 1 to 3 substituents selected from halogen, $C_1$–$C_{10}$ alkyl, preferably $C_1$–$C_6$ alkyl, $C_1$–$C_{10}$ alkoxy, preferably $C_1$–$C_6$ alkoxy, —$NO_2$, —$NH_2$, —CN, or —$CF_3$; or c) a six-membered heterocyclic ring containing one, two or three ring heteroatoms selected from N, S or O including, but not limited to, pyran, pyridine, pyrazine, pyrimidine, pyridazine, piperidine, piperazine, tetrazine, thiazine, thiadizine, oxazine, or morpholine, the six-membered heterocyclic ring being optionally substituted by from 1 to 3 substituents selected from halogen, $C_1$–$C_{10}$ alkyl, preferably $C_1$–$C_6$ alkyl, $C_1$–$C_{10}$ alkoxy, preferably $C_1$–$C_6$ alkoxy, —CHO, —$NO_2$, —$NH_2$, —CN, —$CF_3$ or —OH; or d) a bicyclic ring moiety containing from 8 to 10 ring atoms and optionally containing from 0 to 3 ring heteroatoms selected from N, S or O including, but not limited to benzofuran, chromene, indole, isoindole, indoline, isoindoline, napthalene, purine, indolizine, indazole, quinoline, isoquinoline, quinolizine, quinazoline, cinnoline, phthalazine, or napthyridine, the bicyclic ring moiety being optionally substituted by from 0 to 3 substituents selected from halogen, $C_1$–$C_{10}$ alkyl, preferably $C_1$–$C_6$ alkyl, $C_1$–$C_{10}$ alkoxy, preferably $C_1$–$C_6$ alkoxy, —CHO, —NO$_2$, —NH$_2$, —CN, —CF$_3$ or —OH;

$R_5$ is selected from $C_1$–$C_6$ lower alkyl, $C_1$–$C_6$ lower alkoxy, —(CH$_2$)$_n$—$C_3$–$C_{10}$ cycloalkyl, —(CH$_2$)$_n$—S—(CH$_2$)$_n$—$C_3$–$C_{10}$ cycloalkyl, —(CH$_2$)$_n$—O—(CH$_2$)$_n$—$C_1$–$C_{10}$ cycloalkyl, or the groups of:

a) —(CH$_2$)$_n$-phenyl-O-phenyl, —(CH$_2$)$_n$-phenyl-CH$_2$-phenyl, —(CH$_2$)$_n$—O—phenyl-CH$_2$-phenyl, —(CH$_2$)$_n$-phenyl-(O—CH$_2$-phenyl)$_2$, —CH-phenyl-C(O)-benzothiazole or a moiety of the formulae:

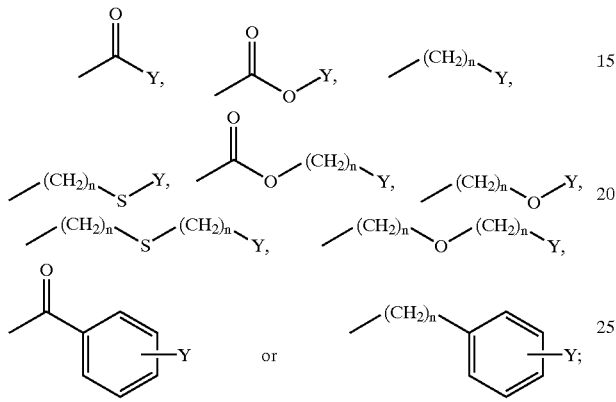

wherein n is an integer from 0 to 3, preferably 1 to 3, more preferably 1 to 2,

Y is $C_3$–$C_6$ cycloalkyl, phenyl, biphenyl, each optionally substituted by from 1 to 3 groups selected from halogen, $C_1$–$C_{10}$ alkyl, preferably $C_1$–$C_6$ alkyl, $C_1$–$C_{10}$ alkoxy, preferably $C_1$–$C_6$ alkoxy, —NO$_2$, —NH$_2$, —CN, or —CF$_3$; or a) a five-membered heterocyclic ring containing one or two ring heteroatoms selected from N, S or O including, but not limited to, furan, pyrrole, thiophene, imidazole, pyrazole, isothiazole, isoxazole, pyrrolidine, pyrroline, imidazolidine, pyrazolidine, pyrazole, pyrazoline, imidazole, tetrazole, oxathiazole, the five-membered heterocyclic ring being optionally substituted by from 1 to 3 substituents selected from halogen, $C_1$–$C_{10}$ alkyl, preferably $C_1$–$C_6$ alkyl, $C_1$–$C_{10}$ alkoxy, preferably $C_1$–$C_6$ alkoxy, —NO$_2$, —NH$_2$, —CN, —CF$_3$, or by one phenyl ring, the phenyl ring being optionally substituted by by from 1 to 3 substituents selected from halogen, $C_1$–$C_{10}$ alkyl, preferably $C_1$–$C_6$ alkyl, $C_1$–$C_{10}$ alkoxy, preferably $C_1$–$C_6$ alkoxy, —NO$_2$, —NH$_2$, —CN, —CF$_3$; or b) a six-membered heterocyclic ring containing one, two or three ring heteroatoms selected from N, S or O including, but not limited to, pyran, pyridine, pyrazine, pyrimidine, pyridazine, piperidine, piperazine, tetrazine, thiazine, thiadizine, oxazine, or morpholine, the six-membered heterocyclic ring being optionally substituted by from 1 to 3 substituents selected from halogen, $C_1$–$C_{10}$ alkyl, preferably $C_1$–$C_6$ alkyl, $C_1$–$C_{10}$ alkoxy, preferably $C_1$–$C_6$ alkoxy, —CHO, —NO$_2$, —NH$_2$, —CN, —CF$_3$ or —OH; or c) a bicyclic ring moiety containing from 8 to 10 ring atoms and optionally containing from 1 to 3 ring heteroatoms selected from N, S or O including, but not limited to benzofuran, chromene, indole, isoindole, indoline, isoindoline, napthalene, purine, indolizine, indazole, quinoline, isoquinoline, quinolizine, quinazoline, cinnoline, phthalazine, or napthyridine, the bicyclic ring moiety being optionally substituted by from 1 to 3 substituents selected from halogen, $C_1$–$C_{10}$ alkyl, preferably $C_1$–$C_6$ alkyl, $C_1$–$C_{10}$ alkoxy, preferably $C_1$–$C_6$ alkoxy, —CHO, —NO$_2$, —NH$_2$, —CN, —CF$_3$ or —OH;

d) a moiety of the formulae —(CH$_2$)$_n$—A, —(CH$_2$)$_n$—S—A, or —(CH$_2$)$_n$—O—A, wherein A is the moiety:

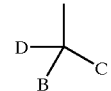

wherein

D is H, $C_1$–$C_6$ lower alkyl, $C_1$–$C_6$ lower alkoxy, —CF$_3$ or —(CH$_2$)$_n$—CF$_3$;

B and C are independently selected from phenyl, pyridinyl, pyrimidinyl, furyl, thienyl or pyrrolyl groups, each optionally substituted by from 1 to 3, preferably 1 to 2, substituents selected from H, halogen, —CN, —CHO, —CF$_3$, —OH, —$C_1$–$C_6$ alkyl, $C_1$–$C_6$ alkoxy, —NH$_2$, —N($C_1$–$C_6$)$_2$, —NH ($C_1$–$C_6$), —N—C(O)—($C_1$–$C_6$), —NO$_2$, or by a 5- or 6-membered heterocyclic or heteroaromatic ring containing 1 or 2 heteroatoms selected from O, N or S, such as, for example, morpholino; or a pharmaceutically acceptable salt thereof.

One group of compounds within this invention are those in which the indole or indoline 2-position (R$_4$) is substituted only by hydrogen and the substituents at the other indole or indoline positions are as described above.

Another R$_3$ is —L$^1$—M$^1$, wherein L$^1$ is as defined above, more preferably wherein L$^1$ is a chemical bond, and M$^1$ is the moiety:

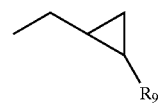

and R$_9$ is as defined in the broad genus above.

Another group of this invention comprises compounds in which R$_2$ and R$_4$ are hydrogen and the groups at R$_1$, R$_1$', R$_3$, and R$_5$ are as defined above. Within this group are two further preferred groups. In the first, R$_1$ is in the indole or indoline 5 position and in the second R$_1$ is in the indole or indoline 6 position.

In a further preferred group herein, R$_1$ is in the indole or indoline 5-position and is benzyloxy, R$_2$ and R$_4$ are hydrogen and R$_3$ and R$_4$ are as defined above.

Among the more preferred compounds of this invention are those of the following formulae:

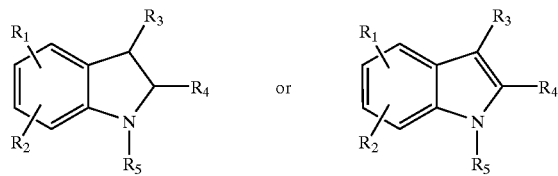

wherein:

R$_1$ is selected from H, halogen, —CF$_3$, —OH, —$C_1$–$C_{10}$ alkyl, preferably —$C_1$–$C_6$ alkyl, —S—$C_1$–$C_{10}$ alkyl, preferably —S—$C_1$-$C_6$ alkyl, $C_1$-$C_{10}$ alkoxy, preferably $C_1$-$C_6$ alkoxy, —CN, —$NO_2$, —$NH_2$, phenyl, —O-phenyl, —S-phenyl, benzyl, —O-benzyl, —S-benzyl or a moiety of the formulae:

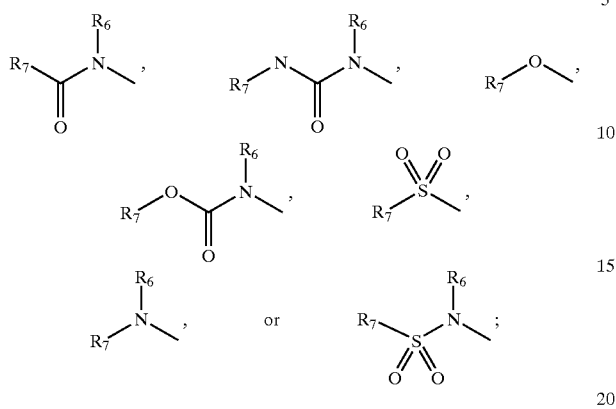

$R_6$ is selected from H, $C_1$-$C_6$ alkyl, $C_1$-$C_6$ alkoxy, phenyl, —O-phenyl, benzyl, —O-benzyl, the phenyl and benzyl rings of these groups being optionally substituted by from 1 to 3 substituents selected from halogen, $C_1$-$C_6$ alkyl, $C_1$-$C_6$ alkoxy, —$NO_2$, —$NH_2$, —CN, —$CF_3$, or —OH;

$R_7$ is selected from —$(CH_2)_n$—COOH, —$(CH_2)_n$—N—$(C_1$-$C_6$ alkyl$)_2$, —$(CH_2)_n$—NH—$(C_1$-$C_6$ alkyl), —$CF_3$, $C_1$-$C_6$ alkyl, $C_3$-$C_5$ cycloalkyl, $C_1$-$C_6$ alkoxy, —NH—$(C_1$-$C_6$ alkyl), —N—$(C_1$-$C_6$ alkyl$)_2$, pyridinyl, thienyl, furyl, pyrrolyl, quinolyl, $(CH_2)_n$ phenyl, phenyl,—O-phenyl, benzyl, —O-benzyl, adamantyl, or morpholinyl, —$(CH_2)_n$-phenyl-O-phenyl, —$(CH_2)_n$-phenyl-$CH_2$-phenyl, —$(CH_2)_n$—O-phenyl-$CH_2$-phenyl, —$(CH_2)_n$-phenyl-$(O$—$CH_2$-phenyl$)_2$, the rings of these groups being optionally substituted by from 1 to 3 substituents selected from halogen, $C_1$-$C_6$ alkyl, $C_1$-$C_6$ alkoxy, —$NH_2$, —$NO_2$, —$CF_3$,$CO_2H$, or —OH;

$R_2$ is selected from H, halogen, —$CF_3$, —OH, —$C_1$-$C_{10}$ alkyl, preferably —$C_1$-$C_6$ alkyl, $C_1$-$C_{10}$ alkoxy, preferably $C_1$-$C_6$ alkoxy, —CHO, —CN, —$NO_2$, —$NH_2$, —NH—$C_1$-$C_6$ alkyl, —$N(C_1$-$C_6$ alkyl$)_2$, —N—$SO_2$—$C_1$-$C_6$ alkyl, or —$SO_2$—$C_1$-$C_6$ alkyl;

$R_3$ is selected from —COOH, —C(O)—COOH, —$(CH_2)_n$—C(O)—COOH, —$(CH_2)_n$—COOH, —CH=CH—COOH, —$(CH_2)_n$—tetrazole,

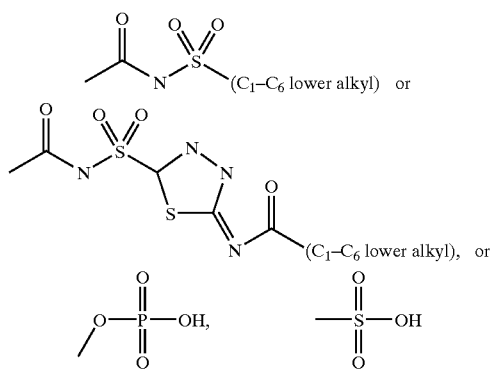

or a moiety selected from the formulae —$L^1$—$M^1$; wherein $L^1$ is a bridging or linking moiety selected from a chemical bond, —S—, —O—, —$(CH_2)_n$—, —$SO_2$—, —C(O)—, —$(CH_2)_n$—C(O)—, —$(CH_2)_n$—C(O)—$(CH_2)_n$—, —$(CH_2)_n$—O—$(CH_2)_n$—, —$(CH_2)_n$—S—$(CH_2)_n$—, —$(CH_2)_n$—SO—$(CH_2)_n$—, —$(CH_2)_n$—$SO_2$—$(CH_2)_n$—, or —$(CH_2)_n$—CH=CH—$(CH_2)_n$—O—; —C(Z)—N$(R_6)$—, —C(Z)—N$(R_6)$—$(CH_2)_n$—, —C(O)—C(Z)—N$(R_6)$—, —C(O)—C(Z)—N$(R_6)$—$(CH_2)_n$—, —C(Z)—NH—$SO_2$—, or —C(Z)—NH—$SO_2$—$(CH_2)_n$—;

n is an integer from 0 to 3

$M^1$ is selected from the group of —COOH, —$(CH_2)_n$—COOH, —$(CH_2)_n$—C(O)—COOH, tetrazole,

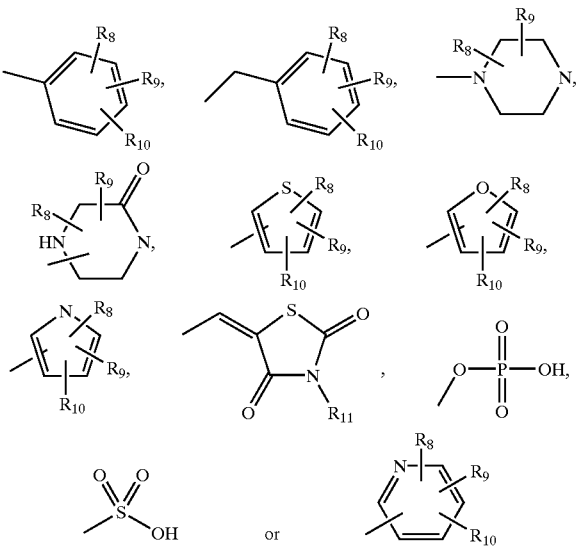

$R_8$, in each appearance, is independently selected from H, —COOH, —$(CH_2)_n$—COOH, —$(CH_2)_n$—C(O)—COOH, tetrazole,

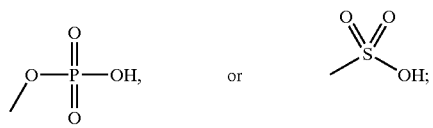

$R_9$ is selected from H, halogen, —$CF_3$, —OH, —COOH, —$(CH_2)_n$—COOH, —$(CH_2)_n$—C(O)—COOH, —$C_1$-$C_6$ alkyl, —O—$C_1C_6$ alkyl, —NH$(C_1$-$C_6$ alkyl), or —N$(C_1$-$C_6$ alkyl$)_2$;

$R_{10}$ is selected from the group of H, halogen, —$CF_3$, —OH, —$(CH_2)_n$—COOH, —$(CH_2)_n$—C(O)—COOH, —$C_1$-$C_6$ alkyl, —O—$C_1$-$C_6$ alkyl, —NH$(C_1$-$C_6$ alkyl), —N$(C_1$-$C_6$ alkyl$)_2$,

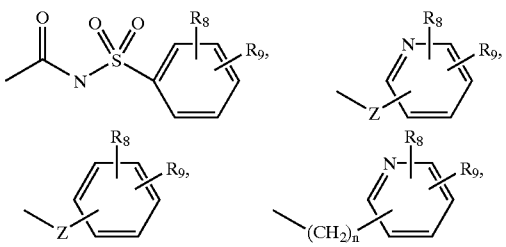

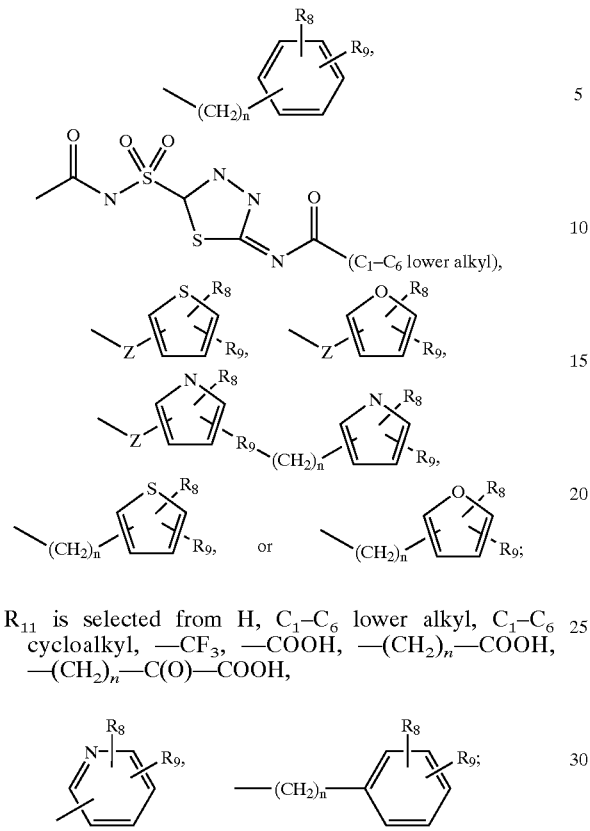

$R_{11}$ is selected from H, $C_1$–$C_6$ lower alkyl, $C_1$–$C_6$ cycloalkyl, —$CF_3$, —COOH, —$(CH_2)_n$—COOH, —$(CH_2)_n$—C(O)—COOH,

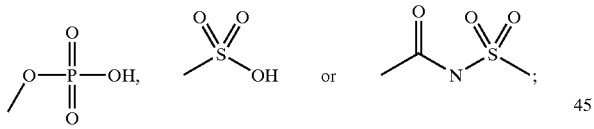

with a proviso that the complete moiety at the indole or indoline 3-position created by any combination of $R_3$, $L^1$, $M^1$, $R_8$, $R_9$, $R_{10}$, and/or $R_{11}$ shall contain at least one acidic moiety selected from or containing a carboxylic acid, a tetrazole, or a moiety of the formulae: —C(O)—$NH_2$, —$(CH_2)_n$—C(O)—$NH_2$,

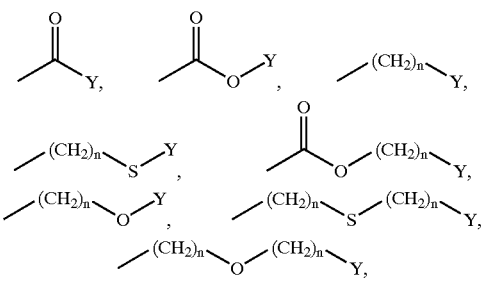

n is an integer from 0 to 3;
$R_4$ is selected from H, —$CF_3$, $C_1$–$C_6$ lower alkyl, $C_1$–$C_6$ lower alkoxy, $C3$–$C_{10}$ cycloalkyl, —$C_1$–$C_6$ alkyl-$C_3$–$C_{10}$ cycloalkyl, —CHO, halogen, or a moiety of the formula —$L^2$—$M^2$:
  $L^2$ indicates a linking or bridging group of the formulae —$(CH_2)_n$—, —S—, —O—, —C(O)—, —$(CH_2)_n$—C(O)—, —$(CH_2)_n$—C(O)—$(CH_2)_n$—, —$(CH_2)_n$—O—$(CH_2)_n$—, or —$(CH_2)_n$—S—$(CH_2)_n$—;
  $M^2$ is selected from the group of H, $C_1$–$C_6$ lower alkyl, $C_1$–$C_6$ lower alkoxy, $C_3$–$C_{10}$ cycloalkyl, phenyl or benzyl, the cycloalkyl, phenyl or benzyl rings being optionally substituted by from 1 to 3 substituents selected from halogen, $C_1$–$C_{10}$ alkyl, preferably $C_1$–$C_6$ alkyl, $C_1$–$C_{10}$ alkoxy, preferably $C_1$–$C_6$ alkoxy, —$NO_2$, —$NH_2$, —CN, or —$CF_3$; or
  a) a five-membered heterocyclic ring containing one or two ring heteroatoms selected from N, S or O including, but not limited to, furan, pyrrole, thiophene, imidazole, pyrazole, pyrrolidine, or tetrazole, the five-membered heterocyclic ring being optionally substituted by from 1 to 3 substituents selected from halogen, $C_1$–$C_{10}$ alkyl, preferably $C_1$–$C_6$ alkyl, $C_1$–$C_{10}$ alkoxy, preferably $C_1$–$C_6$ alkoxy, —$NO_2$, —$NH_2$, —CN, or —$CF_3$; or
  b) a six-membered heterocyclic ring containing one, two or three ring heteroatoms selected from N, S or O including, but not limited to pyridine, pyrimidine, piperidine, piperazine, or morpholine, the six-membered heterocyclic ring being optionally substituted by from 1 to 3 substituents selected from halogen, $C_1$–$C_{10}$ alkyl, preferably $C_1$–$C_6$ alkyl, $C_1$–$C_{10}$ alkoxy, preferably $C_1$–$C_6$ alkoxy, —CHO, —$NO_2$, —$NH_2$, —CN, —$CF_3$ or —OH; or
  c) a bicyclic ring moiety containing from 8 to 10 ring atoms and optionally containing from 1 to 3 ring heteroatoms selected from N, S or O including, but not limited to benzofuran, indole, indoline, napthalene, purine, or quinoline, the bicyclic ring moiety being optionally substituted by from 1 to 3 substituents selected from halogen, $C_1$–$C_{10}$ alkyl, preferably $C_1$–$C_6$ alkyl, $C_1$–$C_{10}$ alkoxy, preferably $C_1$–$C_6$ alkoxy, —CHO, —$NO_2$, —$NH_2$, —CN, —$CF_3$ or —OH;

n is an integer from 0 to 3

$R_5$ is selected from $C_1$–$C_6$ lower alkyl, $C_1$–$C_6$ lower alkoxy, —$(CH_2)_n$—$C_3$–$C_{10}$ cycloalkyl, —$(CH_2)_n$—S—$(CH_2)_n$—$C_3$–$C_{10}$ cycloalkyl, —$(CH_2)_n$—O—$(CH_2)_n$—$C_3$–$C_{10}$ cycloalkyl, or the groups of:
  a) —$(CH_2)_n$-phenyl-O-phenyl, —$(CH_2)_n$-phenyl-$CH_2$-phenyl, —$(CH_2)_n$—O-phenyl-$CH_2$-phenyl, —$(CH_2)_n$-phenyl-(O—$CH_2$-phenyl)$_2$, —$CH_2$-phenyl-C(O)-benzothiazole or a moiety of the formulae:

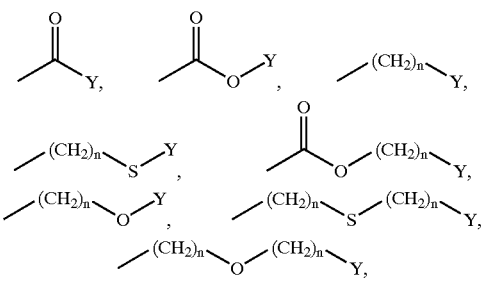

wherein n is an integer from 0 to 3, preferably 1 to 3, more preferably 1 to 2, Y is $C_3$—$C_5$ cycloalkyl, phenyl, benzyl, napthyl, pyridinyl, quinolyl, furyl, thienyl, pyrrolyl, benzothiazole and pyrimidinyl, the rings of these groups being optionally substituted by from 1 to 3 substituents selected from H, halogen, —$CF_3$, —OH, —$C_1$–$C_6$ alkyl, $C_1$–$C_6$ alkoxy, —CN, —$NH_2$, —$NO_2$ or a five membered heterocyclic ring containing one heteroatom selected from N, S, or O, preferably S or O; or
  b) a moiety of the formulae —$(CH_2)_n$—A, —$(CH_2)_n$—S—A, or —$(CH_2)_n$—O—A, wherein A is the moiety:

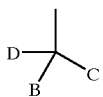

wherein
D is H, $C_1$–$C_6$ lower alkyl, $C_1$–$C_6$ lower alkoxy, —$CF_3$ or —$(CH_2)_n$—$CF_3$;
B and C are independently selected from phenyl, pyridinyl, pyrimidinyl, furyl, thienyl or pyrrolyl groups, each optionally substituted by from 1 to 3, preferably 1 to 2, substituents selected from H, halogen, —$CF_3$, —OH, —$C_1$–$C_6$ alkyl, $C_1$–$C_6$ alkoxy, —$NH_2$ or —$NO_2$;
or a pharmaceutically acceptable salt thereof.

One group of compounds within this invention are those in which the indole or indoline 2-position ($R_4$) is substituted only by hydrogen and the substituents at the other indole or indoline positions are as described above.

In an another preferred group of this invention $R_1$ is in the indole or indoline 5 or 6 position and is cyclopentylcarboxamide or cyclopentyloxycarbonylamino, $R_2$ and $R_4$ are hydrogen, and $R_3$ and $R_5$ are as defined above.

A further preferred group of this invention consists of $R_1$ and $R_2$ at the indole or indoline 5 and or 6 position and are each selected from the group consisting of $C_1$–$C_6$alkoxy, cyano, sulfonyl and halo, $R_2$ and $R_4$ are hydrogen, and $R_3$ and $R_5$ are as defined above.

Another group of this invention comprises compounds in which $R_2$ and $R_4$ are hydrogen and the groups at $R_1$, $R_3$, and $R_5$ are as defined above. Within this group are two further preferred groups. In the first, $R_1$ is in the indole or indoline 5 position and in the second $R_1$ is in the indole or indoline 6 position.

In a further preferred group herein, $R_1$ is in the indole or indoline 5-position and is benzyloxy, $R_2$ and $R_4$ are hydrogen and $R_3$ and $R_5$ are as defined above.

A preferred group of compounds of this invention have the following formulae:

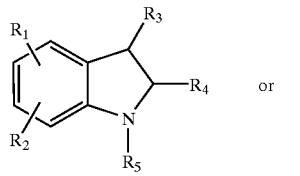 or 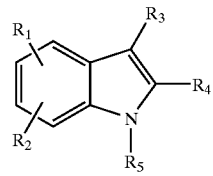

wherein:
$R_1$ is selected form H, halogen, —$CF_3$, —OH, —$C_1$–$C_6$ alkyl, $C_1$–$C_6$ alkoxy, —$NO_2$, —$NH_2$, CN, phenyl, —O-phenyl, benzyl, —O-benzyl, —S-benzyl or a moiety of the formulae:

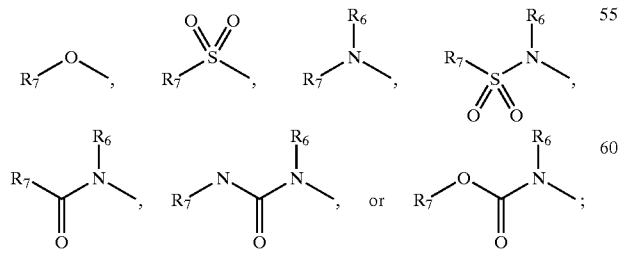

$R_6$ is selected from H, $C_1$–$C_6$ alkyl, $C_1$–$C_6$ alkoxy, phenyl, —O-phenyl, benzyl, —O-benzyl, the phenyl and benzyl rings of these groups being optionally substituted by from 1 to 3 substituents selected from halogen, $C_1$–$C_6$ alkyl, $C_1$–$C_6$ alkoxy, —$NH_2$, —$NO_2$, —$CF_3$, or —OH;

$R_7$ is selected from —$(CH_2)_n$—COOH, —$(CH_2)_n$—N—$(C_1$–$C_6$ alkyl$)_2$, —$(CH_2)_n$—NH—$(C_1$–$C_6$ alkyl), —$CF_3$, $C_1$–$C_6$ alkyl, $C_3$–$C_5$ cycloalkyl, $C_1$–$C_6$ alkoxy, —NH—$(C_1$–$C_6$ alkyl), —N—$(C_1$–$C_6$ alkyl$)_2$, pyridinyl, thienyl, furyl, pyrrolyl, quinolyl, $(CH_2)_n$ phenyl, phenyl,—O-phenyl, benzyl, —O-benzyl, adamantyl, or morpholinyl, —$(CH_2)_n$-phenyl-O-phenyl, —$(CH_2)_n$-phenyl-$CH_2$-phenyl, —$(CH_2)_n$—O-phenyl-$CH_2$-phenyl, —$(CH_2)_n$-phenyl-(O—$CH_2$-phenyl$)_2$, the rings of these groups being optionally substituted by from 1 to 3 substituents selected from halogen, $C_1$–$C_6$ alkyl, $C_1$—$C_6$ alkoxy, —NH2, —$NO_2$, —$CF_3$,$CO_2H$, or —OH;

$R_2$ is selected from H, halogen, —CN, —CHO, —$CF_3$, —OH, $C_1$–$C_{10}$ alkyl, preferably $C_1$–$C_6$ alkyl, $C_1$–$C_{10}$ alkoxy, preferably $C_1$–$C_6$ alkoxy, —CHO, —CN, —$NO_2$, —$N_2$, —NH—$C_1$–$C_6$ alkyl, —N($C_1$–$C_6$ alkyl$)_2$, —N—$SO_2$—$C_1$–$C_6$ alkyl, or —$SO_2$—$C_1$–$C_6$ alkyl;

$R_3$ is selected from —COOH, —C(O)—COOH, —$(CH_2)_n$—C(O)—COOH, —$(CH_2)_n$—COOH, —CH=CH—COOH, —$(CH_2)_n$—tetrazole,

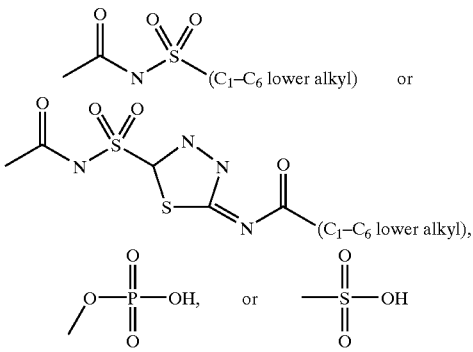

or a moiety selected from the formulae —$L^1$—$M^1$;
wherein $L^1$ is a bridging or linking moiety selected from a chemical bond, —S—, —O—, —C(O)—, —$(CH_2)_n$—, —$SO_2$—, —C(O)—, —$(CH_2)_n$—C(O)—, —$(CH_2)_n$—C(O)—$(CH_2)_n$—, —$(CH_2)_n$—O—$(CH_2)_n$—, —$(CH_2)_n$—S—$(CH_2)_n$—, —$(CH_2)_n$—SO—$(CH_2)_n$—, —$(CH_2)_n$—$SO_2$—$(CH_2)_n$—, or —$(CH_2)_n$—CH=CH—$(CH_2)_n$—O—; —C(Z)—N($R_6$)—, —C(Z)—N($R_6$)—$(CH_2)_n$—C(O)—C(Z)—N($R_6$)—, —C(O)—C(Z)—N($R_6$)—$(CH_2)_n$—, —C(Z)—NH—$SO_2$—, or —C(Z)—NH—$SO_2$—$(CH_2)_n$—;
n is an integer from 0 to 3
$M^1$ is selected from the group of —COOH, —$(CH_2)_n$—COOH, —$(CH_2)_n$—C(O)—COOH, tetrazole,

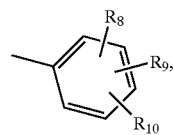 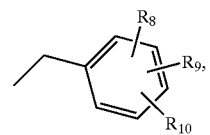

-continued

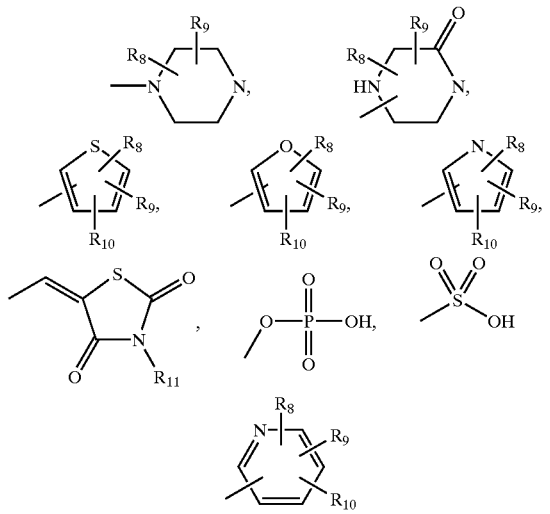

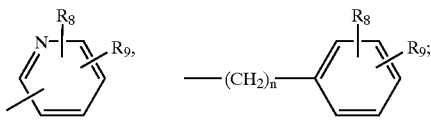

with a proviso that the complete moiety at the indole or indoline 3-position created by any combination of $R_3$, $L^1$, $M^1$, $R_8$, $R_9$, $R_{10}$, and/or $R_{11}$ shall contain at least one acidic moiety selected from or containing a carboxylic acid, a tetrazole, or a moiety of the formulae:
—C(O)—NH$_2$, —(CH$_2$)$_n$—C(O)—NH$_2$,

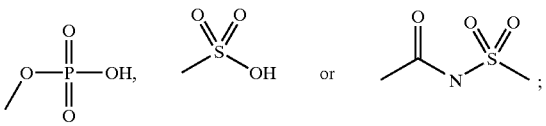

$R_8$, in each appearance, is independently selected from H, —COOH, —(CH$_2$)$_n$—COOH, —(CH$_2$)$_n$—C(O)—COOH, tetrazole,

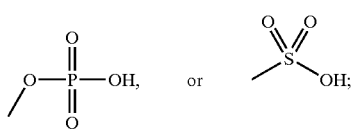

$R_9$ is selected from H, halogen, —CF$_3$, —OH, —COOH, —(CH$_2$)$_n$—COOH, —(CH$_2$)$_n$—C(O)—COOH, —C$_1$–C$_6$ alkyl, —O—C$_1$–C$_6$ alkyl, —NH(C$_1$–C$_6$ alkyl), —N(C$_1$–C$_6$ alkyl)$_2$;

$R_{10}$ is selected from the group of H, halogen, —CF$_3$, —OH, —COOH, —(CH$_2$)$_n$—COOH, —(CH$_2$)$_n$—C(O)—COOH, —C$_1$–C$_6$ alkyl, —O—C$_1$–C$_6$ alkyl, —NH(C$_1$–C$_6$ alkyl), —N(C$_1$–C$_6$ alkyl)$_2$,

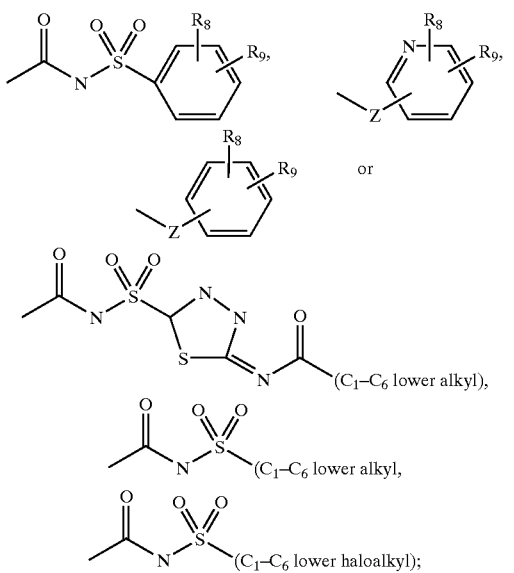

$R_{11}$ is selected from H, C$_1$–C$_6$ lower alkyl, C$_1$–C$_6$ cycloalkyl, —CF$_3$, —COOH, —(CH$_2$)$_n$—COOH, —(CH$_2$)$_n$—C(O)—COOH, n is an integer from 0 to 3;

$R_4$ is selected from H, —CF$_3$, C$_1$–C$_6$ lower alkyl, C$_1$–C$_6$ lower alkoxy, C$_3$–C$_{10}$ cycloalkyl, —C$_1$–C$_6$ alkyl-C$_3$–C$_{10}$ cycloalkyl, —CHO, halogen, or a moiety of the formula —L$^2$—M$^2$:

$L^2$ indicates a linking or bridging group of the formulae —(CH$_2$)$_n$—, —S—, —O—, —C(O)—, —(CH$_2$)$_n$—C(O)—, —(CH$_2$)$_n$—C(O)—(CH$_2$)$_n$—, —(CH$_2$)$_n$—O—(CH$_2$)$_n$—, or —(CH$_2$)$_n$—S—(CH$_2$)$_n$—;

$M^2$ is selected from:
a) H, the group of C$_1$–C$_6$ lower alkyl, C$_1$–C$_6$ lower alkoxy, C$_3$–C$_{10}$ cycloalkyl, phenyl or benzyl, the cycloalkyl, phenyl or benzyl rings being optionally substituted by from 1 to 3 substituents selected from halogen, C$_1$–C$_{10}$ alkyl, preferably C$_1$–C$_6$ alkyl, C$_1$–C$_{10}$ alkoxy, preferably C$_1$–C$_6$ alkoxy, —NO$_2$, —NH$_2$, —CN, or —CF$_3$; or b) a five-membered heterocyclic ring containing one or two ring heteroatoms selected from N, S or O including, but not limited to, furan, pyrrole, thiophene, imidazole, pyrazole, pyrrolidine, pyrazole, or tetrazole, the five-membered heterocyclic ring being optionally substituted by from 1 to 3 substituents selected from halogen, C$_1$–C$_{10}$ alkyl, preferably C$_1$–C$_6$ alkyl, C$_1$–C$_{10}$ alkoxy, preferably C$_1$–C$_6$ alkoxy, —NO$_2$, —NH$_2$, —CN, or —CF$_3$; or c) a six-membered heterocyclic ring containing one, two or three ring heteroatoms selected from N, S or O including, but not limited to, pyridine, pyrazine, pyrimidine, piperidine, piperazine, thiazine, or morpholine, the six-membered heterocyclic ring being optionally substituted by from 1 to 3 substituents selected from halogen, C$_1$–C$_{10}$ alkyl, preferably C$_1$–C$_6$ alkyl, C$_1$–C$_{10}$ alkoxy, preferably C$_1$–C$_6$ alkoxy, —CHO, —NO$_2$, —NH$_2$, —CN, —CF$_3$ or —OH; or d) a bicyclic ring moiety containing from 8 to 10 ring atoms and optionally containing from 1 to 3 ring heteroatoms selected from N, S or O including, but not limited to benzofuran, chromene, indole, isoindole, indoline, isoindoline, napthalene, purine, quinoline or isoquinoline, the bicyclic ring moiety being optionally substituted by from 1 to 3 substituents selected from halogen, C$_1$–C$_{10}$ alkyl, preferably C$_1$–C$_6$ alkyl, C$_1$–C$_{10}$ alkoxy, preferably C$_1$–C$_6$ alkoxy, —CHO, —NO$_2$, —NH$_2$, —CN, —CF$_3$ or —OH;

$R_5$ is selected from $C_1-C_6$ lower alkyl, $C_1-C_6$ lower alkoxy, —$(CH_2)_n$—$C_3-C_5$ cycloalkyl, —$(CH_2)_n$—S—$(CH_2)_n$—$C_1-C_5$ cycloalkyl, —$(CH_2)_n$—O—$(CH_2)_n$—$C_3-C_5$ cycloalkyl, or the groups of:

a) —$(CH_2)_n$-phenyl-O-phenyl, —$(CH_2)_n$-phenyl-$CH_2$-phenyl, —$(CH_2)_n$—O-phenyl-$CH_2$-phenyl, —$(CH_2)_n$-phenyl-(O—$CH_2$-phenyl)$_2$, —$CH_2$-phenyl-C(O)-benzothiazole or a moiety of the formulae:

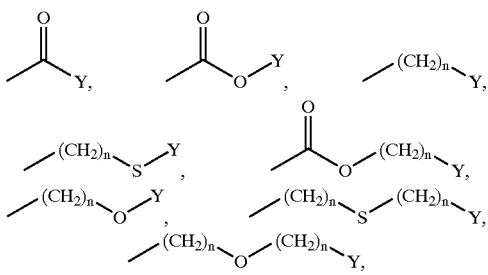

wherein n is an integer from 0 to 3, preferably 1 to 3, more preferably 1 to 2, Y is $C_3-C_5$ cycloalkyl, phenyl, benzyl, napthyl, pyridinyl, quinolyl, furyl, thienyl, pyrrolyl benzothiazole or pyrimidinyl, the rings of these groups being optionally substituted by from 1 to 3 substituents selected from H, halogen, —$CF_3$, —OH, —$C_1-C_6$ alkyl, $C_1-C_6$ alkoxy, —$NO_2$, —$NH_2$ or a five membered heterocyclic ring containing one heteroatom selected from N, S, or O, preferably S or O; or b) a moiety of the formulae —$(CH_2)_n$—A, —$(CH_2)_n$—S—A, or —$(CH_2)_n$—O—A, wherein A is the moiety:

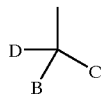

wherein

D is H, $C_1-C_6$ lower alkyl, $C_1-C_6$ lower alkoxy, —$(CH_2)_n$—$CF_3$ or —$CF_3$;

B and C are independently selected from phenyl, pyridinyl, pyrimidinyl, furyl, thienyl or pyrrolyl groups, each optionally substituted by from 1 to 3, preferably 1 to 2, substituents selected from H, halogen, —$CF_3$, —OH, —$C_1-C_6$ alkyl, $C_1-C_6$ alkoxy, —$NH_2$ or —$NO_2$;

or a pharmaceutically acceptable salt thereof.

A preferred group among the compounds above are those in which the $R_1$ substitution is at the indole or indoline ring's 5-position and the other substituents are as defined above.

Another preferred group of this invention are those of the formulae:

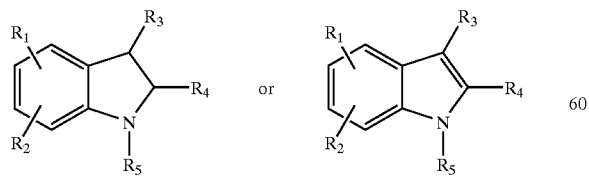

wherein:

$R_1$ is selected from H, halogen, —$CF_3$, —OH, —$C_1-C_{10}$ alkyl, preferably —$C_1-C_6$ alkyl, —S—$C_1-C_{10}$ alkyl, preferably —S—$C_1-C_6$ alkyl, $C_1-C_{10}$ alkoxy, preferably $C_1-C_6$ alkoxy, —CN, —$NO_2$, —$NH_2$, —HN($C_1-C_6$), —N($C_1-C_6$)$_2$, phenyl, —O-phenyl, —S-phenyl, benzyl, —O-benzyl, —S-benzyl, the phenyl and benzyl rings of these groups being optionally substituted by from 1 to 3 substituents selected from halogen, $C_1-C_6$ alkyl, $C_1-C_6$ alkoxy, —$NO_2$, —$NH_2$, —CN, —$CF_3$, or —OH;

or a moiety of the formulae:

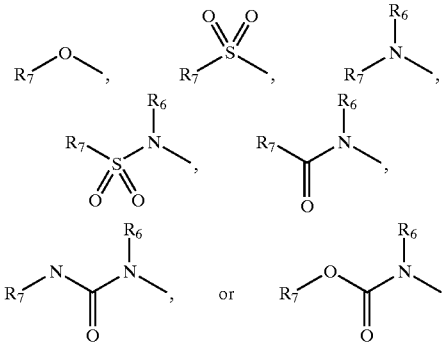

$R_6$ is selected from H, $C_1-C_6$ alkyl, $C_1-C_6$ alkoxy, phenyl, —O-phenyl, benzyl, —O-benzyl, the phenyl and benzyl rings of these groups being optionally substituted by from 1 to 3 substituents selected from halogen, $C_1-C_6$ alkyl, $C_1-C_6$ alkoxy, —$NO_2$, —$CF_3$, or —OH;

$R_7$ is selected from —$(CH_2)_n$—COOH, —$(CH_2)_n$—N—($C_1-C_6$ alkyl)$_2$, —$(CH_2)_n$—NH—($C_1-C_6$ alkyl), —$CF_3$, $C_1-C_6$ alkyl, $C_3-C_5$ cycloalkyl, $C_1-C_6$ alkoxy, —NH—($C_{1-C6}$ alkyl), —N—($C_1-C_6$ alkyl)$_2$, pyridinyl, thienyl, furyl, pyrrolyl, quinolyl, $(CH_2)_n$ phenyl, phenyl,—O-phenyl, benzyl, —O-benzyl, adamantyl, or morpholinyl, —$(CH_2)_n$-phenyl-O-phenyl, —$(CH_2)_n$-phenyl-$CH_2$-phenyl, —$(CH_2)_n$—O-phenyl-$CH_2$-phenyl, —$(CH_2)_n$-phenyl-(O—$CH_2$-phenyl)$_2$, the rings of these groups being optionally substituted by from 1 to 3 substituents selected from halogen, $C_1-C_6$ alkyl, $C_1-C_6$ alkoxy, —$NH_2$, —$NO_2$, —$CF_3$,$CO_2H$, or —OH;

$R_2$ is selected from H, halogen, —CN, —CHO, —$CF_3$, —OH, $C_1-C_{10}$ alkyl, preferably $C_1-C_6$ alkyl, $C_1-C_{10}$ alkoxy, preferably $C_1-C_6$ alkoxy, —CHO, —CN, —$NO_2$, —$NH_2$, —NH—$C_1-C_6$ alkyl, —N($C_1-C_6$ alkyl)$_2$, —N—$SO_2$—$C_1-C_6$ alkyl, or —$SO_2$—$C_1-C_6$ alkyl;

$R_3$ is selected from —COOH, —C(O)—COOH, —$(CH_2)_n$—C(O)—COOH, —$(CH_2)_n$—COOH, —CH=CH—COOH, —$(CH_2)_n$-tetrazole,

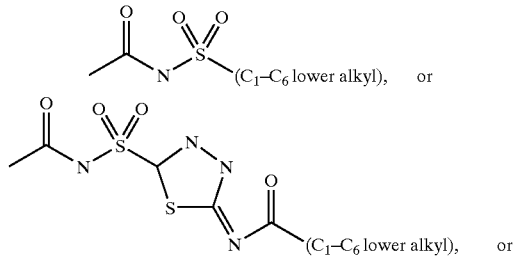

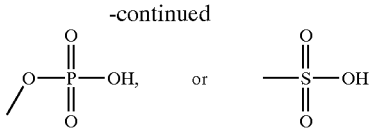

or a moiety selected from the formulae —L¹—M¹;
wherein L¹ is a bridging or linking moiety selected from a chemical bond, , —(CH₂)ₙ—, —SO₂—, —C(O)—, —(CH₂)ₙ—C(O)—, —(CH₂)ₙ—C(O)—(CH₂)ₙ—, —(CH₂)ₙ—O—(CH₂)ₙ—, —(CH₂)ₙ—S—(CH₂)ₙ—, —(CH₂)ₙ—SO—(CH₂)ₙ—, —(CH₂)ₙ—SO₂—(CH₂)ₙ—, or —(CH₂)ₙ—CH=CH—(CH₂)ₙ—O—;
n is an integer from 0 to 3
M¹ is selected from the group of —COOH, —(CH₂)ₙ—COOH, —(CH₂)ₙ—C(O)—COOH, tetrazole,

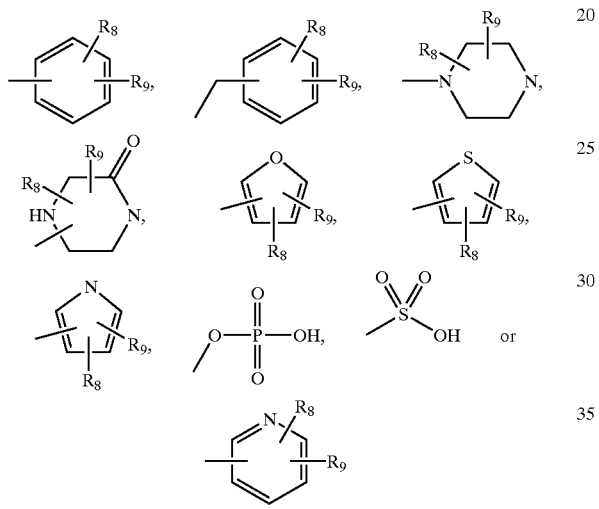

$R_8$, in each appearance, is independently selected from H, —COOH, —(CH₂)ₙ—COOH, —(CH₂)ₙ—C(O)—COOH, tetrazole, —C(O)—NH₂, —(CH₂)ₙ—C(O)—NH₂,

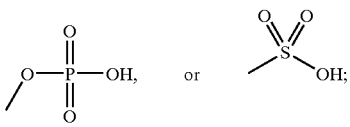

n is an integer from 0 to 3;
$R_9$ is selected from H, halogen, —CF₃, —OH, —COOH, —(CH₂)ₙ—COOH, —(CH₂)ₙ—C(O)—COOH, —C₁-C₆ alkyl, —O—C₁-C₆ alkyl, —NH(C₁-C₆ alkyl), —N(C₁-C₆ alkyl)₂;
$R_4$ is selected from H, —CF₃, C₁-C₆ lower alkyl, C₁-C₆ lower alkoxy, C₃-C₁₀ cycloalkyl, —C₁-C₆ alkyl-C₃-C₁₀ cycloalkyl, —CHO, halogen, or a moiety of the formula —L²—M²:
L² indicates a linking or bridging group of the formulae —(CH₂)ₙ—, —S—, —O—, —C(O)—, —(CH₂)ₙ—C(O)—, —(CH₂)ₙ—C(O)—(CH₂)ₙ—, —(CH₂)ₙ—O—(CH₂)ₙ—, or —(CH₂)ₙ—S—(CH₂)ₙ—;
M² is selected from:
a) H, the group of C₁-C₆ lower alkyl, C₁-C₆ lower alkoxy, C₃-C₁₀ cycloalkyl, phenyl or benzyl, the cycloalkyl, phenyl or benzyl rings being optionally substituted by from 1 to 3 substituents selected from halogen, C₁-C₁₀ alkyl, preferably C₁-C₆ alkyl, C₁-C₁₀ alkoxy, preferably C₁-C₆ alkoxy, —NO₂, —NH₂, —CN, or —CF₃; or
b) a five-membered heterocyclic ring containing one or two ring heteroatoms selected from N, S or O including, but not limited to, furan, pyrrole, thiophene, imidazole, pyrazole, pyrrolidine, pyrazole, or tetrazole, the five-membered heterocyclic ring being optionally substituted by from 1 to 3 substituents selected from halogen, C₁-C₁₀ alkyl, preferably C₁-C₆ alkyl, C₁-C₁₀ alkoxy, preferably C₁-C₆ alkoxy, —NO₂, —NH₂, —CN, or —CF₃; or
c) a six-membered heterocyclic ring containing one, two or three ring heteroatoms selected from N, S or O including, but not limited to, pyridine, pyrazine, pyrimidine, piperidine, piperazine, thiazine, or morpholine, the six-membered heterocyclic ring being optionally substituted by from 1 to 3 substituents selected from halogen, C₁-C₁₀ alkyl, preferably C₁-C₆ alkyl, C₁-C₁₀ alkoxy, preferably C₁-C₆ alkoxy, —CHO, —NO₂, —NH₂, —CN, —CF₃ or —OH; or
d) a bicyclic ring moiety containing from 8 to 10 ring atoms and optionally containing from 1 to 3 ring heteroatoms selected from N, S or O including, but not limited to benzofuran, chromene, indole, isoindole, indoline, isoindoline, napthalene, purine, quinoline or isoquinoline, the bicyclic ring moiety being optionally substituted by from 1 to 3 substituents selected from halogen, C₁-C₁₀ alkyl, preferably C₁-C₆ alkyl, C₁-C₁₀ alkoxy, preferably C₁-C₆ alkoxy, —CHO, —NO₂, —NH₂, —CN, —CF₃ or —OH;

$R_5$ is selected from C₁-C₆ lower alkyl, C₁-C₆ lower alkoxy, —(CH₂)ₙ—C₃-C₅ cycloalkyl or —(CH₂)ₙ—A, —(CH₂)ₙ—S—A, or —(CH₂)ₙ—O—A wherein A is selected from:

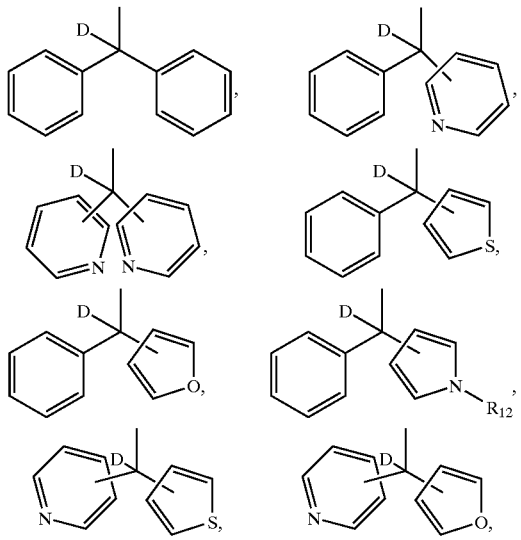

-continued

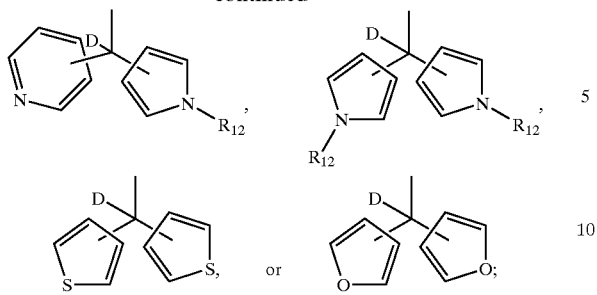

D is H, $C_1$–$C_6$ lower alkyl, $C_1$–$C_6$ lower alkoxy, or —$CF_3$;

$R_{12}$ is H, $C_1$–$C_6$ lower alkyl, $C_1$–$C_6$ lower alkoxy, or —$CF_3$;

or a pharmaceutically acceptable salt thereof.

Other compounds of this invention have the following formulae:

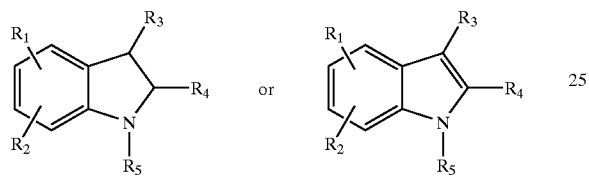

wherein:

$R_1$ is selected from H, halogen, —$CF_3$, —OH, —$C_1$–$C_{10}$ alkyl, preferably —$C_1$–$C_6$ alkyl, —S—$C_1$–$C_{10}$ alkyl, preferably —S—$C_1$–$C_6$ alkyl, $C_1$–$C_{10}$ alkoxy, preferably $C_1$–$C_6$ alkoxy, —CN, —$NO_2$, —$NH_2$, —HN($C_1$–$C_6$), —N($C_1$–$C_6$)$_2$, phenyl, —O-phenyl, —S-phenyl, benzyl, —O-benzyl, —S-benzyl, the phenyl and benzyl rings of these groups being optionally substituted by from 1 to 3 substituents selected from halogen, $C_1$–$C_6$ alkyl, $C_1$–$C_6$ alkoxy, —$NO_2$, —$NH_2$, —CN, —$CF_3$, or —OH;

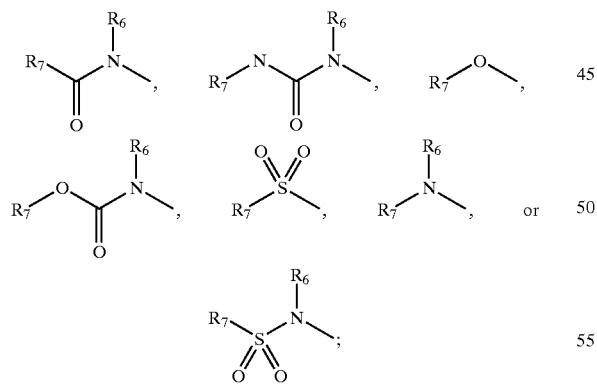

$R_6$ is selected from H, $C_1$–$C_6$ alkyl, $C_1$–$C_6$ alkoxy, phenyl, —O-phenyl, benzyl, —O-benzyl, the phenyl and benzyl rings of these groups being optionally substituted by from 1 to 3 substituents selected from halogen, $C_1$–$C_6$ alkyl, $C_1$–$C_6$ alkoxy, —$NH_2$, —$NO_2$, —$CF_3$, or —OH;

$R_7$ is selected from —$(CH_2)_n$—COOH, —$(CH_2)_n$—N—($C_1$–$C_6$ alkyl)$_2$, —$(CH_2)_n$—NH—($C_1$–$C_6$ alkyl), —$CF_3$, $C_1$–$C_6$ alkyl, $C_3$–$C_5$ cycloalkyl, $C_1$–$C_6$ alkoxy, —NH—($C_1$–$C_6$ alkyl), —N—($C_1$–$C_6$ alkyl)$_2$, pyridinyl, thienyl, furyl, pyrrolyl, quinolyl, $(CH_2)_n$ phenyl, phenyl, —O-phenyl, benzyl, —O-benzyl, adamantyl, or morpholinyl, —$(CH_2)_n$-phenyl-O-phenyl, —$(CH_2)_n$-phenyl-$CH_2$-phenyl, —$(CH_2)_n$—O-phenyl-$CH_2$-phenyl, —$(CH_2)_n$-phenyl-(O—$CH_2$-phenyl)$_2$, the rings of these groups being optionally substituted by from 1 to 3 substituents selected from halogen, $C_1$–$C_6$ alkyl, $C_1$–$C_6$ alkoxy, —$NH_2$, —$NO_2$, —$CF_3$,$CO_2H$, or —OH;

$R_2$ is selected from H, halogen, —CN, —CHO, —$CF_3$, —OH, $C_1$–$C_{10}$ alkyl, preferably $C_1$–$C_6$ alkyl, $C_1$–$C_{10}$ alkoxy, preferably $C_1$–$C_6$ alkoxy, —CHO, —CN, —$NO_2$, —$NH_2$, —NH—$C_1$–$C_6$ alkyl, —N($C_1$–$C_6$ alkyl)$_2$, —N—$SO_2$—$C_1$–$C_6$ alkyl, or —$SO_2$—$C_1$–$C_6$ alkyl;

$R_3$ is selected from —COOH, —C(O)—COOH, —$(CH_2)_n$—C(O)—COOH, —$(CH_2)_n$—COOH, $(CH_2)_n$—CH=CH—COOH, —$(CH_2)_n$—tetrazole,

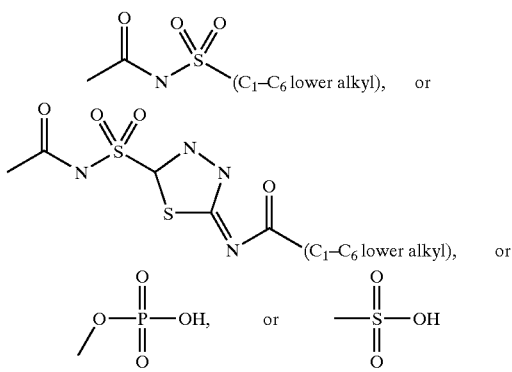

or a moiety selected from the formulae —$L^1$—$M^1$ or $L^2M^2$;

$L^1$ is a bridging or linking moiety selected from a chemical bond, —$(CH_2)_n$—, —$(CH_2)_n$—C(O)—$(CH_2)_n$—, —$(CH_2)_n$—O—$(CH_2)_n$—, —$(CH_2)_n$—S—$(CH_2)_n$—, —$(CH_2)_n$—SO—$(CH_2)_n$—, —$(CH_2)_n$—$SO_2$—$(CH_2)_n$—, or —$(CH_2)_n$—CH=CH—$(CH_2)_n$—O—;

$M^1$ is selected from the group of —COOH, —$(CH_2)_n$—COOH, —$(CH_2)_n$—C(O)—COOH, tetrazole,

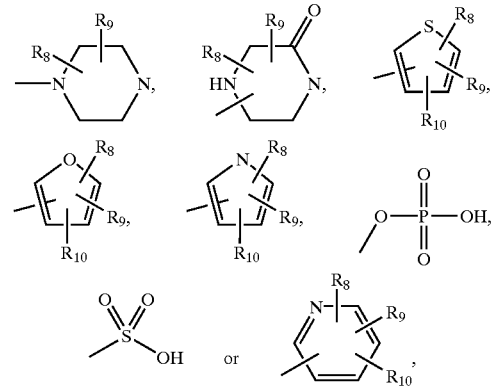

$L^2$ is a bridging or linking moiety selected from a chemical bond —$(CH_2)_n$—, —$(CH_2)_n$—C(O)—$(CH_2)_n$—, —$(CH_2)_n$—O—$(CH_2)_n$—,—$(CH_2)_n$—

S—(CH$_2$)$_n$—, —(CH$_2$)$_n$—SO—(CH$_2$)$_n$—, —(CH$_2$)$_n$—SO$_2$—(CH$_2$)$_n$—, or —(CH$_2$)$_n$—CH=CH—(CH$_2$)$_n$—O—; —C(Z)—N(R$_6$)—, —C(Z)—N(R$_6$)—(CH$_2$)$_n$—, —C(O)—C(Z)—N(R$_6$)—, —C(O)—C(Z)—N(R$_6$)—(CH$_2$)$_n$—, —C(Z)—NH—SO$_2$—, or —C(Z)—NH—SO$_2$—(CH$_2$)$_n$—;

M$^2$ is the moiety

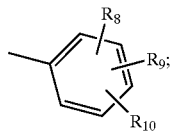

R$_8$, in each appearance, is independently selected from H, —COOH, —(CH$_2$)$_n$—COOH, —(CH$_2$)$_n$—C(O)—COOH, tetrazole, —C(O)—NH$_2$, —(CH$_2$)$_n$—C(O)—NH$_2$

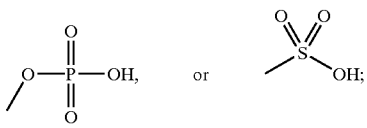

R$_9$, is selected from H, halogen, —CF$_3$, —OH, —COOH, —(CH$_2$)$_n$—COOH, —(CH$_2$)$_n$—C(O)—COOH, —C$_1$-C$_6$ alkyl, —O—C$_1$-C$_6$ alkyl, —NH(C$_1$-C$_6$ alkyl), —N(C$_1$-C$_6$ alkyl)$_2$;

R$_{10}$ is selected from the group of H, halogen, —CF$_3$, —OH, —COOH, —(CH$_2$)$_n$—COOH, —(CH$_2$)$_n$—C(O)—COOH, —C$_1$-C$_6$ alkyl, —O—C$_1$-C$_6$ alkyl, —NH(C$_1$-C$_6$ alkyl), —N(C$_1$-C$_6$ alkyl)$_2$,

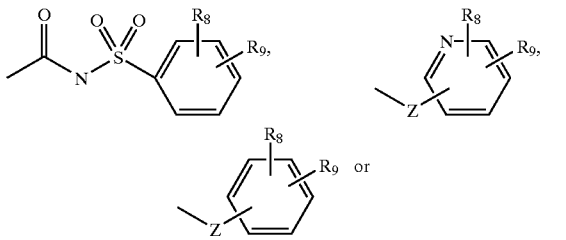

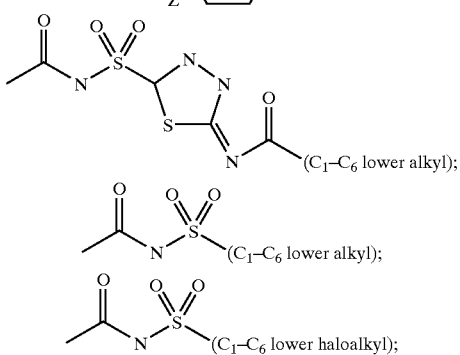

with a proviso that the complete moiety at the indole or indoline 3-position created by any combination of R$_3$, L$^1$, M$^1$, L$^2$, M$^2$, R$_8$, R$_9$, R$_{10}$, shall contain at least one acidic moiety selected from or containing a carboxylic acid, a tetrazole, or a moiety of the formulae: —C(O)—NH$_2$, —(CH$_2$)$_n$—C(O)—NH$_2$

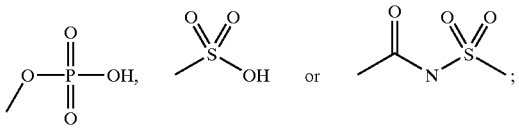

n is an integer from 0 to 3;

R$_4$ is selected from H, —CF$_3$, C$_1$-C$_6$ lower alkyl, C$_1$-C$_6$ lower alkoxy, C$_3$-C$_{10}$ cycloalkyl, —C$_1$-C$_6$ alkyl, —C$_3$-C$_{10}$ cycloalkyl, —CHO, halogen, (CH$_2$)$_n$C(O)NH$_2$, or a moiety of the formula —L$^3$—M$^3$:

L$^3$ indicates a linking or bridging group of the formulae —(CH$_2$)$_n$—, —C(O)—, —(CH$_2$)$_n$—C(O)—, —(CH$_2$)$_n$—C(O)—(CH$_2$)$_n$—, —(CH$_2$)$_n$—O—(CH$_2$)$_n$—, or —(CH$_2$)$_n$—S—(CH$_2$)$_n$—, C(O)C(O)X, —(CH$_2$)$_n$—N—(CH$_2$)$_n$;

M$^3$ is selected from:

a) H, the group of C$_1$-C$_6$ lower alkyl, C$_1$-C$_6$ lower alkoxy, C$_3$-C$_{10}$ cycloalkyl, phenyl or benzyl, the cycloalkyl, phenyl or benzyl rings being optionally substituted by from 1 to 3 substituents selected from halogen, C$_1$-C$_{10}$ alkyl, preferably C$_1$-C$_6$ alkyl, C$_1$-C$_{10}$ alkoxy, preferably C$_1$-C$_6$ alkoxy, —NO$_2$, —NH$_2$, —CN, or —CF$_3$; or R$_5$ is selected from the groups of:

a) a moiety of the formulae —(CH$_2$)$_n$—A, —(CH$_2$)$_n$—S—A, or —(CH$_2$)$_n$—O—A, wherein A is the moiety:

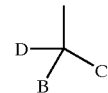

wherein

D is H, C$_1$-C$_6$ lower alkyl, C$_1$-C$_6$ lower alkoxy, —CF$_3$ or —(CH$_2$)$_n$—CF$_3$;

B and C are independently selected from phenyl, pyridinyl, pyrimidinyl, furyl, thienyl or pyrrolyl groups, each optionally substituted by from 1 to 3, preferably 1 to 2, substituents selected from H, halogen, —CF$_3$, —OH, —C$_1$-C$_6$ alkyl, C$_1$-C$_6$ alkoxy, —NH$_2$ or —NO$_2$;

or a pharmaceutically acceptable salt thereof.

Another preferred group of this invention are those of the formulae:

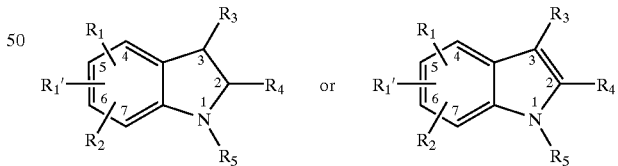

wherein:

R$_1$ and R$_{1'}$ are independently selected from H, halogen, —CF$_3$, —OH, —C$_1$-C$_{10}$ alkyl, preferably —C$_1$-C$_6$ alkyl, —S—C$_1$-C$_{10}$ alkyl, preferably —S—C$_1$-C$_6$ alkyl, C$_1$-C$_{10}$ alkoxy, preferably C$_1$-C$_6$ alkoxy, —CN, —NO$_2$, —NH$_2$, —HN(C$_1$-C$_6$), —N(C$_1$-C$_6$)$_2$, phenyl, —O-phenyl, —S-phenyl, benzyl, —O-benzyl, —S-benzyl, the phenyl and benzyl rings of these groups being optionally substituted by from 1 to 3 substituents selected from halogen, C$_1$-C$_6$ alkyl, C$_1$-C$_6$ alkoxy, —NO$_2$, —NH$_2$, —CN, —CF$_3$, or —OH;

$R_2$ is selected from H, halogen, —$CF_3$, —OH, —$C_1$-$C_{10}$ alkyl, preferably —$C_1$-$C_6$ alkyl, $C_1$-$C_{10}$ alkoxy, preferably $C_1$-$C_6$ alkoxy, —CHO, —CN, —$NO_2$, —$NH_2$, —NH—$C_1$-$C_6$ alkyl, —N($C_1$-$C_6$ alkyl)$_2$, —N—$SO_2$—$C_1$-$C_6$ alkyl, or —$SO_2$—$C_1$-$C_6$ alkyl;

$R_3$ is a moiety selected from the groups of:

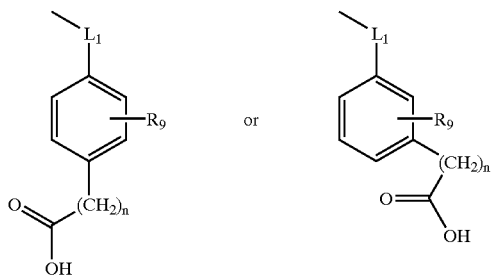

wherein $L^1$ is a bridging or linking moiety selected from a chemical bond, —$(CH_2)_{n'}$—, —$(CH_2)_{n'}$—C(O)—$(CH_2)_{n'}$—, —$(CH_2)_{n'}$—O—$(CH_2)_{n'}$—, —$(CH_2)_{n'}$—S—$(CH_2)_{n'}$—, —$(CH_2)_{n'}$—SO—$(CH_2)_{n'}$—, —$(CH_2)_{n'}$—$SO_2$—$(CH_2)_{n'}$—, or —$(CH_2)_{n'}$—CH=CH—$(CH_2)_{n'}$—O—;

where n' is an integer from 0 to 5;

$R_9$ is selected from halogen, —$CF_3$, —$C_1$-$C_6$ alkyl, $C_1$-$C_6$ alkoxy, —NH($C_1$-$C_6$ alkyl), or —N($C_1$-$C_6$ alkyl)$_2$, n in each instance is independently selected as an integer from 0 to 3;

$R_4$ is selected from H, —$C_1$-$C_{10}$ alkyl, preferably —$C_1$-$C_6$ alkyl, —$(CH_2)_n$—OH, $(CH_2)_nC(O)NH_2$, —$(CH_2)_n$—O—($C_1$-$C_6$ alkyl), —$(CH_2)_n$—O—$CH_2$-phenyl, —$(CH_2)_n$—N—($C_1$-$C_6$ alkyl), —$(CH_2)_n$—N—$CH_2$-phenyl, the phenyl rings of which are optionally substituted by 1 or 2 groups selected from H, halogen, —$CF_3$ or —$C_1$-$C_6$ alkyl;

n is an integer from 0–3

$R_5$ is selected from $C_1$-$C_6$ lower alkyl, $C_1$-$C_6$ lower alkoxy, —$(CH_2)_n$—$C_3$-$C_5$ cycloalkyl or —$(CH_2)_n$—A, —$(CH_2)_n$—S—A, or —$(CH_2)_n$—O—A wherein A is selected from:

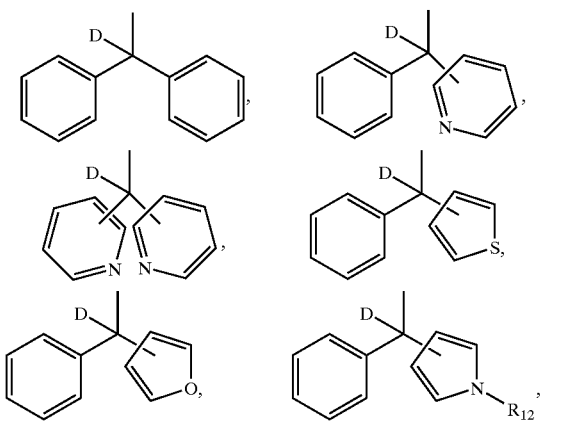

-continued

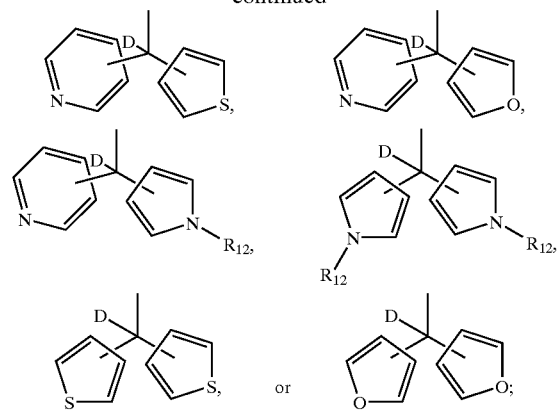

D is H, $C_1$-$C_6$ lower alkyl, $C_1$-$C_6$ lower alkoxy, or —$CF_3$;

$R_{12}$ is H, $C_1$-$C_6$ lower alkyl, $C_1$-$C_6$ lower alkoxy, or —$CF_3$;

or a pharmaceutically acceptable salt thereof.

The compounds of this invention have the following formulae:

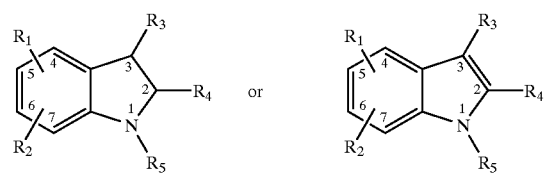

wherein:

$R_1$ is selected from H, halogen, —$CF_3$, —OH, —$C_1$-$C_{10}$ alkyl, preferably —$C_1$-$C_6$ alkyl, —S—$C_1$-$C_{10}$ alkyl, preferably —S—$C_1$-$C_6$ alkyl, $C_1$-$C_{10}$ alkoxy, preferably $C_1$-$C_6$ alkoxy, —CN, —$NO_2$, —$NH_2$, —HN($C_1$-$C_6$), —N($C_1$-$C_6$)$_2$, phenyl, —O-phenyl, —S-phenyl, benzyl, —O-benzyl, —S-benzyl, the phenyl and benzyl rings of these groups being optionally substituted by from 1 to 3 substituents selected from halogen, $C_1$-$C_6$ alkyl, $C_1$-$C_6$ alkoxy, —$NO_2$, —$NH_2$, —CN, —$CF_3$, or —OH;

$R_2$ is selected from H, halogen, —$CF_3$, —OH, —$C_1$-$C_{10}$ alkyl, preferably —$C_1$-$C_6$ alkyl, $C_1$-$C_{10}$ alkoxy, preferably $C_1$-$C_6$ alkoxy, —CHO, —CN, —$NO_2$, —$NH_2$, —NH—$C_1$-$C_6$ alkyl, —N($C_1$-$C_6$ alkyl)$_2$, —N—$SO_2$—$C_1$-$C_6$ alkyl, or —$SO_2$—$C_1$-$C_6$ alkyl;

$R_3$ is a moiety selected from the groups of:

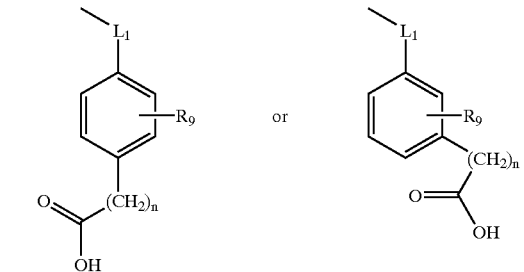

wherein $L^1$ is a bridging or linking moiety selected from a chemical bond, —$(CH_2)_{n'}$—, —$(CH_2)_{n'}$—C(O)—

—(CH$_2$)$_{n'}$—, —(CH$_2$)$_{n'}$—O—(CH$_2$)$_{n'}$—, —(CH$_2$)$_{n'}$—S—(CH$_2$)$_{n'}$—, —(CH$_2$)$_{n'}$—SO—(CH$_2$)$_{n'}$—, —(CH$_2$)$_{n'}$—SO$_2$—(CH$_2$)$_{n'}$—, or —(CH$_2$)$_{n'}$—CH=CH—(CH$_2$)$_{n'}$—O—;

where n' is an integer from 0 to 5;

R$_9$ is selected from halogen, —CF$_3$, —C$_1$-C$_6$ alkyl, C$_1$-C$_6$ alkoxy, —NH(C$_1$-C$_6$ alkyl), or —N(C$_1$-C$_6$ alkyl)$_2$, n in each instance is independently selected as an integer from 0 to 3 or a pharmaceutically acceptable salt thereof R$_4$ is selected from H, —C$_1$-C$_{10}$ alkyl, preferably —C$_1$-C$_6$ alkyl, —(CH$_2$)$_n$—OH, (CH$_2$)$_n$C(O)NH$_2$, —(CH$_2$)$_n$—O—(C$_1$-C$_6$ alkyl), —(CH$_2$)$_n$—O—CH$_2$-phenyl, —(CH$_2$)$_n$—N—(C$_1$-C$_6$ alkyl), —(CH$_2$)$_n$—N—CH$_2$-phenyl, the phenyl rings of which are optionally substituted by 1 or 2 groups selected from H, halogen, —CF$_3$ or —C$_1$-C$_6$ alkyl;

n is an integer from 0–3

R$_5$ is a moiety of the formulae —(CH$_2$)$_n$—A, —(CH$_2$)$_n$—S—A, or —(CH$_2$)$_n$—O—A, wherein A is the moiety:

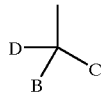

wherein

D is H, C$_1$-C$_6$ lower alkyl, C$_1$-C$_6$ lower alkoxy, or —CF$_3$;

B and C are independently selected from phenyl, pyridinyl, furyl, thienyl or pyrrolyl groups, each optionally substituted by from 1 to 3, preferably 1 to 2, substituents selected from H, halogen, —CF$_3$, —OH, —C$_1$-C$_6$ alkyl, C$_1$-C$_6$ alkoxy, or —NO$_2$;

or a pharmaceutically acceptable salt thereof.

Yet another preferred group herein are the compounds of the formulae:

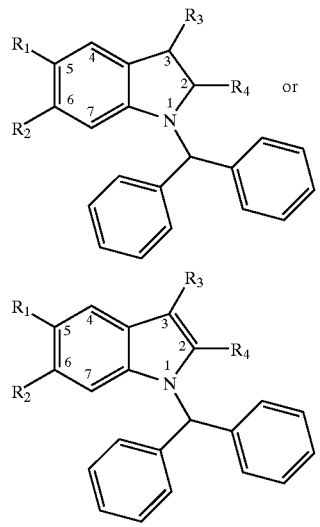

wherein:

R$_1$ is selected from H, halogen, —CF$_3$, —OH, —CN, —NO$_2$, —NH$_2$, —HN(C$_1$-C$_6$), —N(C$_1$-C$_6$)$_2$, phenyl, —N—SO$_2$—C$_1$-C$_6$ alkyl, or —SO$_2$—C$_1$-C$_6$ alkyl;

R$_2$ is selected from H, halogen, —CF$_3$, —OH, , —CN, —NO$_2$, —NH$_2$, —NH—C$_1$-C$_6$ alkyl, —N(C$_1$-C$_6$ alkyl)$_2$, —N—SO$_2$—C$_1$-C$_6$ alkyl, or —SO$_2$-C$_1$-C$_6$ alkyl;

R$_3$ is a moiety selected from the groups of:

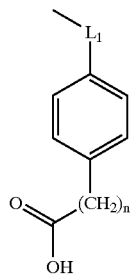 or 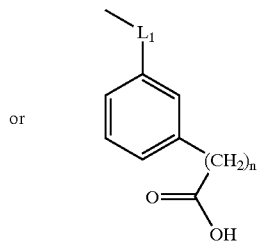

wherein

L$^1$ is a bridging or linking moiety selected from a chemical bond, —(CH$_2$)$_{n'}$—, —(CH$_2$)$_{n'}$—C(O)—(CH$_2$)$_{n'}$—, —(CH$_2$)$_{n'}$—O—(CH$_2$)$_{n'}$—,—(CH$_2$)$_{n'}$—S—(CH$_2$)$_{n'}$—, —(CH$_2$)$_{n'}$—SO—(CH$_2$)$_{n'}$—, —(CH$_2$)$_{n'}$—SO$_2$—(CH$_2$)$_{n'}$—, or —(CH$_2$)$_{n'}$—CH=CH—(CH$_2$)$_{n'}$—O—;

n' in each instance is independently selected as an integer from 0 to 5;

R$_4$ is selected from H, —C$_1$-C$_{10}$ alkyl, preferably —C$_1$-C$_6$ alkyl, —(CH$_2$)$_n$—OH, (CH$_2$)$_n$C(O)NH$_2$, —(CH$_2$)$_n$—O—(C$_1$-C$_6$ alkyl), —(CH$_2$)$_n$—O—CH$_2$-phenyl, —(CH$_2$)$_n$—N—(C$_1$-C$_6$ alkyl), —(CH$_2$)$_n$—N—CH$_2$-phenyl, the phenyl rings of which are optionally substituted by 1 or 2 groups selected from H, halogen, —CF$_3$ or —C$_1$-C$_6$ alkyl;

n is an integer from 0–3 or a pharmaceutically acceptable salt thereof.

DETAILED DESCRIPTION OF THE INVENTION

As used herein, the terms "aryl" and "substituted aryl" are understood to include monocyclic, particularly including five- and six-membered monocyclic, aromatic and heteroaromatic ring moieties and bicyclic aromatic and heteroaromatic ring moieties, particularly including those having from 9 to 10 ring atoms. Among these aryl groups are understood to be phenyl rings, including those found in phenoxy, benzyl, benzyloxy, biphenyl and other such moieties. The aryl and heteroaryl groups of this invention also include the following:

a) a five-membered heterocyclic ring containing one or two ring heteroatoms selected from N, S or O including, but not limited to, furan, pyrrole, thiophene, imidazole, pyrazole, isothiazole, isoxazole, pyrrolidine, pyrroline, imidazolidine, pyrazolidine, pyrazole, pyrazoline, imidazole, tetrazole, or oxathiazole; or b) a six-membered heterocyclic ring containing one, two or three ring heteroatoms selected from N, S or O including, but not limited to, pyran, pyridine, pyrazine, pyrimidine, pyridazine, piperidine, piperazine, tetrazine, thiazine, thiadizine, oxazine, or morpholine; or c) a bicyclic ring moiety optionally containing from 1 to 3 ring heteroatoms selected from N, S or O including, but not limited to benzofuran, chromene, indole, isoindole, indoline, isoindoline, napthalene, purine, indolizine, indazole, quinoline, isoquinoline, quinolizine, quinazoline, cinnoline, phthalazine, or napthyridine.

The "substituted aryl" groups of this invention include such aryl moieties being optionally substituted by from 1 to 3 substituents selected from halogen, $C_1$–$C_{10}$ alkyl, preferably $C_1$–$C_6$ alkyl, $C_1$–$C_{10}$ alkoxy, preferably $C_1$–$C_6$ alkoxy, —CHO, —COOH or esters thereof, —$NO_2$, —$NH_2$, —CN, —$CF_3$ or —OH or combinations thereof, such as —$CH_2CF_3$, —$NH(CH_3)$, etc.

The integers depicted by the variable n are in each appearance independently an integer from 0 to 3, preferably 0 to 2, more preferably 0 to 1. It will be understood the appearance of n in any instance is not definitive or limiting of the integer which may be indicated by n elsewhere within the definition of the present invention. For instance, each of the integers indicated by n in the moiety —$(CH_2)_n$—O—$(CH_2)_n$— may be selected from 0, 1, 2 or 3.

A preferred subset of these groups, optionally substituted as just described, include moieties formed from benzene, pyridine, napthylene or quinoline rings. A further preferred group includes those of furan, pyrrole, thiophene, pyrimidine, and morpholine rings. A preferred group of bicyclic aromatic groups includes benzofuran, indole, napthalene, and quinoline rings.

The alkyl, alkenyl and alkinyl groups referred to herein indicate such groups having from 1 to 10, preferably 1 to 6 carbon atoms, and may be straight, branched or cyclic. Unless indicated otherwise, it is preferred that these groups be straight or branched. Alkoxy groups herein indicate alkyl groups, as just defined, bridged to the relevant moiety by an oxygen atom.

Halogens herein are understood to include F, Cl, Br and I. As used herein, "phospholipase enzyme activity" means positive activity in an assay for metabolism of phospholipids (preferably one of the assays described in Example 116 below). A compound has "phospholipase enzyme inhibiting activity" when it inhibits the activity of a phospholipase (preferably $cPLA_2$) in any available assay (preferably an assay described below in Example 116 or Example 117) for enzyme activity. In preferred embodiments, a compound has (1) an $IC_{50}$ value of less than about 25 $\mu$M, preferably less than about 6 $\mu$M, in the LysoPC assay; (2) an $IC_{50}$ value of less than about 50 $\mu$M in the vesicle assay; (3) an $IC_{50}$ value of less than about 1 $\mu$M in the PMN assay; (4) an $IC_{50}$ value of less than about 15 $\mu$M in the Coumarine assay; and/or (5) measurable activity (preferably at least about 5% reduction in edema, more preferably at least about 10% reduction, more preferably at least about 15%, most preferably 20–30%) in the rat carrageenan—induced footpad edema test.

Compounds of the present invention are useful for inhibiting phospholipase enzyme (preferably $cPLA_2$) activity and, therefore, are useful in "treating" (i.e., treating, preventing or ameliorating) inflammatory or inflammation-related responses or conditions (e.g., rheumatoid arthritis, psoriasis, asthma, inflammatory bowel disease, and other diseases mediated by prostaglandins, leukotrienes or PAF) and other conditions, such as osteoporosis, colitis, myelogenous leukemia, diabetes, wasting and atherosclerosis.

The present invention encompasses both pharmaceutical compositions and therapeutic methods of treatment or use which employ compounds of the present invention.

Compounds of the present invention may be used in a pharmaceutical composition when combined with a pharmaceutically acceptable carrier. Such a composition may also contain (in addition to a compound or compounds of the present invention and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition may further contain other anti-inflammatory agents. Such additional factors and/or agents may be included in the pharmaceutical composition to produce a synergistic effect with compounds of the present invention, or to minimize side effects caused by the compound of the present invention.

The pharmaceutical composition of the invention may be in the form of a liposome in which compounds of the present invention are combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

As used herein, the terms "pharmaceutically effective amount" or "therapeutically effective amount" means the total amount of each active component of the pharmaceutical composition or method that is sufficient to show a meaningful patient benefit, i.e., treatment, healing, prevention or amelioration of an inflammatory response or condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of a compound of the present invention is administered to a mammal having a condition to be treated. Compounds of the present invention may be administered in accordance with the method of the invention either alone or in combination with other therapies such as treatments employing other anti-inflammatory agents, cytokines, lymphokines or other hematopoietic factors. When co-administered with one or more other anti-inflammatory agents, cytokines, lymphokines or other hematopoietic factors, compounds of the present invention may be administered either simultaneously with the other anti-inflammatory agent(s), cytokine(s), lymphokine(s), other hematopoietic factor(s), thrombolytic or anti-thrombotic factors, or sequentially. If administered sequentially, the attending physician will decide on the appropriate sequence of administering compounds of the present invention in combination with other anti-inflammatory agent(s), cytokine(s), lymphokine(s), other hematopoietic factor(s), thrombolytic or anti-thrombotic factors.

Administration of compounds of the present invention used in the pharmaceutical composition or to practice the method of the present invention can be carried out in a variety of conventional ways, such as oral ingestion, inhalation, or cutaneous, subcutaneous, or intravenous injection.

When a therapeutically effective amount of compounds of the present invention is administered orally, compounds of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% compound of the present invention, and preferably from about 25 to 90% compound of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of compound of the present invention, and preferably from about 1 to 50% compound of the present invention.

When a therapeutically effective amount of compounds of the present invention is administered by intravenous, cutaneous or subcutaneous injection, compounds of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to compounds of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of compound(s) of the present invention in the pharmaceutical composition of the present invention will depend upon the nature and severity of the condition being treated, and on the nature of prior treatments which the patient has undergone. Ultimately, the attending physician will decide the amount of compound of the present invention with which to treat each individual patient. Initially, the attending physician will administer low doses of compound of the present invention and observe the patient's response. Larger doses of compounds of the present invention may be administered until the optimal therapeutic effect is obtained for the patient, and at that point the dosage is not increased further. It is contemplated that the various pharmaceutical compositions used to practice the method of the present invention should contain about 0.1 $\mu$g to about 100 mg (preferably about 0.1 mg to about 50 mg, more preferably about 1 mg to about 2 mg) of compound of the present invention per kg body weight.

The duration of intravenous therapy using the pharmaceutical composition of the present invention will vary, depending on the severity of the disease being treated and the condition and potential idiosyncratic response of each individual patient. It is contemplated that the duration of each application of the compounds of the present invention will be in the range of 12 to 24 hours of continuous intravenous administration. Ultimately the attending physician will decide on the appropriate duration of intravenous therapy using the pharmaceutical composition of the present invention.

Compounds of the present invention invention can be made according to the methods and examples described below. Synthesis of preferred compounds of the present invention are described in the examples below.

Method A

The indole may be alkylated at the c-3 position with the appropriate alkyl bromide and treatment with a lewis acid such as silver(I)oxide or silver tetrafluoroborate in a solvent such as dioxane or THF at elevated temperatures of 50° C.–100° C. Alternatively it may be alkylated in a two step procedure by treatment of the indole with n-BuLi in a solvent such as THF or ether followed by ZnCl2 and then concentrated and treated with the appropriate alkylating agent in a variety of solvents such as THF, ether, toluene or benzene. The indole nitrogen may then be alkylated by treatment with a strong base such as sodium bis(trimethylsilyl)amide, n-BuLi, sodium hydride or potassium hydride in a solvent such as DMF, DMSO or THF followed by exposure to the appropriate alkyl halide. The ester can be hydrolyzed under basic conditions with sodium hydroxide in water and methanol and THF. Alternatively it may be cleaved by treatment with sodium thiomethoxide in a solvent such as THF or DMF at elevated temperatures (50° C.–100° C.). The product acid by be coupled to a sulfonamide by the agency of a variety of coupling reagents such as DCC, EDCI or carbonyl diimidazole in a solvent such as THF, methylene chloride, dichloroethane or DMF in the presence of a base such as triethyl amine and/or N, N-dimethyl pyridine. In the case of R1 =nitro the nitro group can be reduced by exposure to Pt/C in the presence of hydrogen in a solvent such as methanol, ethyl acetate or THF. The resulting amine can be acylated or sulfonylated by exposure to the appropriate agent in the presence of a base such as triethyl amine, sodium bicarbonate or pyridine in a biphasic solvent system such as methylene chloride:water (1:1) or THF:water (1:1) or a monophasic organic solvent such as methylene chloride, THF or DMF with triethylamine. The resulting acid may then be hydrolyzed and modified as described above. Also in the case R1=Br, it may be replaced with the copper salt of the desired nucleophile such as thiomethoxide, methoxide or sulphinic acid.

Method A

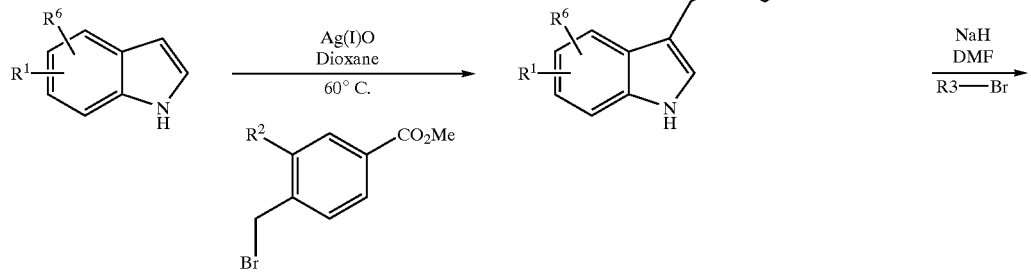

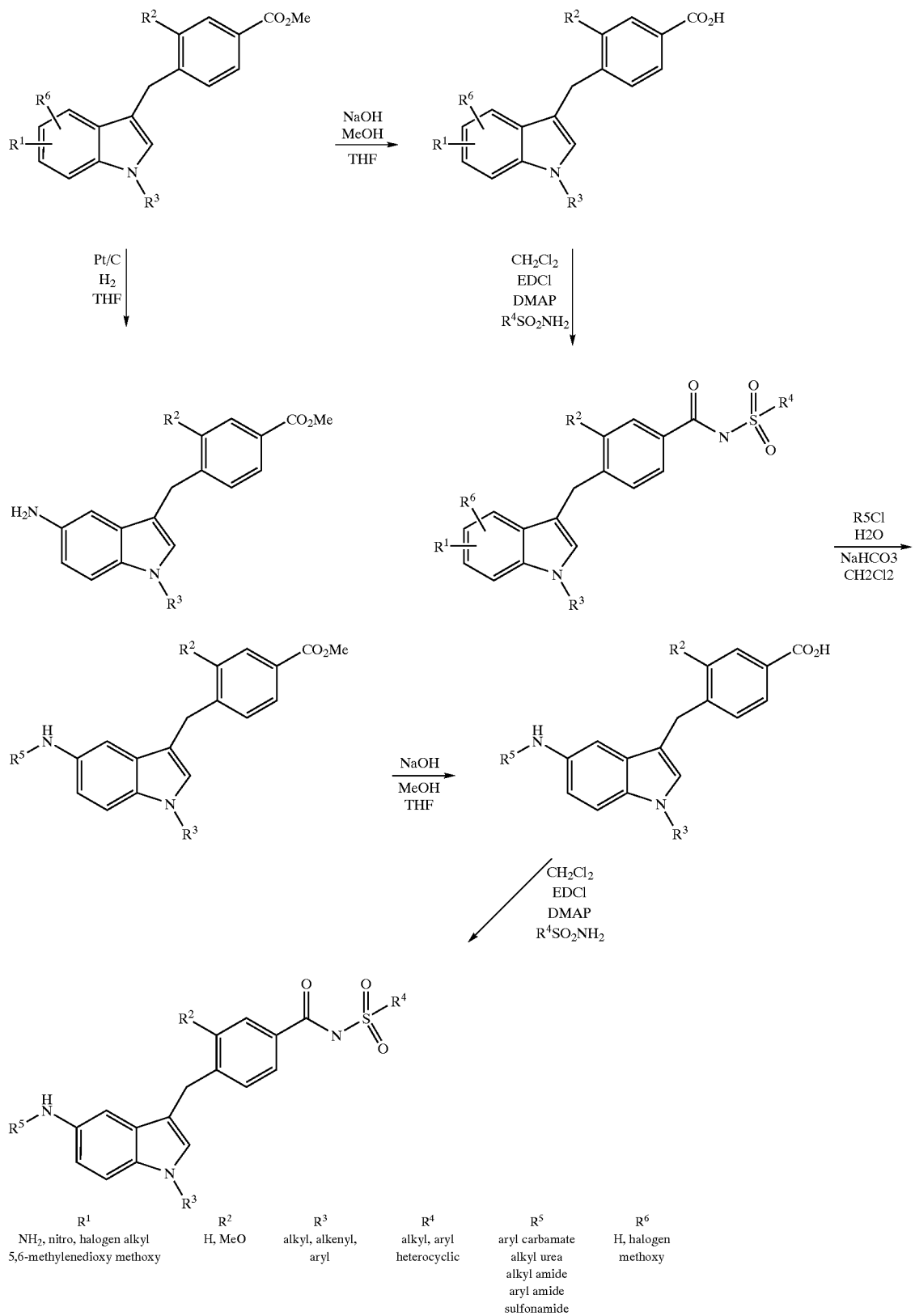

Method B

The indoleglyoxalyl chloride may be reacted with the desired amino ester in a biphasic system with methylene chloride and saturated sodium bicarbonate or in a monophasic system with a solvent such as methylene chloride, ethyl acetate or THF and a base such as triethylamine, Hunigs base or pyridine. The indole nitrogen may then be alkylated with a variety of alkylating reagents in a solvent such as DMF, DMSO or THF and a base such as sodium hydride, n-BuLi or potassium bis(trimethylsilyl)amide. The ester may then be hydrolyzed with sodium hydroxide or lithium hydroxide in a solvent system such as water:methanol:THF.

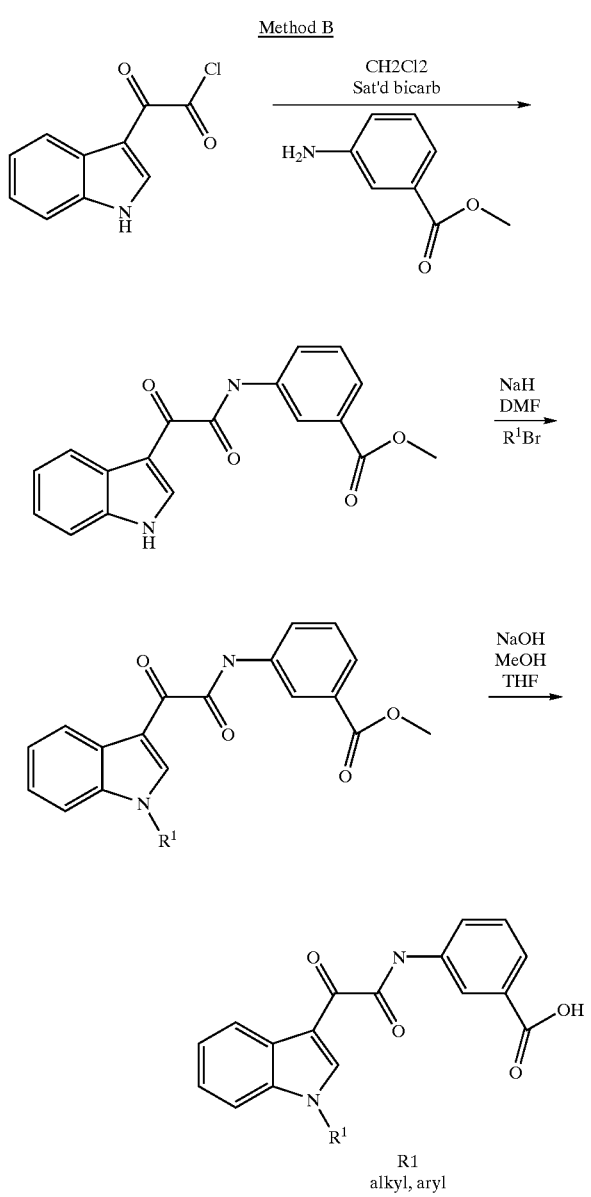

Method C

The 3-carboxyindole is elaborated via reductive amination by allowing the aldehyde to condense with an amino ester in a solvent such as methylene chloride or dichloromethane with or without acetic acid. The resulting imine is reduced in-situ with a reducing agent such as sodium borohydride, sodium cyanoborohydride or sodium triacetoxyborohydride. The acid is then prepared by hydrolysis of the resulting ester with sodium hydroxide or lithium hydroxide in a solvent system such as water:methanol:THF.

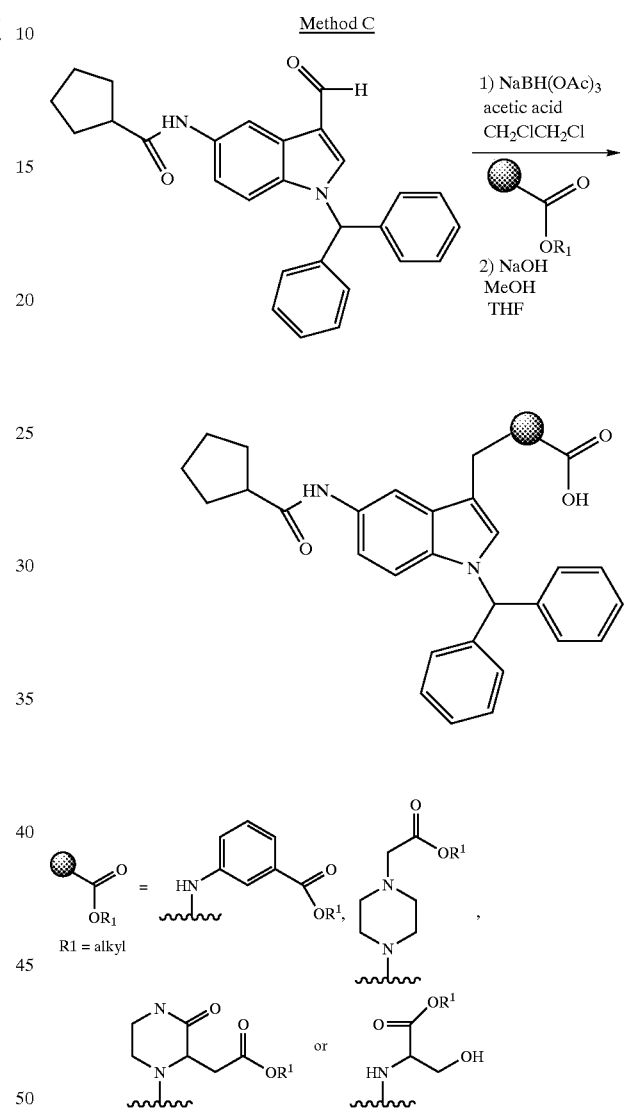

Method D 5-benzyloxyindole may be treated with a base such at methyl or ethyl grignard and acylated at the 3-position with ethyloxychloride in a suitable solvent such at ether or THF. The indole nitrogen may then be alkylated with a benzylbromide by the action of a base such as sodium hydride or n-butyllithium in a solvent such a THF or DMF. The ester is then hydrolysed under basic conditions with sodium hydroxide or tetrabutylammonium hydroxide in a suitable solvent system such at water:MeOH:THF. Coupling of the appropriate aminoester may then be effected by the use of a coupling agent such as DCC or EDCI in a solvent such as methylenechloride, TUF or DMW. The target acid may the be revealed by hydrolysis of the ester under the same conditions discussed above.

Method D
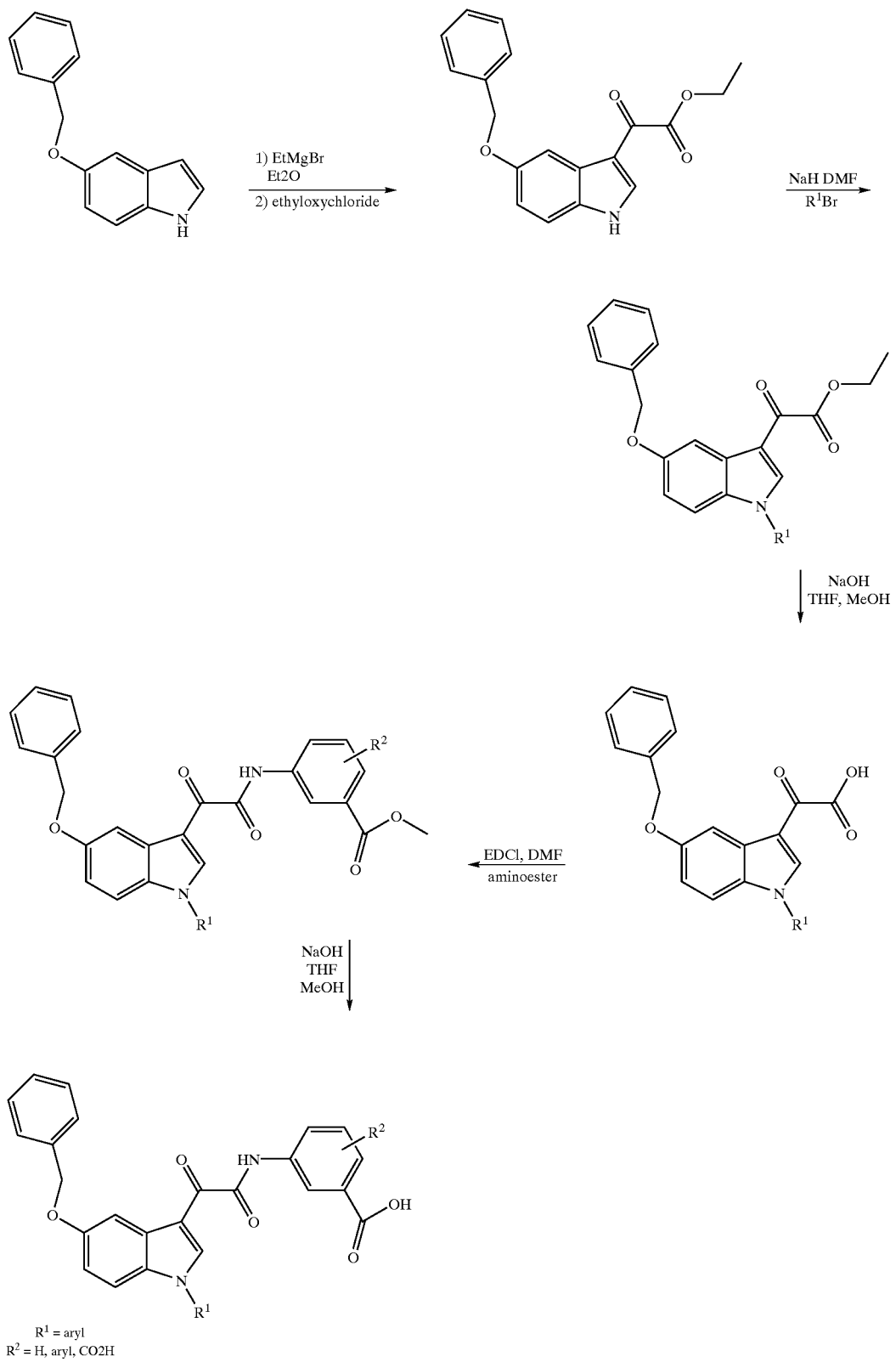
R[1] = aryl
R[2] = H, aryl, CO2H

Method E

Indole-3-acetic acid was alkylated with an appropriate alkyl bromide which was then subjected to Suzuki coupling conditions using Pd(PPh3)4 as a catalyst in a mixed solvent (ethanol-benzene-water) at elevated temperature to give the 1-alkyl-5-substituted indole.

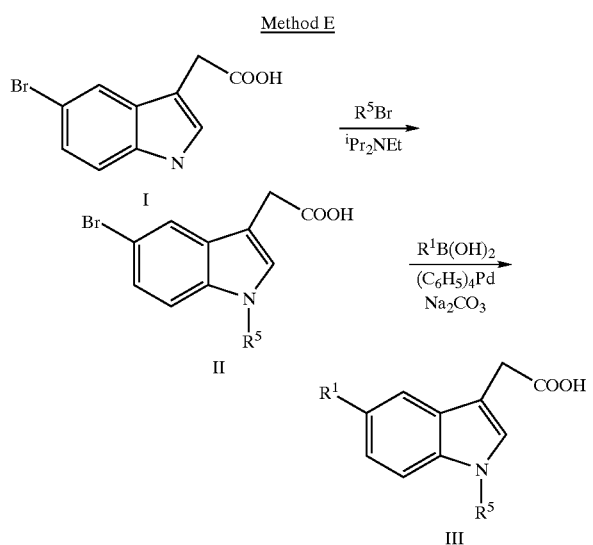

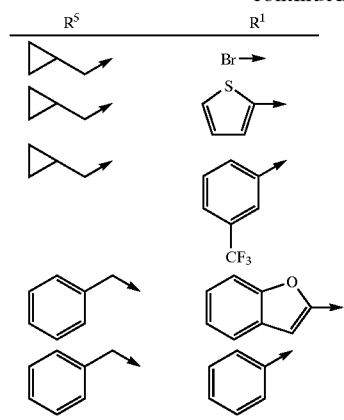

Method F

Alkylation of the nitrogen atom of I with a suitable base such a sodium hydride or potassium carbonate and an alkyl halide gave the aldehyde II. The aldehyde could be transformed to the thiazolidinedione III using a base such as piperdine and isolated with an acid such as acetic acid. Deprotonation with a suitable base such as sodium hydride and alkylation on the nitrogen atom of the thiazolidinedione with selected electrophiles such as alkyl or benzyl halides provided compounds such as IV.

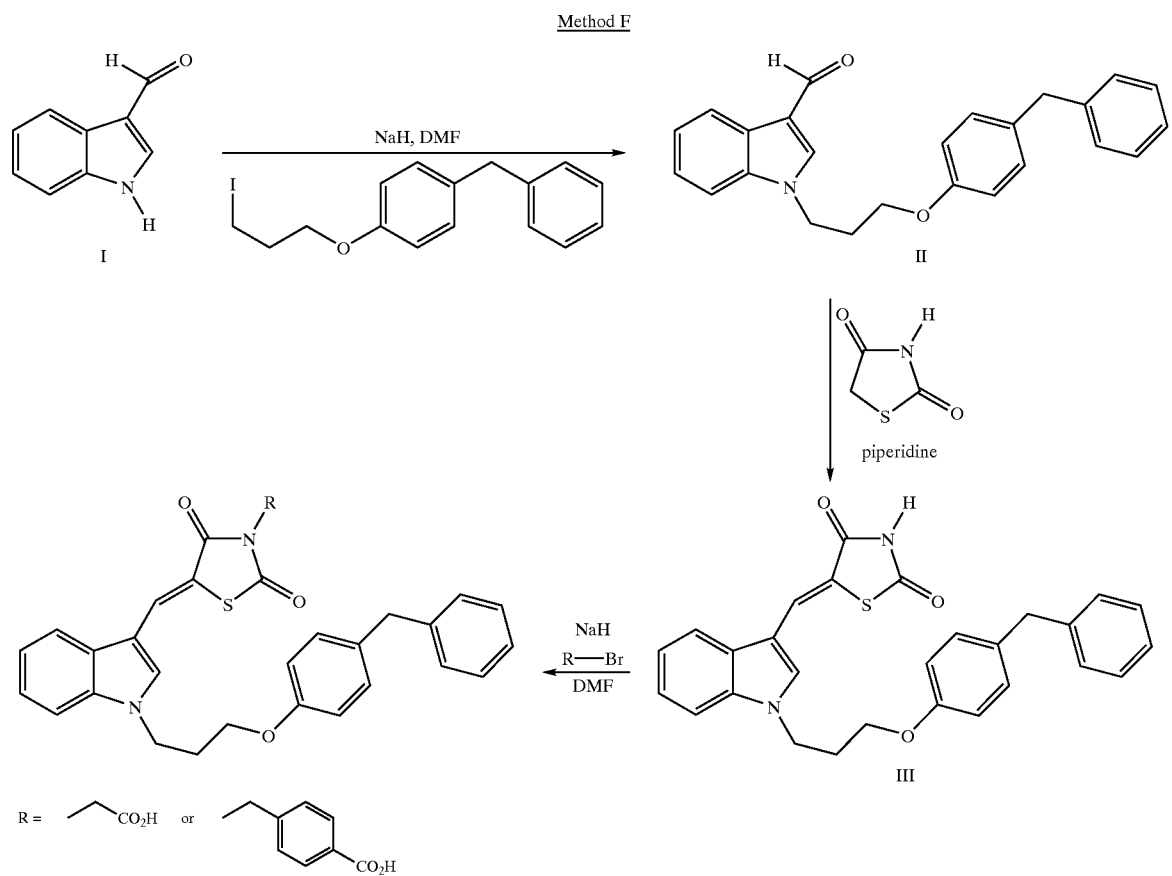

Method G

The nitro-indole I was converted to the unsaturated ester via a Horner-Wittig reaction with trimethoxyphosphonoacetate in a suitable solvent such as tetrahydrofuran. Reduction of the nitro group of II can be accomplished via hydrogenation with palladium on carbon in the presence of hydrogen and acylation of the resulting amine under Schotten-Bowmann conditions to give amides such as III. Saponification of the ester function gave the acid-indole IV.

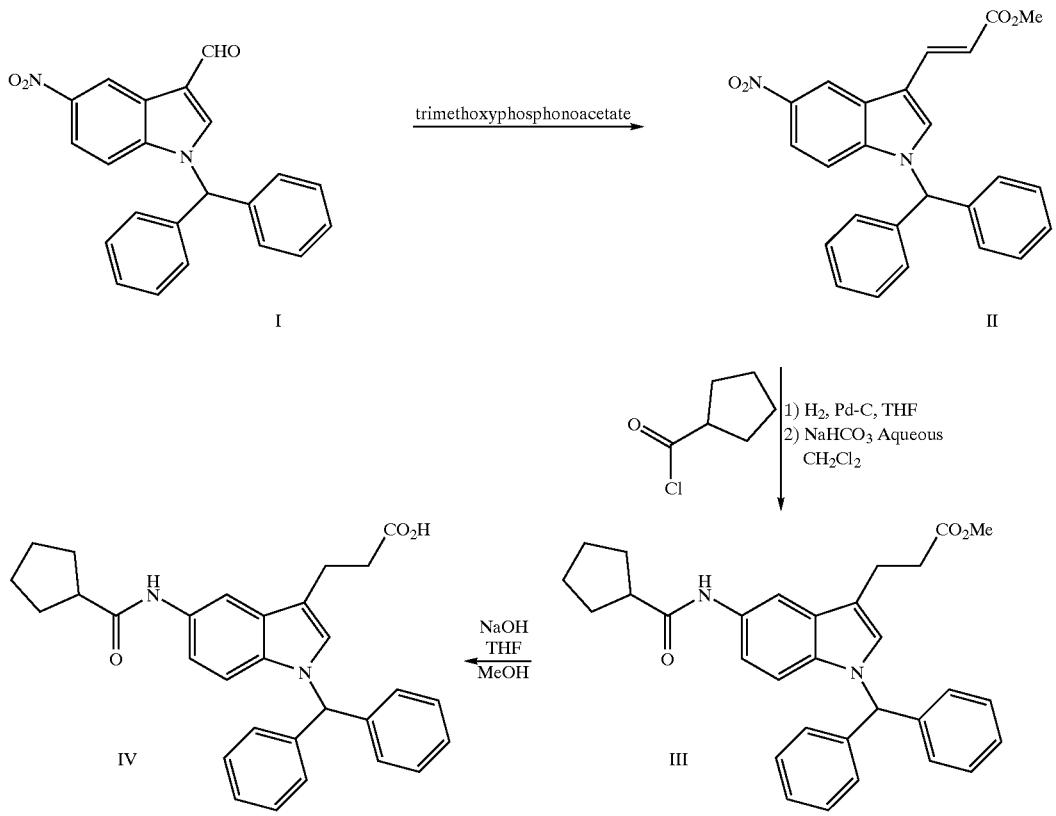

Method H

5-Chloro-2-methylindole could be reductively alkylated at the 3-position with a suitable aldehyde in the presence of an acid such as trifluoroacetic acid and a reducing agent such as triethylsilane in a suitable solvent such as methylene chloride to give the ester II. The nitrogen atom could be alkylated by treatment with a suitable base such as sodium hydride and diphenyl bromo methane and the resulting compound III could be saponified to give IV.

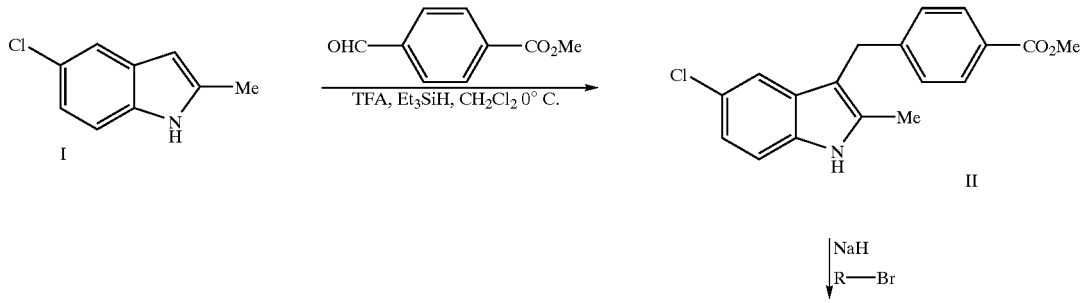

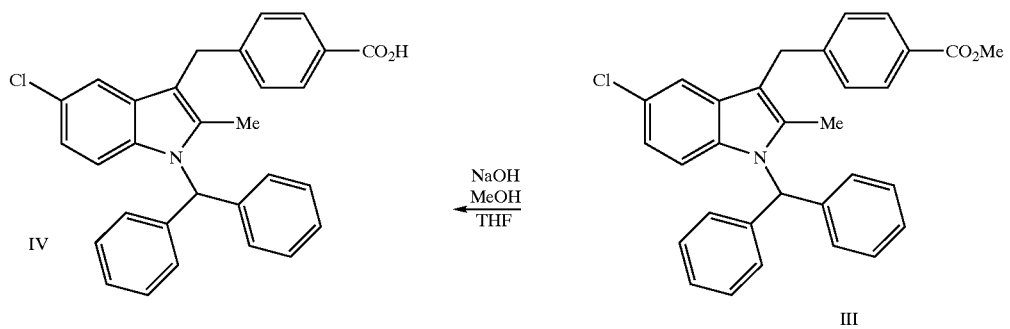

Method I

The starting indole is C3 functionalized by either reaction of DMF/POCl3 or by reacting the magnesium salt of the indole with methyl oxalyl chloride. The resulting esters and aldehydes were then N-alkylated by treating the salt of the indole, generated by treating the indole with a strong base, with a variety of alkyl halides. In th case of the aldehydes, when r' is a nitro group, the nitro is reduced to the amine using Pt/C and H2 or copper acetate/sodium borohydride and then acylated using various acid chlorides, isocyanates, chloroformates or reductively alkylated using aldehydes and sodium triacetoxyborohydride. These aldehydes could then be oxidised to the desired acid which could be coupled to an amino alkyl or aryl esters by an EDCI coupling method or by first transforming the acid into the acid chloride under the action of oxalyl chloride and the reacting this with an amino alkyl or aryl ester. These were then hydrolyzed to yield the final product. The esters generated above could be treated in a similar fashion. The ester could hydrolyzed and then coupled to an amino alkyl or aryl esters by an EDCI coupling method or by first transforming the acid into the acid chloride under the action of oxalyl chloride and the reacting this with an amino alkyl or aryl ester. These were then hydrolyzed to yield the final product.

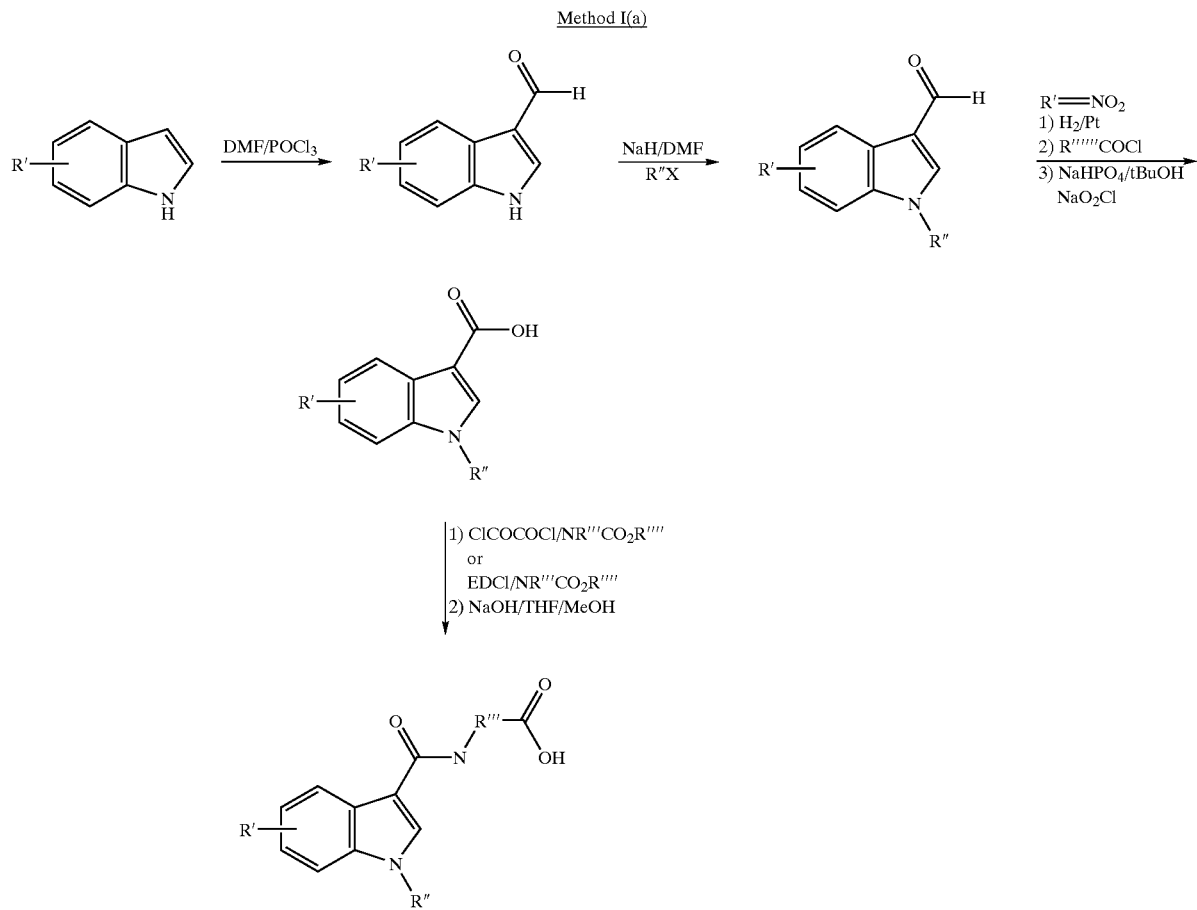

Method I(b)
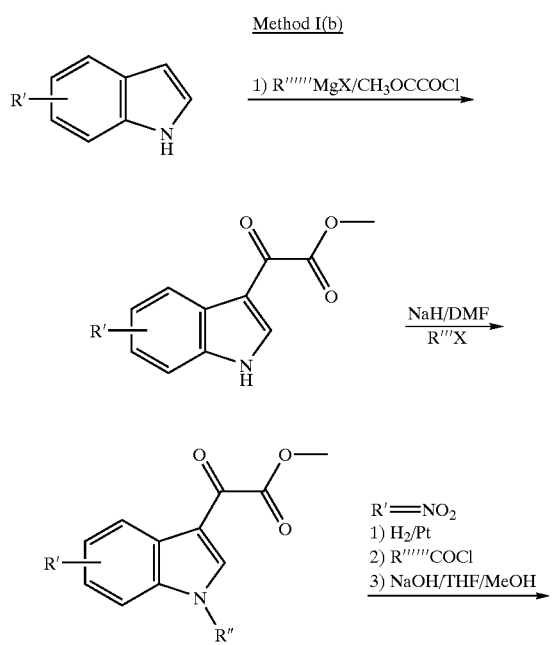
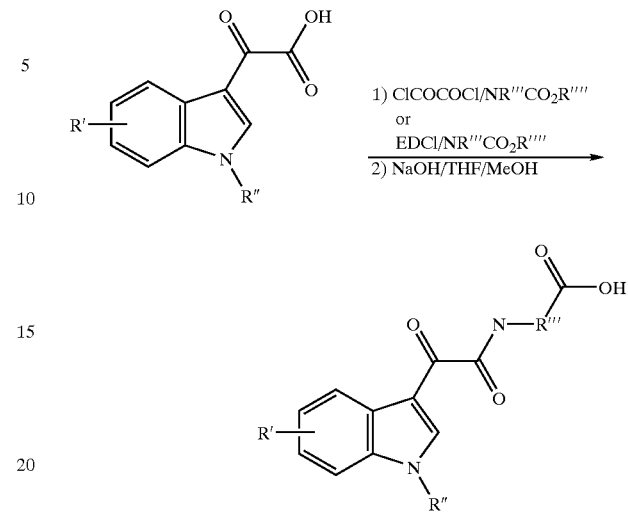
Method J
The starting amine was treated with various sulfonyl chlorides in the presence of pyridiine and then the excess sulfonylchloride was scavenged by adding a polymer bound amine. The desired products where then hydrolyzed using sodium hydroxide in THF/MeOH and the reaction was aidified using IR-120 resin to yield the desired products.
Method J
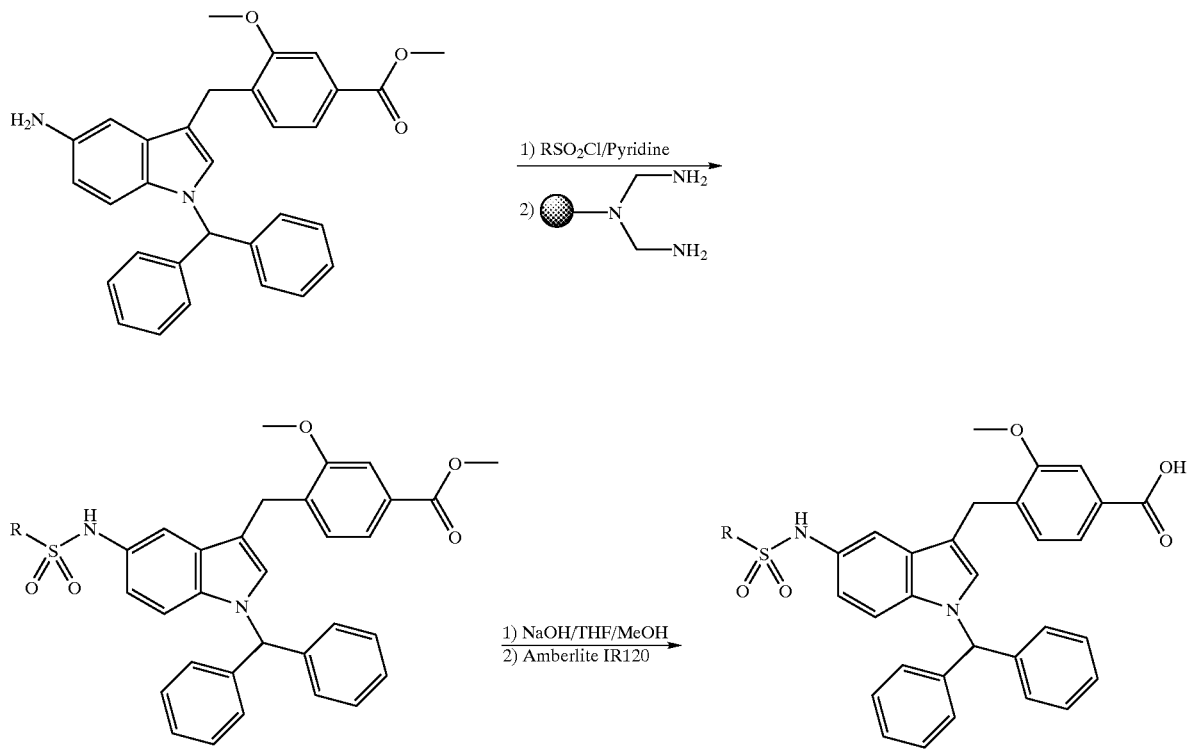

Method K

The starting indole was bis alkylated by the addition of a strong base such as sodium hydride and then an alkylating agent such as an alkyl or aryl halide followed by the hydrolysis of the resulting ester with sodium hydroxide in THF/MeOH. The acid was then coupled with an alkyl or aryl amino ester and then hydrolyzed to yield the desired acid.

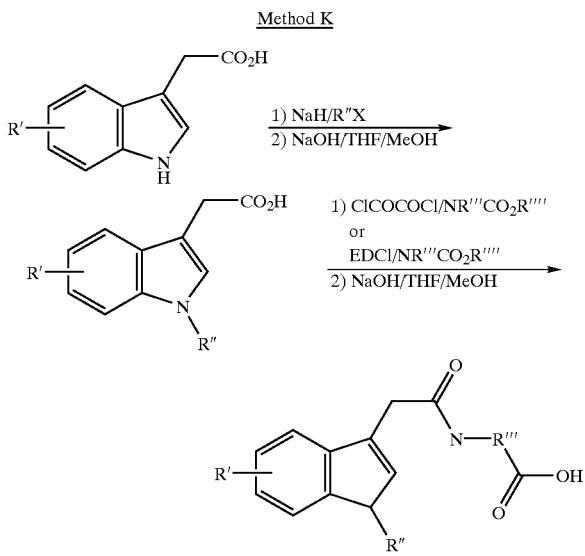

EXAMPLE 1

4-[(5-{[(cyclopentyloxy)carbonyl]amino}-1-propyl-1H-indol-3-yl)methyl]-3-methoxybenzoic acid Step 1—To a solution of 5-nitro indole (21.24 g, 131 mmol) in dioxane (128 mL) in a reaction vessel wrapped in aluminum foil is added silver(I)oxide (30.34 g, 131 mmoL, 1.5 eq) and methyl 4-(bromomethyl)-3-methoxy-benzoate (34 g, 131 mmol) and the mixture is brought to 60° C. and stirred 20 h. The reaction is cooled, filtered through celite, taken up in ethyl acetate (500 mL), washed with brine (2×50 mL), dried (MgSO,) and filtered. The crude material was purified by silica chromatography (15% ethyl acetate/hexanes) to afford the desired product (5.8 g, 55%).

Step 2—The C3-alkylated indole (1.5 g, 4.4 mmol) was dissolved with 15 mL THF. In a separate flask, NaH (185 g, 4.61 mmol) was suspended with 25 mL THF at 0° C. The solution of starting material was cannulated into the NaH suspension, giving a deep red solution. This was then allowed to stir at room temperature for 10 minutes. 1-iodopropane was added (0.47 mL, 1.1 mmol) and the reaction was allowed to pr°ceed overnight at room temperature. As the reaction was not complete (TLC) and additional 0.5 mL of 1-iodopropane was added and the reaction continued for another 3 h. There was no change in the TLC and the reaction was poured into cold 1 N HCl and extracted with $CH_2Cl_2$ (3×75 mL). The combined organic layers were dried over $MgSO_4$, filtered and evaporated to yield the crude N-alkylated nitroindole. The crude material was absorbed onto silica and loaded onto a silica gel column. The column was eluted with 100% $CH_2Cl_2$ to give the pure yellow N-alkylated nitroindole (0.96 g, 57%).

Step 3—The N-alkylated nitroindole (0.95 g) was dissolved with 40 mL anhydrous THF. The system was purged with argon. To the clear, yellow solution, Pt/C (0.462 g) was added. The argon was then removed by evacuation and hydrogen was introduced to the system. The reaction was stirred 6.5 h. The hydrogen was evacuated and argon was then purged through the system. The reaction mixture was filtered through celite with THF. The solvent was removed by rotary evaporation to give the crude amine as a dark oil. Chromatography (5% ethyl acetate/$CH_2Cl_2$) afforded the desired product (0.7 g, 80%)

Step 4—The amine from above (0.7 g) was dissolved in 40 mL $CH_2Cl_2$. 4-methylmorpholine (0.3 mL, 3.0 mmol) and cyclopentyl chloroformate (383 mg, 2.57 mmol) were then added to give a yellow/orange solution. The reaction was allowed to proceed at room temperature for 3 h. The reaction mixture was acidified with 1 N HCl and the mixture was extracted with 50 mL $CH_2Cl_2$. The combined organic phases were washed with brine, dried over $MgSO_4$, filtered and concentrated to give the crude carbamate. The crude product was absorbed onto silica gel and loaded onto a silica gel column. The column was eluted with 100% $CH_2C_2$ to afford the desired product (0.87 g, 39%) as a yellow foam.

Step 5—The carbamate (0.831 g) was dissolved with hydrolysis solution (2:1:1 THF:MeOH:2N NaOH) and the reaction was allowed to proceed for 5.25 h. The reaction was acidified to pH 2 with 2N HCl and extracted with $CH_2Cl_2$. The organic layer was washed with water and brine. The combined organic layers were then dried over $MgSO_4$, filtered and evaporated to yield the crude acid, which was recrystallized from $CH_2Cl_2$ to afford the title compound (0.575 g, 71%) as pink crystals. MS: m/z (M−1) 449

EXAMPLE 2

Cyclopentyl N-{3-[2-methoxy-4-({[(2-methylphenyl)sulfonyl]amino}carbonyl)benzyl]-1-propyl-1H-indol-5-yl}carbamate Step 1—The intermediate 5-nitro indole is prepared as in Example 1, step 2, using the appropriate alkylating agent.

Step 2—The intermediate 5-amino indole is prepared as in Example 1, step 3, using the above intermediate.

Step 3—The intermediate carbamate is prepared as in Example 1, step 4, using the appropriate acylating agent.

Step 4—The title compound is prepared as in Example 1, step 5, using the above intermediate.

EXAMPLE 3

4-[(1-benzhydryl-5-{[(cyclopentyloxy)carbonyl]amino}1H-indol-3-yl)methyl]-3-methoxybenzoic acid Step 1—The intermediate 5-nitro indole is prepared as in Example 1, step 2, using the appropriate alkylating agent.

Step 2—The intermediate 5-amino indole is prepared as in Example 1, step 3, using the above intermediate.

Step 3—The intermediate carbamate is prepared as in Example 1, step 4, using the appropriate acylating agent.

Step 4—The title compound is prepared as in Example 1, step 5, using the above intermediate.

EXAMPLE 4

4-{[5-{[(cyclopentyloxy)carbonyl]amino}-1-(2-naphthylmethyl)-1H-indol-3-yl]methyl}3-methoxybenzoic acid Step 1—The intermediate 5-nitro indole is prepared as in Example 1, step 2, using the appropriate alkylating agent.

Step 2—The intermediate 5-amino indole is prepared as in Example 1, step 3, using the above intermediate.

Step 3—The intermediate carbamate is prepared as in Example 1, step 4, using the appropriate acylating agent.

Step 4—The title compound is prepared as in Example 1, step 5, using the above intermediate. MS: m/z (M−1) 547

EXAMPLE 5

4-{[5-{[(cyclopentyloxy)carbonyl]aminol}-1-(cyclopropylmethyl)-1H-indol-3-yl]methyl}-3-methoxybenzoic acid Step 1—The intermediate 5-nitro indole is prepared as in Example 1, step 2, using the appropriate alkylating agent.

Step 2—The intermediate 5-amino indole is prepared as in Example 1, step 3, using the above intermediate.

Step 3—The intermediate carbamate is prepared as in Example 1, step 4, using the appropriate acylating agent.

Step 4—The title compound is prepared as in Example 1, step 5, using the above intermediate. MS: m/z (M−1) 461

EXAMPLE 6

4-{[5-{[(cyclopentyloxy)carbonyl]amino}-1-(4-pyridinylmethyl)-1H-indol-3-yl]methyl}-3-methoxybenzoic acid Step 1—The intermediate 5-nitro indole is prepared as in Example 1, step 2, using the appropriate alkylating agent.

Step 2—The intermediate 5-amino indole is prepared as in Example 1, step 3, using the above intermediate.

Step 3—The intermediate carbamate is prepared as in Example 1, step 4, using the appropriate acylating agent.

Step 4—The title compound is prepared as in Example 1, step 5, using the above intermediate.

EXAMPLE 7

4-[(5-{[(cylopentyloxy)carbonyl]amino}-1-isopropyl-1H-indol-3yl)methyl]-3-methoxybenzoic acid Step 1—The intermediate 5-nitro indole is prepared as in Example 1, step 2, using the appropriate alkylating agent.

Step 2—The intermediate 5-amino indole is prepared as in Example 1, step 3, using the above intermediate.

Step 3—The intermediate carbamate is prepared as in Example 1, step 4, using the appropriate acylating agent.

Step 4—The title compound is prepared as in Example 1, step 5, using the above intermediate. MS: m/z (M−1) 449

EXAMPLE 8

4-[(1-cyclopentyl-5-{[(cyclopentyloxy)carbonyl]amino}-1H-indol-3-yl)methyl]-3-methoxybenzoicacid Step 1—The intermediate 5-nitro indole is prepared as in Example 1, step 2, using the appropriate alkylating agent.

Step 2 The intermediate 5-amino indole is prepared as in Example 1, step 3, using the above intermediate.

Step 3 The intermediate carbamate is prepared as in Example 1, step 4, using the appropriate acylating agent.

Step 4 The title compound is prepared as in Example 1, step 5, using the above intermediate. MS: m/z (M−1) 475

EXAMPLE 9

4[(1-benzhydryl-5-{[(butylamino)carbonyl]amino}-1H-indol-3-yl)methyl]3-methoxybenzoic acid The intermediate 5-nitro indole is prepared as in Example 1, step 2, using the appropriate alkylating agent and the intermediate 5-amino indole is prepared as in Example 1, step 3, using the 5-nitro indole intermediate. The intermediate urea is prepared as in Example 1, step 4, using the appropriate acylating agent. The title compound is prepared as in Example 1, step 5, using the urea intermediate. MS: m/z (M−1) 560

EXAMPLE 10

4-({1-benzhydryl-5-[(methylsulfonyl)amino]-1H-indol-3-yl}methyl)-3-methoxybenzoic acid The intermediate 5-nitro indole is prepared as in Example 1, step 2, using the appropriate alkylating agent followed by preparation of the intermediate 5-amino indole as in Example 1, step 3, using the 5-nitro indole. The intermediate sulfonamide is next prepared as in Example 1, step 4, using the appropriate acylating agent. The title compound is then prepared as in Example 1, step 5, using the sulfonamide intermediate. MS: m/z (M−1) 539

EXAMPLE 11

4-({1-benzhydryl-5-[(cyclopentylcarbonyl)amino]-1H-indol-3-yl}methyl)-3-methoxybenzoic acid The intermediate 5-nitro indole is prepared as in Example 1, step 2, using the appropriate alkylating agent and intermediate 5-amino indole is prepared as in Example 1, step 3, using this 5-nitro indole intermediate. The corresponding intermediate amide is then prepared as in Example 1, step 4, using the appropriate acylating agent. The final title compound is prepared as in Example 1, step 5, using this amide intermediate. MS: m/z (M−1) 557

EXAMPLE 12

4-[(1-benzhydryl-5-nitro-1H-indol-3-yl)methyl]3-methoxybenzoic acid

The intermediate 5-nitro indole is prepared as in Example 1, step 2, using the appropriate alkylating agent and the title compound is prepared as in Example 1, step 5, using this intermediate. MS: m/z (M−1) 657

EXAMPLE 13

4-[(1-benzhydryl-5-bromo-1H-indol-3-yl)methyl]-3-methoxybenzoic acid

The intermediate 5—bromo indole is prepared as in Example 1, step 1, using the appropriate indole and as in Example 1, step 2, using the appropriate alkylating agent. The title compound is then prepared as in Example 1, step 5, using the above intermediate. MS: m/z (M−1) 526

EXAMPLE 14

4-[(1-benzhydryl-5-fluoro-1H-indol-3-yl)methyl]-3-methoxybenzoic acid

The intermediate 5—fluoro indole is prepared as in Example 1, step 1, using the appropriate indole and as in Example 1, step 2, using the appropriate alkylating agent. The title compound is prepared as in Example 1, step 5, using the above intermediate. MS: m/z (M−1) 464

EXAMPLE 15

4-[(1-benzhydryl-5-methyl-1H-indol-3-yl)methyl]-3-methoxybenzoic acid

The intermediate 5—methyl indole is prepared as in Example 1, step 1, using the appropriate indole and as in Example 1, step 2, using the appropriate alkylating agent. The title compound is then prepared as in Example 1, step 5, using the above intermediate. MS: m/z (M−1) 460

EXAMPLE 16

4-[(5-benzhydryl-5H-[1,3]dioxolo[4,5-f]indol-7-yl)methyl]-3-methoxybenzoic acid

The intermediate 5,6-methylenedioxy indole is prepared as in Example 1, step 1, using the appropriate indole and as in Example 1, step 2, using the appropriate alkylating agent. The title compound is then prepared as in Example 1, step 5, using the above intermediate. MS: m/z (M−1) 490

EXAMPLE 17

4-[(1-benzhydryl-5-cyano-1H-indol-3-yl)methyl]-3-methoxybenzoic acid

Step 1 To the intermediate from Example 13, step 2 (0.25 g, 0.46 mmol), in DMF (1 mL) is added CuCN (0.05 g, 1.2 eq) and the reaction mixture is stirred at 145° C. overnight and then cooled. To the cooled reaction mixture is added $FeCl_3$ (0.09 g, 1.2 eq). The reaction mixture is stirred 5 min, taken up in ethyl acetate (30 mL), washed with brine (3×10 mL), dried ($MgSO_4$), filtered and concentrated. The product was purified by silica chromatography (20% ethyl acetate/hexanes) to afford the intermediate ester (0.2 g, 89%) as a colorless oil.

Step 2 To the intermediate ester (0.2 0.41 mmol) in DMF (2 mL) is added sodium thiomethoxide (0.1 g, 3.4 eq) and the reaction mixture is stirred at 90° C. for 10 min. The reaction is cooled, poured into ethyl acetate (5 mL), washed with sodium biphosphate (1×2 mL), brine (2×2 mL), dried ($MgSO_4$), filtered and concentrated. Purification by silica chromatography (1% acetic acid, 25% ethyl acetate/hexanes) afforded the title compound (0.114 g, 59%) as a colorless amorphous powder. MS: m/z (M−1) 471

EXAMPLE 18

4-{[1-benzhydryl-5-(methylsulfonyl)-1H-indol-3-yl]methyl}-3-methoxybenzoic acid

Step 1 To the intermediate from Example 13, step 3 (1 g, 1.9 mmol), in a solution of THF (2 mL) and methanol (2 mL) is added sodium hydroxide (0.41 mL, 4.63 M, 1 eq). The mixture is stirred for 20 min and then concentrated. The residual water is chased off by the addition of toluene and it's removal (3×) a white powder (1 g, 100%).

Step 2 To the sodium salt prepared above (0.88 g, 1.6 mmol) in DMF (3 mL) is added methanesulfinic acid, sodium salt (0.72 g, 4.4 eq) and CuI (0.74 g, 2.4 eq). The reaction mixture is stirred at 130° C. overnight, cooled, taken up in ethyl acetate (50 mL) and acetic acid (10 mL), filtered (celite), washed with brine (4×10 mL), dried ($MgSO_4$), filtered and concentrated. Silica chromatography (1% acetic acid, 25% ethyl acetate/hexanes-1% acetic acid, 50% ethyl acetate/hexanes) afforded the title compound (0.2 g, 24%) as a colorless amorphous solid. MS: m/z (M−1) 524

EXAMPLE 19

Cyclopentyl N-{1-benzhydryl-3-[2-methoxy-4-({[(2-methylphenyl)sulfonyl]amino}carbonyl)benzyl]-1H-indol-5-yl}carbamate To the product of Example 3, step 4 (0.5 g, 0.87 mmol), in $CH_2Cl_2$ (4 mL) is added EDCI (0.2 g, 1.0 mmol, 1.2 eq), DMAP (0.011 g, 0.087 mmol, 0.1 eq) and ortho-toluene sulfonamide. The reaction is stirred overnight at room temperature, taken up in ethyl acetate (50 mL), washed with sodium biphosphate (1×10 mL), brine (2×10 mL), dried ($MgSO_4$), filtered a acid, 25% ethyl acetate/hexanes) afforded the title compound (0.4 g, 63%) as a colorless solid.

EXAMPLE 20

Cyclopentyl N-{3-[2-methoxy-4-({[(2-methylphenyl)sulfonyl]amino}carbonyl)benzyl]-1-propyl-1H-indol-5-yl}carbamate The title compound is prepared as illustrated in Example 19 starting with the product of Example 1, step 5, and the appropriate sulfonamide.

EXAMPLE 21

Cyclopentyl N-{1-(cyclopropylmethyl)-3-[2-methoxy-4-({[(2-methylphenyl)sulfonyl]amino}carbonyl)benzyl]-1H-indol-5-yl}carbamate The title compound is prepared as illustrated in Example 19 starting with the product of Example 5, step 4, and the appropriate sulfonamide. MS: m/z (M−1) 614

EXAMPLE 22

Cyclopentyl N-[3-2-methoxy-4-({[(2-methylphenyl)sulfonyl]amino}carbonyl)benzyl]-1-(4-pyridinylmethyl)-1H-indol-5-yl]carbamate The title compound is prepared as illustrated in Example 19 starting with the product of Example 6, step 4, and the appropriate sulfonamide. MS: m/z (M−1) 651

EXAMPLE 23

Cyclopentyl N-[3-[2-methoxy-4-({[(2-methylphenyl)sulfonyl]amino}carbonyl)benzyl]-1-(2-naphthylmethyl)-1H-indol-5-yl]carbamate The title compound is prepared as illustrated in Example 19 starting with the product of Example 4, step 4, and the appropriate sulfonamide. MS: m/z (M−1) 700

EXAMPLE 24

Cyclopentyl N-{1-isopropyl-3-[2-methoxy-4-({[(2-methylphenyl)sulfonyl]amino}carbonyl)benzyl]-1H-indol-5-yl}carbamate The title compound is prepared as illustrated in Example 19 starting with the product of Example 7, step 4, and the appropriate sulfonamide. MS: m/z (M−1) 602

EXAMPLE 25

Cyclopentyl N-{1-cyclopentyl-3-[2-methoxy-4-({[(2-methylphenyl)sulfonyl]amino}carbonyl)benzyl]-1H-indol-5-yl}carbamate The title compound is prepared as illustrated in Example 19 starting with the product of Example 8, step 4, and the appropriate sulfonamide. MS: m/z (M−1) 628

EXAMPLE 26

Cyclopentyl N-{1-benzhydryl-3-[2-methoxy-4-({[(trifluoromethyl)sulfonyl]amino}carbonyl)benzyl]-1H-indol-5-yl}carbamate The title compound is prepared as illustrated in Example 19 starting with the product of Example 3, step 4, and the appropriate sulfonamide. MS: m/z (M−1) 704

EXAMPLE 27 cyclopentyl N-[1-benzhydryl-3-(2-methoxy-4-{[(methylsulfonyl)amino]carbonyl}benzyl)-1H-indol-5-yl]carbamate The title compound is prepared as illustrated in Example 19 starting with the product of Example 3, step 4, and the appropriate sulfonamide. MS: m/z (M−1) 650

EXAMPLE 28 cyclopentyl N-{1-benzhydryl-3-[4-({[(2-chlorophenyl)sulfonyl]amino}carbonyl)-2-methoxybenzyl]-1H-indol-5-yl}carbamate The title compound is prepared as illustrated in Example 19 starting with the product of Example 3, step 4, and the appropriate sulfonamide.

EXAMPLE 29 cyclopentyl N-(3-{4-[({[5-(acetylimino)-4-methyl-4,
5-dihydro1,3,4-thiadiazol-2-yl]sulfonyl}amino)
carbonyl]-2-methoxybenzyl}-1-benzhydryl-1H-
indol-5-yl)carbamate The title compound is prepared as illustrated in Example 19 starting with the product of Example 3, step 4, and the appropriate sulfonamide.

EXAMPLE 30 cyclopentyl N-(1-benzhydryl-3-{4-[({[5-
(dimethylamino)-1-naphthyl]sulfonyl}amino)
carbonyl]-2-methoxybenzyl-1H-indol-5-yl)
carbamate The title compound is prepared as illustrated in Example 19 starting with the product of Example 3, step 4, and the appropriate sulfonamide.

EXAMPLE 31 cyclopentyl N-[1-benzhydryl-3-(4-{
[(benzylsulfonyl)amino]carbonyl}-2-
methoxybenzyl)-1H-indol-5-yl]carbamate The title compound is prepared as illustrated in Example 19 starting with the product of Example 3, step 4, and the appropriate sulfonamide. MS: m/z (M−1) 726

EXAMPLE 32 cyclopentyl N-{1-benzhydryl-3-[4-({[(2,4-dimethyl-
1,3-thiazol-5-yl)sulfonyl]amino}carbonyl)-2-
methoxybenzyl]-1H-indol-5-yl}carbamate The title compound is prepared as illustrated in Example 19 starting with the product of Example 3, step 4, and the appropriate sulfonamide. MS: m/z (M−1) 747

EXAMPLE 33 cyclopentyl N-{1-benzhydryl-3-[4-({[(3,5-dimethyl-
4-isoxazolyl)sulfonyl]amino}carbonyl)-2-
methoxybenzyl]-1H-indol-5-yl}carbamate The title compound is prepared as illustrated in Example 19 starting with the product of Example 3, step 4, and the appropriate sulfonamide. MS: m/z (M−1) 731

EXAMPLE 34 cyclopentyl N-(3-{4-[({[5-(acetylamino)-1,3,4-
thiadiazol-2-yl]sulfonyl}amino)carbonyl]-2-
methoxybenzyl}-1-benzhydryl-1H-indol-5-yl)
carbamate The title compound is prepared as illustrated in Example 19 starting with the product of Example 3, step 4, and the appropriate sulfonamide.

EXAMPLE 35 cyclopentyl N-(1-benzhydryl-3-{2-methoxy-4[({[4-
(3-methyl-5-oxo-4,5-dihydro-1H-pyrazol-1-yl)
phenyl]sulfonyl}amino)carbonyl]benzyl}-1H-indol-
5-yl)carbamate The title compound is prepared as illustrated in Example 19 starting with the product of Example 3, step 4, and the appropriate sulfonamide.

EXAMPLE 36

N-{4-[(1-benzhydryl-5-nitro-1H-indol-3-yl)methyl]-
3-methoxybenzoyl}-2-methylbenzenesulfonamide The title compound is prepared as illustrated in Example 19 starting with the product of Example 12, step 2, and the appropriate sulfonamide. MS: m/z (M−1) 644

EXAMPLE 37

N-{4-[(1-benzhydryl-5-nitro-1H-indol-3-yl)methyl]-
3-methoxybenzoyl}(trifluoro)methanesulfonamide The title compound is prepared as illustrated in Example 19 starting with the product of Example 12, step 2, and the appropriate sulfonamide. MS: m/z (M−1) 622

EXAMPLE 38

N-{4-[(1-benzhydryl-5-bromo-1H-indol-3-yl)
methyl]-3-methoxybenzoyl}-2-
methylbenzenesulfonamide The title compound is prepared as illustrated in Example 19 starting with the product of Example 13, step 2, and the appropriate sulfonamide. MS: m/z (M−1) 679

EXAMPLE 39

N-{4-[(1-benzhydryl-5-bromo-1H-indol-3-yl)
methyl]-3-methoxybenzoyl}(trifluoro)
methanesulfonamide The title compound is prepared as illustrated in Example 19 starting with the product of Example 13, step 2, and the appropriate sulfonamide. MS: m/z (M−1) 657

EXAMPLE 40

N-{1-benzhydryl-3-[2-methoxy-
4-({[(trifluoromethyl)sulfonyl]amino}carbonyl)
benzyl]-1H-indol-5-yl}cyclopentanecarboxamide The title compound is prepared as illustrated in Example 19 starting with the product of Example 11, step 4, and the appropriate sulfonamide. MS: m/z (M−1) 688

EXAMPLE 41

N-[4-({1-benzhydryl-5-[(methylsulfonyl)amino]-1H-
indol-3-yl}methyl)-3-methoxybenzoyl](trifluoro)
methanesulfonamide The title compound is prepared as illustrated in Example 19 starting with the product of Example 10, step 4, and the appropriate sulfonamide. MS: m/z (M−1) 670

EXAMPLE 42

N-{4-[(1-benzhydryl-5-{[(butylamino)carbonyl]
amino}-1H-indol-3-yl)methyl]-3-methoxybenzoyl}
(trifluoro)methanesulfonamide The title compound is prepared as illustrated in Example 19 starting with the product of Example 9, step 4, and the appropriate sulfonamide. MS: m/z (M−1) 691

EXAMPLE 43

N-{1-benzhydryl-3-[2-methoxy-4-({[(2-
methylphenyl)sulfonyl]amino}carbonyl)benzyl]-1H-
indol-5-yl}cyclopentanecarboxamide The title compound is prepared as illustrated in Example 19 starting with the product of Example 11, step 4, and the appropriate sulfonamide. MS: m/z (M−1) 710

EXAMPLE 44

4-({5-[(cyclopentylcarbonyl)amino]-1-[phenyl(2-pyridinyl)methyl]-1H-indol-3-yl}methyl)-3-methoxybenzoic acid Step 1 The intermediate 5-amino indole is prepared as in Example 1, step 3.

Step 2 The intermediate sulfonamide is prepared as in Example 1, step 4, using the appropriate acylating agent.

Step 3 The intermediate acid is prepared as in Example 1, step 5, using the above intermediate.

Step 4 The title compound is prepared as illustrated in Example 19 starting with the intermediate above and the appropriate sulfonamide. MS: m/z (M−1) 738

EXAMPLE 45

N-[4-({1-benzhydryl-5-[(benzylsulfonyl)amino]-1H-indol-3-yl}methyl)-3-methoxybenzoyl](trifluoro)methanesulfonamide Step 1 The intermediate 5-amino indole is prepared as in Example 1, step 3.

Step 2 The intermediate sulfonamide is prepared as in Example 1, step 4, using the appropriate acylating agent.

Step 3 The intermediate acid is prepared as in Example 1, step 5, using the above intermediate.

Step 4 The title compound is prepared as illustrated in Example 19 starting with the intermediate above and the appropriate sulfonamide. MS: m/z (M−1) 746

EXAMPLE 46

N-{1-benzhydryl-3-[2-methoxy-4-({[(trifluoromethyl)sulfonyl]amino}carbonyl)benzyl]-1H-indol-5-yl}-3-thiophenecarboxamide Step 1 The intermediate 5-amino indole is prepared as in Example 1, step 3.

Step 2 The intermediate amide is prepared as in Example 1, step 4, using the appropriate acylating agent.

Step 3 The intermediate acid is prepared as in Example 1, step 5, using the above intermediate.

Step 4 The title compound is prepared as illustrated in Example 19 starting with the intermediate above and the appropriate sulfonamide. MS: m/z (M−1) 702

EXAMPLE 49 benzyl N-{1-benzhydryl-3-[2-methoxy-4-({[(trifluoromethyl)sulfonyl]amino}carbonyl)benzyl]-1H-indol-5-yl}carbamate Step 1 The intermediate 5-amino indole is prepared as in Example 1, step 3.

Step 2 The intermediate carbamate is prepared as in Example 1, step 4, using the appropriate acylating agent.

Step 3 The intermediate acid is prepared as in Example 1, step 5, using the above intermediate.

Step 4 The title compound is prepared as illustrated in Example 19 starting with the intermediate above and the appropriate sulfonamide. MS: m/z (M−1) 726

EXAMPLE 50

4-[(-benzhydryl-5-nitro-1H-indol-3-yl)methyl]benzoic acid

Step 1 The intermediate 3-alkylated 5-nitroindole is prepared as illustrated in Example 1, step 1, using the appropriate alkylating agent.

Step 2 The intermediate 3-alkylated 5-nitroindole is N-alkylated as illustrated in Example 3, step 1.

Step 3 The title compound is prepared as illustrated in Example 1, step 5. MS: m/z (M−1) 461

EXAMPLE 51

4-[(1-benzhydryl-5-bromo-1H-indol-3-yl)methyl]benzoic acid

Step 1 The intermediate 3-alkylated 5-bromoindole is prepared as illustrated in Example 13, step 1, using the appropriate alkylating agent.

Step 2 The intermediate 3-alkylated 5-nitroindole is N-alkylated as illustrated in Example 13, step 2.

Step 3 The title compound is prepared as illustrated in Example 13, step 3. MS: m/z (M−1) 494

EXAMPLE 52

4-[(1-benzhydryl-5-{[(cyclopentyloxy)carbonyl]amino}-1H-indol-3-yl)methyl]benzoic acid Step 1 Starting with the material prepared in Example 50, step 2, the desired intermediate is prepared as illustrated in Example 3, step 2.

Step 2 The intermediate carbamate is prepared from the above intermediate as illustrated in Example 3, step 3.

Step 3 The title compound is prepared from the above intermediate as illustrated in Example 3, step 4. MS: m/z (M−1) 543

EXAMPLE 53 cyclopentyl N-{1-benzhydryl-3-[4-({[[(2-methylphenyl)sulfonyl]1amino}carbonyl)benzyl]-1H-indol-5-yl}carbamate The title compound is prepared from the product of Example 52, step 3, as illustrated in Example 19. MS: m/z (M−1) 697

EXAMPLE 54 cyclopentyl N-{1-benzhydryl-3-[4-({[(trifluoromethyl)sulfonyl]amino}carbonyl)benzyl]-1H-indol-5-yl}carbamate The title compound is prepared from the product of Example 52, step 3, as illustrated in Example 26. MS: m/z (M−1) 674

EXAMPLE 55

N-{4-[(1-benzhydryl-5-nitro-1H-indol-3-yl)methyl]benzoyl}(trifluoro)methanesulfonamide The title compound is prepared from the product of Example 55, step 3, as illustrated in Example 26. MS: m/z (M−1) 592

EXAMPLE 56

N-{4-[(1-benzhydryl-5-nitro-1H-indol-3-yl)methyl]benzoyl}-2-methylbenzenesulfonamide The title compound is prepared from the product of Example 55, step 3, as illustrated in Example 19. MS: m/z (M−1) 614

EXAMPLE 57

N-{4-[(1-benzhydryl-5-bromo-1H-indol-3-yl)methyl]benzoyl}-2-methylbenzenesulfonamide The title compound is prepared from the product of Example 51, step 3, as illustrated in Example 38. MS: m/z (M−1) 649

EXAMPLE 58

N-{4-[(1-benzhydryl-5-bromo-1H-indol-3-yl) methyl]benzoyl}(trifluoro)methanesulfonamide The title compound is prepared from the product of Example 51 step 3 as illustrated in Example 39. MS: m/z (M−1) 627

EXAMPLE 59

3-({2-[1-(4-benzylbenzyl)-1H-indol-3-yl]-2-oxoacetyl}amino)benzoic acid

Step 1—To a solution of methyl 3-aminobenzoate (2.4 g, 16.0 mmol) in $CH_2Cl_2$ (50 mL) and saturated sodium bicarbonate (50 mL) at 5° C. is added 3-indolylglyoxalyl chloride (3.0 g, 14.4 mmol). The reaction is stirred to room temperature over 2 h, taken up in ethyl acetate (200 mL), washed with brine (3×50 mL), dried ($MgSO_4$), filtered and concentrated. Crystallization of the crude material afforded the desired intermediate (2.7 g, 58%) as a colorless solid.

Step 2—To a solution of the above intermediate (0.3 g, 0.93 mmol) in DMF (1.5 mL) at 0° C. is added potassium bis(trimethylsilyl)amide (0.41 g, 2.06 mmol). After the reaction is stirred at room temperature 30 min 4-benzylbenzyl bromide (0.27 g, 1.03 mmol) is added. The reaction is stirred 3 h, taken up in ethyl acetate (10 mL), washed with brine (3×2 mL), dried ($MgSO_4$), filtered and concentrated. Radial silica chromatography (2 mm, 10%–35% ethyl acetate/hexanes) afforded the desired intermediate (0.19 g, 41 %) as a colorless oil.

Step 3—The ester obtained in step 2 was treated with sodium hydroxide (2 mL, 5 M) in THF (5 mL) and MeOH (2 mL). The reaction was stirred overnight, taken up in ethyl acetate (50 mL), washed with sodium biphosphate (1×10 mL), brine (2×10 mL), dried ($MgSO_4$), filtered and concentrated. Trituration of the material in ethyl acetate with hexanes afforded the title compound (0.105 g, 60%) as a colorless solid. MS: m/z (M−1) 487

EXAMPLE 60

3-({2-[1-(4-{[3,5-bis(trifluoromethyl)phenoxy] methyl}benzyl)-1H-indol-3yl]-2oxoacetyl}amino) benzoic acid The intermediate prepared in Example 59, step 1, was N−1 alkylated with the appropriate reagent using the procedure described in Example 59, step 2.

Step 2 The product ester was hydrolyzed as described in Example 59, step 3. MS: m/z (M−1) 639

EXAMPLE 61

3-{[2-(1-benzhydryl-1H-indol-3-yl)-2-oxoacetyl] amino}benzoic acid

The intermediate prepared in Example 59, step 1, was N−1 alkylated with the appropriate reagent using the procedure described in Example 59, step 2.

Step 2 The product ester was hydrolyzed as described in Example 59, step 3. MS: m/z (M−1) 473

EXAMPLE 62

3-[(2-{1-[3-(4-benzylphenoxy)propyl]-1H-indol-3-yl}-2-oxoacetyl)amino]benzoic acid Step 1 The intermediate prepared in Example 59, step 1, was N−1 alkylated with the appropriate reagent using the procedure described in Example 59, step 2.

Step 2 The product ester was hydrolyzed as described in Example 59, step 3. MS: m/z (M−1) 531

EXAMPLE 63

3-[(2-{1-[3,4-bis(benzyloxy)benzyl]-1H-indol-3-yl}-2-oxoacetyl)amino]benzoic acid Step 1 The intermediate prepared in Example 59, step 1, was N−1 alkylated with the appropriate reagent using the procedure described in Example 59, step 2.

Step 2 The product ester was hydrolyzed as described in Example 59, step 3. MS: m/z (M−1) 609

EXAMPLE 64

3-[(2-{1-[2-(benzylsulfonyl)benzyl]-1H-indol-3-yl}-2-oxoacetyl)amino]benzoic acid Step 1 The intermediate prepared in Example 59, step 1, was N−1 alkylated with the appropriate reagent using the procedure described in Example 59, step 2.

Step 2 The product ester was hydrolyzed as described in Example 59, step 3. MS: m/z (M−1) 551

EXAMPLE 65

3-[({1-benzhydryl-5-[(cyclopentylcarbonyl)amino]-1H-indol-3-yl}methyl)amino]benzoic acid Step 1 To a solution of the aldehyde prepared in Example 114, step 3 (0.3 g, 0.7 mmol) in dichloroethane (2 mL) and DMF (1 mL) is added methyl 3-amino benzoate (0.113 g, 0.735 mmol, 1.05 eq) and acetic acid (0.13 mL, 2.1 mmol, 3 eq). After stirring 30 min sodium triacetoxyborohydride (0.18 g, 0.84 mmol, 1.2 eq) is added and the reaction is allowed to stir an additional 4 h after which it is taken up in ethyl acetate (20 mL), washed with saturated sodium bicarbonate (1×10 mL), brine (2×5 mL), dried ($MgSO_4$), filtered and concentrated. Silica chromatography (30% ethyl acetate/hexanes) afforded the desired intermediate (0.24 g, 60%) as a colorless oil.

Step 2 The product ester was hydrolyzed as described in Example 59 step 3 to give the title compound (0.11 g, 55%). MS: m/z (M−1) 542

EXAMPLE 66

2-[4-({1-benzhydryl-5-[(cyclopentylcarbonyl) amino]-1H-indol-3-yl}methyl)piperazino]acetic acid The title compound was prepared as described in Example 65 using the appropriate amine. MS: m/z (M−1) 549

EXAMPLE 67

2-[1-({1-benzhydryl-5-[(cyclopentylcarbonyl) amino]-1H-indol-3-yl}methyl)-3-oxo-2-piperazinyl] acetic acid The title compound was prepared as described in Example 65 using the appropriate amine. MS: m/z (M−1) 563

EXAMPLE 68

2-[({1-benzhydryl-5-[(cyclopentylcarbonyl)amino]-1H-indol-3-yl}methyl)amino]-3-hydroxypropanoic acid The title compound was prepared as described in Example 65 using the appropriate amine. MS: m/z (M−1) 510

EXAMPLE 69

2-[1-(4-benzylbenzyl)-5-(benzyloxy)-1H-indol-3-yl]-2-oxoacetic acid

Step 1—Ethylmagnesium bromide (3M in ether, 57 mL) was diluted in ether (50 mL). 5-Benzyloxyindole (12.7 g) dissolved in ether (150 mL) was added to the Grignard solution at −78° C. After 1.25 h, ethyloxalyl chloride (17.12 g) was added. The reaction was stirred 15 min, quenched with saturated sodium bicarbonate, taken up in ethyl acetate and washed with water, dried ($MgSO_4$), filtered and concentrated. The resulting solid was triturated with ethanol and stirred for 1 h. The desired product (5.75 g, 31%) was isolated as a yellow solid and used without further purification.

Step 2—To the above indole in DMF at 0° C. was added sodium hydride (0.4 g, 60% dispersion in oil). After warming to room temperature, 4-benzylbenzylbromide (2.2 g) was added and the mixture was stirred overnight. As the reaction was not yet done (TLC) additional 4-benzylbenzylbromide (1.0 g) was added and the reaction stirred for 2.5 h. The reaction was taken up in ethyl acetate and washed with water, dried ($MgSO_4$), filtered and concentrated. Chromatography (20% ethyl acetate/hexanes) afforded the desired compound (3.1 g 90%).

Step 3—The above ester was placed in a solution of NaOH (2N):THF:MeOH (1:2:1) and stirred overnight at room temperature. The reaction was acidified with 6 N HCl and the product extracted with ethyl acetate. The organic layers were dried ($MgSO_4$), filtered and concentrated. The solid was triturated with ethanol and stirred for 1 h. The solid was filtered and dried affording the title compound (1.85 g) as a yellow solid. MS: m/z (M−1) 474

EXAMPLE 70

2-{5-(benzyloxy)-1-[2,4-bis(trifluoromethyl)benzyl]-1H-indol3-yl}-2-oxoacetic acid

The indole prepared in Example 69, step 1, was alkylated with the appropriate alkyl bromide and hydrolyzed as described in Example 69, steps 2 and 3. MS: m/z (M−1) 520

EXAMPLE 71

3-({2-[1-(4-benzylbenzyl)-5-(benzyloxy)-1H-indol-3-yl]-2-oxoacetyl}amino)benzoic acid

Step 1—To a solution of the acid from Example 69, step 3, (0.810 g) in THF (28 mL) was added CDI. The reaction was stirred 30 min and then ethyl 3-aminobenzoate (0.330 g) was added and the reaction was stirred overnight. The reaction mixture was taken up in ethyl acetate and washed with water, dried ($MgSO_4$), filtered and concentrated. The crude material was triturated with ethanol and stirred for 1 h, filtered and dried. The desired product (0.76 g, 75%) was isolated as a yellow solid.

Step 2—The above ester was dissolved in NaOH (2N):THF:MeOH (1:2:1) and stirred 4h. The mixture was acidified with 6 N HCl and extracted with ethyl acetate. The combined organic layers were dried ($MgSO_4$), filtered and concentrated. The crude solid was triturated with ethanol/hexane to afford the title compound (0.48 g, 69%) as a yellow solid.

EXAMPLE 72

5-[(2-{5-(benzyloxy)-1-[2,4-bis(trifluoromethyl)benzyl]-1H-indol-3-yl}-2-oxoacetyl)amino]isophthalic acid

The alkylated indole from Example 70 was coupled to the appropriate amino acid and hydrolyzed as illustrated in Example 71, steps 1 and 2. MS: m/z (M−1) 683

EXAMPLE 73

3-[(2-{5-(benzyloxy)-1-[2,4-bis(trifluoromethyl)benzyl]-1H-indol-3-yl}-2-oxoacetyl)amino]benzoic acid

The alkylated indole from Example 70 was coupled to the appropriate amino acid and hydrolyzed as illustrated in Example 71, steps 1 and 2. MS: m/z (M−1) 639

EXAMPLE 74

5-({2-[1(4-benzylbenzyl)-5-(benzyloxy)-1H-indol-3-yl]-2-oxoacetyl}amino)-2-[(5-chloro-3-pyridinyl)oxy]benzoic acid

The alkylated indole from Example 69 was coupled to the appropriate amino acid and hydrolyzed as illustrated in Example 71, steps 1 and 2.

EXAMPLE 75

5-[(2-{5-(benzyloxy)-1-[2,4-bis(trifluoromethyl)benzyl]-1H-indol-3-yl}-2-oxoacetyl)amino]-2-[(5-chloro-3-pyridinyl)oxy]benzoic acid

The alkylated indole from Example 70 was coupled to the appropriate amino acid and hydrolyzed as illustrated in Example 71, steps 1 and 2.

EXAMPLE 76

2-[1-(4-benzylbenzyl)-5-(benzyloxy)-1H-indol-3-yl]-N-[3-({[(4-methylphenyl)sulfonyl]amino}carbonyl)phenyl]-2-oxoacetamide

To the acid obtained in Example 71 (0.1 g) in $CH_2C_2$ (10 mL) is added THF (5 mL) to help dissolve the compound. EDCI (0.045 g) and DMAP (0.02 g) was added and the mixture was stirred a room temperature of 1 h. p-Toluenesulfonamide (0.04 g) was added and the reaction was stirred overnight. The reaction mixture was take up in ethyl acetate and washed with water, dried ($MgSO_4$), filtered and concentrated. Chromatography (7% $MeOH/CH_2Cl_2$) afforded the title compound (0.045 g, 40%) as a yellow solid. MS: m/z (M−1) 746

EXAMPLE 77

2-[5-bromo-1-(cyclopropylmethyl)-1H-indol-3-yl]acetic acid

To 5-bromoindole-3-acetic acid (890 mg, 3.5 mmol) in 1-methyl-2-pyrrolidinone (12 mL) at 0° C. were added $^{i}Pr_2NEt$ (21 mmol) and bromomethylcyclopropane (10.5 mmol). The reaction mixture was heated at 50° C. for 19 h before partitioning between diethyl ether and ice water. After adjusting the pH to 3, the aqueous layer was extracted with diethyl ether. The organic layers were combined, washed with $NaH_2PO_4$, dried over $MgSO_4$ and evaporated to dryness. Purification on silica gel column (30% EtOAc in hexane) yielded 927 mg (86% yield) of the product.

EXAMPLE 78

2-[1-(cyclopropylmethyl)-5-(2-thienyl)-1H-indol-3-yl]acetic acid

To a sealed tube containing 2-[5-bromo-1-(cyclopropylmethyl)-1H-indol-3-yl]acetic acid (100 mg, 0.32 mmol), 2-thiopheneboronic acid (124 mg, 0.97 mmol), ($C_6H_5$)$_4$Pd (37 mg, 0.032 mmol), Na$_2$CO$_3$ (2.6 mmol) in a mixture of benzene/EtOH/H$_2$O (5/1/3, 4.5 mL) was heated at 85° C. for 19 h. The mixture was poured onto diethyl ether and adjusted to pH 3 before extracting with diethyl ether. The mixture was washed with NaH$_2$PO$_4$, dried over MgSO$_4$ and evaporated to give the crude product which was purified on silica gel column (33% EtOAc in hexane with 1% HCOOH) to give 79 mg (78% yield) of the product.

EXAMPLE 79

2-{1-(cyclopropylmethyl)-5-[3-(trifluoromethyl) phenyl]-1H-indol-3-yl}acetic acid The title compound was prepared according to the procedure described in Example 78 except that 3-(trifluoromethyl)phenylboronic acid was used.

EXAMPLE 80

2-[5-(1-benzofuran-2-yl)-1-benzyl-1H-indol-3-yl] acetic acid

The title compound was prepared according to the procedure described in Example 78 except that 2-[5-bromo-1-benzyl-1H-indol-3-yl]acetic acid and benzo[b]furan-2-boronic acid were used.

EXAMPLE 81

2-(1-benzyl-5-phenyl-1H-indol-3-yl)acetic acid

The title compound was prepared according to the procedure described in Example 78 except that 2-[5-bromo-1-benzyl-1H-indol-3-yl]acetic acid and phenylboronic acid were used.

EXAMPLE 82A 5-((E)-{1-[3-(3-benzylphenoxy)propyl]-1H-indol-3-yl}methylidene)-1,3-thiazolane-2,4-dione Step 1 The procedure in Example 22 was followed using 3-formyl indole (0.4 g, 2.8 mmol), sodium hydride (0.102 g, 3.0 mmol) and the iodide (0.97 g, 2.8 mmol) in DMF (10 ml). Flash chromatography (Hex/EtOAc, 1/1) gave 0.86 g (84%) of the desired intermediate.

Step 2 The intermediate from step 1 (0.8 g, 2.2 mmol) and 2.4-thiazolidinedione (0.25, g, 2.2 mmol) was dissolved in toluene (5 mL). Piperidine (0.064 mL, 0.6 mmol) and acetic acid (0.012 mL) were added and the mixture was heated to reflux for 2 h. The reaction was allowed to cool to rt, water was added and the aqueous layer was extracted with ethyl acetate. The organic layer was washed with water, brine, dried (MgSO4), filtered and concentrated. Flash chromatography (hexane/ethyl acetate, 3/2) afforded the title compound (0.345 g (33%) as an orange solid.

EXAMPLE 82B

4-{[5-((E)-{1-[3-(3-benzylphenoxy)propyl]-1H-indol-3-yl}methylidene)-2,4-dioxo-1,3-thiazolan-3-yl]methyl}benzoic acid The procedure in Example 22 steps 1 and 2 were followed to give 0.14 g (47% for 2 steps) of the title compound as a yellow powder.

EXAMPLE 82C

2-[5-((E)-{1-[3-(3-benzylphenoxy)propyl]-1H-indol-3-yl}methylidene)-2,4-dioxo-1,3-thiazolan-3-yl] acetic acid The procedure in Example 22 steps 1 and 2 were followed to give 0.107 g (42% for 2 steps) of the title compound as a yellow powder.

EXAMPLE 83

3-{1-[3-(3-benzylphenoxy)propyl]-1H-indol-3-yl}propanoic acid

The procedure in Example 22 step 1 was followed except 2 eq. of sodium hydride was used and 0.142 g (65%) of the title compound was isolated as a white oily solid.

EXAMPLE 84

3-{1-benzhydryl-5-[(cyclopentylcarbonyl)amino]-1H-indol-3-yl}propanoic acid

Step 1 To a solution of the aldehyde from Example 114, step 1 (1.0 g, 2.8 mmol) in toluene (20 ml) was added carbomethoxyethylidene triphenylphosphorane (0.98 g, 2.9 mmol). The mixture was heated overnight at reflux and then concentrated. The residue was dissolved in CH$_2$Cl$_2$ and silica gel was added. The mixture was concentrated and the resulting solid was purified by flash chromatography (Hex/EtOAc, 3/1). Compound 30 1.01 g (88%) was isolated as a yellow solid.

Step 2 To a solution of the above intermediate (0.1 g, 0.24 mmol) in THF (10 ml), was added platinum on activated carbon (5% Pt, 0.05 g, 50 wt %). Hydrogen gas was bubbled into the suspension for 2 min, the vessel was sealed tightly and the reaction was stirred overnight at rt. Argon gas was then bubbled through the reaction for 15 min before the mixture was filtered through a pad of Celite. The pad was washed with EtOAc and the filtrate was concentrated. The residue was dissolved in CH$_2$Cl$_2$ (5 ml). Aqueous saturated NaHCO$_3$ (3 ml) was added, followed by cyclopentanecarbonyl chloride (0.036 ml). The biphasic mixture was stirred for 2 h at rt and diluted with CH$_2$Cl$_2$. The organic layer was washed with water and brine, dried and concentrated to a white solid. Recrystallization from EtOAc/Hex gave 0.11 g (95%) of the desired intermediate as a white solid.

Step 3 Hydrolysis of the above ester with NaOH (1N, 2 mL) in THF (2 mL) and MeoOH (2 mL) followed by recrystallization from hot EtOAc afforded 0.054 g (50%) of the title compound as a white solid.

EXAMPLE 85

N-(1-benzhydryl-3-{3-[(methylsulfonyl)amino]-3-oxopropyl}-1H-indol-5-yl)cyclopentanecarboxamide To a solution of the acid from Example 84 step 3 (0.1 g, 0.22 mmol) in THF (5 ml) was added methanesulfonamide (0.027 g, 0.28 mmol), EDCI (0.54 g, 0.28 mmol) and DMAP (0.012 g, 0.1 mmol). The mixture was heated at 50° C. overnight then diluted with EtOAc, washed with water and brine, dried and concentrated. Flash chromatography (Hex/EtOAc, 1/1) gave 0.1 g (87%) of the title compound as a white solid.

EXAMPLE 86A (E)-3-{1-benzhydryl-5-[(cyclopentylcarbonyl) amino]-1H-indol-3-yl}-2-propenoic acid Step 1 The same procedure as Example 84 step 2 was used to prepare the desired intermediate from the nitroindole (Example 114 step 1).

Step 2 The procedures in Example 84, step 1 and 3 were used to prepare the title compound from the above intermediate.

EXAMPLE 86B

N-(1-benzhydryl-3-{(E)-3-[(methylsulfonyl)amino]-3-oxo-1-propenyl}-1H-indol-5-yl) cyclopentanecarboxamide The acid from Example 86A was used to prepare the title compound according to the procedure in example 85.

EXAMPLE 87A (E)-3-{1-benzhydryl-5-nitro-1H-indol-3-yl}-2-propenoic acid

The ester from Example 84 step 1 was saponified according to the procedure in Example 84 step 3 and recrystallization from hot EtOAc afforded 0.155 g (90%) of the title compound as a white solid.

EXAMPLE 87B

N-((E)-3-{1-benzhydryl-5-nitro-1H-indol-3-yl}-2-propenoyl)methanesulfonamide

The procedure in Example 85 was used to prepare the title compound from the product of Example 87A.

EXAMPLE 88

4-[(1-benzhydryl-5-chloro-2-methyl-1H-indol-3-yl)methyl]benzoic acid

Step 1 To an ice-cold (0° C.) solution of trifluoroacetic acid (1.7 ml, 15 mmol) and triethylsilane (4.8 ml, 30 mmol) in $CH_2Cl_2$ (20 mL) was added a solution of 5-chloro-2-methylindole (1.66 g, 10 mmol) and methyl 4-formylbenzoate (1.8 g, 11 mmol) in $CH_2Cl_2$ (50 mL) over a period of 5 min. The resulting homogeneous solution was stirred at 0° C. for 1 h and rt for 2 h, at which time EtOAc (150 mL) and aqueous sodium bicarbonate (to pH=8) was added. The organic layer was washed with water and brine, dried over $MgSO_4$ and concentrated. Flash chromatography (Hex/EtOAc, 4/1) gave 1.98 g (63%) of desired intermediate as a light-tan solid.

Step 2 Sodium hydride (0.2 g, 5 mmol) was washed with dry hexanes (3×10 ml) and then suspended in DMF (6 mL) and cooled to 0° C. A solution of the above intermediate (1.57 g, 5 mmol) in DMF (4 mL) was dropwise at 0C and the resulting mixture was stirred for 30 min at which time the diphenylbromomethane (1.24 g, 5 mmol) was added. The mixture was allowed to reach rt and stirred for an additional 48 h. EtOAc (30 mL) was added followed by aqueous $NaH_2PO_4$ solution (10 ml). The organic layer was washed with water and brine, dried and concentrated. Flash chromatography (Hex/EtOAc, 7/1) provided 0.98 g (41%) of the desired intermediate as a ivory foam.

Step 3 The above intermediate was saponified according to the procedure in Example 84 step 3. Flash chromatography (EtOAc) provided 0.3 g (89%) of the title compound as a tan crystalline solid. MS: m/z (M−1) 464

EXAMPLE 89

4-{[1-benzhydryl-5-({[4-(trifluoromethyl)phenyl]sulfonyl}amino)-1H-indol-3-yl]methyl}-3-methoxybenzoic acid Step 1—The intermediate from Example 3 step 2 (1 eq) (see scheme #) was weighed in to a flask along with the 4-triflouromethylbenzene sulfonyl chloride (1.2 eq) and then they were flushed with nitrogen, taken up in dichloroethane (0.15M) and then pyridine was added (1.2 eq) at which time the reaction was left to stir overnight and then worked up by the addition of the polymer bound amine (Parlow, J. J, Mischke, D. A., Woodard, S. S. *J. Org. Chem.* 1997, 62, 55908–5919) (1.6 g/b 1 mmol) and the resulting slurry was stirred a minimum of 15 minutes and then it was filtered and washed with dichloroethane and the dichloroethane solution was dried and concentrated to yield 98% of the desired product with high purity.

Step 2—The crude material from step 1 was dissolved THF/MeOH (2.5/1) and then 4N NaOH was added (•3 eq) and the reaction was stirred until complete hydrolysis was observed by TLC. At this point the reaction quenched with enough amberlite ir 120 to make the solution acidic and then the resin was filtered off and rinsed and the desired product was obtained in 94% yield by drying and concentrating the solution. MS: m/z (M−1) 669

EXAMPLE 90

4-{[5-({[2-(acetylamino)-4-methyl-1,3-thiazol-5-yl]sulfonyl}amino)-1-benzhydryl-1H-indol-3-yl]methyl}-3-methoxybenzoic acid Step 1: Following step 1 for Example 89 using the appropriate sulfonyl chloride yielded 76% of the title compound after chromatographic purification.

Step 2: An analogous proceedure to step 2 for Example 89 above yielded 83% of the desired product. MS: m/z (M−1) 679

EXAMPLE 91

4-[(1-benzhydryl-5-{[(4-chloro-3-nitrophenyl)sulfonyl]amino}-1H-indol-3-yl)methyl]-3-methoxybenzoic acid Step 1: Following step 1 for Example 89 using the appropriate sulfonyl chloride yielded •100% of the title compound.

Step 2: An analogous proceedure to step 2 for Example 89 yielded 54% of the desired product after chromatographic purification. MS: m/z (M−1) 681

EXAMPLE 92

4-[(1-benzhydryl-5-{[(dimethylamino)sulfonyl]amino}-1H-indol-3-yl)methyl]-3-

Step 1: Following step 1 for Example 89 using the appropriate sulfonyl chloride yielded 49% of the title compound after chromatographic purification.

Step 2: An analogous proceedure to step 2 for Example 89 yielded •100% of the desired product. MS: m/z (M−1) 568

EXAMPLE 93

4-{[1-benzhydryl-5-({[4-(trifluoromethoxy)phenyl]sulfonyl}amino)-1H-indol-3-yl]methyl}-3-methoxybenzoic acid Step 1: Following step 1 for Example 89 using the appropriate sulfonyl chloride yielded •100% of the title compound.

Step 2: An analogous proceedure to step 2 for Example 89 yielded •100% of the desired product. MS: m/z (M−1) 685

EXAMPLE 94

4-[(1-benzhydryl-5-{[(2-methylphenyl)sulfonyl]amino}-1H-indol-3-yl)methyl]-3-methoxybenzoic acid Step 1: Following step 1 for Example 89 using the appropriate sulfonyl chloride yielded 56% of the title compound after chromatographic purification.

Step 2: An analogous proceedure to step 2 for Example 89 yielded •82% of the desired product. MS: m/z (M−1) 615

EXAMPLE 95

4-[(1-benzhydryl-5-{[(5-chloro-1,3-dimethyl-1H-pyrazol-4-yl)sulfonyl]amino}-1H-indol-3-yl) methyl]-3-methoxybenzoic acid Step 1: Following step 1 for Example 89 using the appropriate sulfonyl chloride yielded •100% of the title compound.

Step 2: An analogous proceedure to step 2 for Example 89 yielded 96% of the desired product. MS: m/z (M−1) 655

EXAMPLE 96

4-[(1-benzhydryl-5-{[(3,5-dimethyl-4-isoxazolyl) sulfonyl]amino}-1H-indol-3-yl)methyl]-3-methoxybenzoic acid Step 1: Following step 1 for Example 89 using the appropriate sulfonyl chloride yielded •100% of the title compound.

Step 2: An analogous proceedure to step 2 for Example 89 yielded 89% of the desired product. MS: m/z (M−1) 621

EXAMPLE 97

Cyclopentyl-N-{3-[4-(aminocarbonyl)-2-methoxybenzyl]-1-benzhydryl-1H-indol-5-yl}carbamate The compound of Example 3 (1.0 eq) was dissolved in THF (0.15M) and then carbonyl diinidizole (1.2 eq) was added and the reaction was stirred under N$_2$ for three hours at which time ammonium hydroxide was added (3 ml/g) and the reaction was stirred overnight when TIC analysis showed it was complete. To the reaction was added water and ethyl acetate, the layers were separated and the aqueous layer was extracted three times, the combined organic extracts were dried concentrated and chromatographed to yield 64% of the desired primary amide.

EXAMPLE 98 cyclopentyl N-{1-benzhydryl-3-[2-methoxy-4-(1H-1,2,3,4-tetraazol-5-yl)benzyl]-1H-indol-5-yl}carbamate Step 1—To the compound of Example 97 (1.0 eq) under N$_2$ was added CH$_2$Cl$_2$ (0.06M) and then (methoxycarbonylsulfamoyl)triethylammonium hydroxide inner salt (5.0 eq) portion wise over 5 hours and then the slurry was stirred overnight at which time TLC analysis indicated the reaction was complete so it was concentrated and chromatographed to yield 78% of the desired product.

Step 2—To the nitrile (1.0 eq) isolated in step 1 was add sodium azide (3 eq) and triethyl amine hydrochloride (1.5 eq) and n-methyl-2-pryrrolidinone (0.05 m) and then the reaction was heated to reflux under an inert atmosphere for 2.5 hours when it was poured into ice and water that was then acidified to pH 2 and the product was filtered off and then further purified by preparative chromatography to yield the desired compound in 22% yield. MS: m/z (M−1) 597

EXAMPLE 99

4-[({1-benzhydryl-5-[(cyclopentylcarbonyl)amino]-1H-indol-3-yl}carbonyl)amino]-3-thiophenecarboxylic acid Step 1 To the indole acid (1.0 eq) was added the amine (1.2 eq) the dimethylaminopyridine (10 mol %), 1-(3dimethylaminopropyl)-3-ethylcarbodiimide hydrochloride (1.5 eq) and then DMF(0.3M) and the reaction was stirred under nitrogen for 24 hours at 40° C. for 24 hours at which time it was poured into 1/2 saturated ammonium chloride solution and ethyl acetate and then the layers were separated and the aqueous layer was extracted 3 times, the combined organic layers were washed with water 2×, dried, concentrated and chromatographed to yield 38% of the amide.

Step 2 The ester from the previous step was dissolved in THF/MeOH (3:1) and then 1N NaOH (3.0 eq) was added and the reaction was stirred for until TLC analysis showed that the reaction was complete. The reaction was then concentrated, diluted with water, acidified to pH 2 with conc HCL, extracted with ethyl acetate 3×, the combined organics were dried over magnesium sulfate concentrated and purified via chromatography to yield the desired acid in 64% yield.

EXAMPLE 100

3-[({1-benzhydryl-5-[(cyclopentylcarbonyl)amino]-1H-indol-3-yl}carbonyl)amino]benzoic acid Step 1: The acid (see scheme #) was coupled with the appropriate amino ester following the procedure in Example 99, step one, except the reaction was run at room temperature and that the procedure yielded 80% of the desired product isolated by recrystalization.

Step 2: The nitro ester from step one (1.0 eq) was weighed into a flask along with 5% Platinum on Carbon (40 wt %) and the vessel was sealed with a septum and evacuated and flushed with argon 3×, then freshly distilled THF is added and the reaction is evacuated 2× and after the second evacuation a balloon of hydrogen inserted into the septum. The reaction is left under atmospheric hydrogen for 16 hours at which time tlc analysis indicates complete reduction and the reaction is flushed with argon and then filtered through a bed of celite and the catalyst is washed exhaustively with ethyl acetate, the filtrate was dried and concentrated and purified via chromatography to deliver 71% of the desired amine.

Step 3: The amine (1.0 eq) was dissolved in dichloromethane (0.3M) and then an equivalent amount of saturated sodium bicarbonate was added and finally the acid chloride introduced. The biphasic reaction mixture was vigorously stirred until TLC analysis indicated that the reaction was complete (generally a few hours) and then the reaction was diluted with dichloromethane and water, the layers were separated, the aqueous layer was extracted three times with dichloromethane, the combined organic layers were dried, concentrated and chromatographed to yield the desired amide in 41% yield.

Step 4: According to step 2, Example 99, the ester was hydrolyzed to the acid and yielded 71% of the final product. MS: m/z (M−1) 556

EXAMPLE 101

3-[({1-benzhydryl-5-[(cyclopentylcarbonyl)amino]-1H-indol-3-yl}carbonyl)amino]propanoic acid Step 1 To the final product in Example 114 (1.0 eq) in dichloromethane (0.1M) at 0° C. was added oxallyl chloride (2.0 eq) and then a few drops of DMF. The reaction was stirred a few hours at room temperature and concentrated and azeotroped 2× with toluene and placed on the high vacuum for 2 hours before being used crude for the next step.

Step 2: To the acid chloride generated in step 1 was added dichloromethane (0.1M) and then a solution of alanine methyl ester (1.05 eq, free base) in dichloromethane (1.0M) and then triethylamine (1.5 eq) was added and the resulting mixture was stirred overnight and worked up by the addition of 1/2 saturated ammonium chloride, the layers were separated, the aqueous layer was extracted three times with dichloromethane, the combined organic layers were dried and concentrated and purified via chromatography to yield the desired amide.

Step 3: The ester from step 2 was hydrolyzed under the conditions outlined for step 2, Example 99, to yield the desired acid.

EXAMPLE 102

N-[1-benzhydryl-3-({[(2-methylphenyl)sulfonyl] amino}carbonyl)-1H-indol-5-yl] cyclopentanecarboxamide Step 1: The acid chloride (1.0 eq) synthesized in step 1, Example 101, was weighed into a flask along with o-tolylsulfonamide (1.5 eq), DMAP (0.1 eq) and taken up in dichloromethane (0.1M) under nitrogen and then triethylamine (1.5 eq) was added and the resulting mixture was stirred for 12 hours and then worked up by the addition of 1/2 saturated ammonium chloride, the layers were separated, the aqueous layer was extracted three times with dichloromethane, the combined organic layers were dried and concentrated and purified via chromatography to yield the desired acylsulfonamide in 52% yield.

EXAMPLE 103

3-[(2-{1-benzhydryl-5-[(cyclopentylcarbonyl) amino]-1H-indol-3-yl}-2-oxoacetyl)amino] propanoic acid Step 1: According to the general procedure in step 1, Example 101, using the product from Example 115 and the appropriate amino ester yielded the desired product in •100% yield.

Step 2: The ester from step 1 was hydrolyzed under the conditions outlined for step 2, Example 99, to yield the desired acid. MS: m/z (M−1) 536

EXAMPLE 104

3-[(2-{1-benzhydryl-5-[(cyclopentylcarbonyl) amino]-1H-indol-3-yl}-2-oxoacetyl)amino]benzoic acid Step 1: According to the general procedure in step 1, Example 99, using the product from Example 115 and the appropriate amino ester yielded the desired product in •100% yield.

Step 2: The ester from step 1 was hydrolyzed under the conditions outlined for step 2, Example 99, to yield the desired acid. MS: m/z (M−1) 584

EXAMPLE 105

3-({2-[1-(4-benzylbenzyl)-5-(benzyloxy)-1H-indol-3-yl]acetyl}amino)benzoic acid

Step 1 An oven dried flask was charged with 5-benzyloxy indole-3-acetic acid (1 eq) (see scheme-1) and anhydrous DMF (0.18M) under nitrogen. Reaction mixture was then cooled to 0° C. and to this was added NaH (2.2 eq, 60% dispersion in mineral oil), stirred at 25° C. for 1 h followed by addition of a solution of the appropriate benzyl bromide (2.2 eq, 40% purity) (see scheme-1, steps 5,6) in anhydrous DMF, stirred overnight. Workup with ethyl acetate/water followed by chromatographic purification afforded the desired product in 66% yield.

Step 2 Dissolved the indole derivative from step 1 (1 eq) (see scheme-1) in THF/MeOH/H$_2$O (3:1:1 0.094M) and to this was added LiOHH$_2$O (1.2 eq), stirred at 25° C., overnight. Workup with ethyl acetate/water followed by chromatographic purification afforded the desired product in 74% yield.

Step 3 To the acid from step 2 (1 eq) (see scheme-1) was added methyl 3-aminobenzoate (1.05 eq), EDCI (1.37 eq) and DMAP (0.2 eq) followed by anhydrous DMF (0.086M), stirred at 25° C., overnight. Workup with ethyl acetate/1N HCl followed by chromatographic purification afforded the desired product in 80% yield.

Step 4 Dissolved the ester (1 eq) from step 3 (see scheme-1) in THF/MeOH/H$_2$O (3:1:1 0.04 M) and to this was added LiOHH$_2$O (1.2 eq), stirred at 25• C., overnight. Workup with ethyl acetate/1N HCl followed by trituration with CH$_2$Cl$_2$/hexane (1:1) for 0.5 h and then recrystallization from CH$_2$Cl$_2$ afforded the titled product in 97% yield. MS: m/z (M−1) 579

EXAMPLE 106

3-[(2-{5-(benzyloxy)-1-[2,4-bis(trifluoromethyl) benzyl]-1H-indol-3-yl}acetyl)amino]benzoic acid Step 1 Following procedure in step 1 of example 105, scheme-1 and using the appropriate benzyl bromide afforded the desired product in 50% yield after chromatographic purification.

Step 2 Following procedure in step 2 example 105, scheme-1 and using the appropriate indole derivative afforded the desired product in 67% yield after chromatographic purification.

Step 3 Following procedure in step 3 example 105, scheme-1 and using the appropriate indole derivative afforded the desired product in 75% yield after chromatographic purification.

Step 4 Following procedure in step 4 example 105, scheme-1 and using the appropriate indole afforded the desired product in 63% yield after chromatographic purification. MS: m/z (M−1) 625

EXAMPLE 107

5-(benzyloxy)-1-[2,4-bis(trifluoromethyl)benzyl]-2-methyl-1H-indole-3-carboxylic acid Step 1: The 5-Hydroxy-2-Methylindole-3-Carboxylate (1 eq) was combined with benzyl bromide (1.3 eq) and K$_2$CO$_3$ (325 mesh, 1.3 eq) in CH$_3$CN (0.1M). The resulting mixture was heated to reflux for 2 h. An additional amount of benzyl bromide (0.2 eq) and the heating was continued for 2 h. The reaction was worked up by addition of water and extraction with CH$_2$Cl$_2$. The organic extracts were washed with water, dried and concentrated. Flash chromatography provided the desired benzyl ether (63% yield), as well as the corresponding N,O-bisbenzyl derivative (22% yield).

Step 2: An ice cooled solution of the benzyl ether from step 1 (1 eq) in dry DMF (0.25M) was treated with NaH (60% in mineral oil, 1.1 eq). 2,4-Bis trifluoromethyl benzyl bromide (1.1 eq) was added after 1 h and the resulting mixture was stirred at 25° C. for 2 h. Solvent was evaporated under vacuo, the residue was dissolved in EtOAc, washed with water, dried and concentrated. The desired product was obtained in 77% yield after recrystallization from hexane/ $CHCl_3$.

Step 3: The product from step 2 (1 eq) in THF/MeOH (3/1) was heated to reflux with 1N NaOH (12 eq). After 48 h the reaction was quenched with AcOH and solvent was evaporated. The resulting product was recrystallized to afford crude material in 72% yield. Further purification by flash chromatography followed by recrystallization provided pure title compound. MS: m/z (M−1) 506

EXAMPLE 108

5-[({5-(benzyloxy)-1-[2,4-bis(trifluoromethyl) benzyl]-2-methyl-1H-indol-3-yl}carbonyl)amino] isophthalic acid Step 1: The acid prepared in step 3 (1 eq) of example 108 was reacted with EDCI (2 eq) and dimethyl 5-aminophthalate (5 eq) in THF (0.02M) in the presence of DMAP (2 eq). The reaction was heated to reflux for 48 h. EtOAc/water work up, followed by flash chromatography produced the desired amide in 32% yield.

Step 2: The material from step 1 (1 eq) was hydrolyzed by the action of $LiOHH_2O$ (2.2 eq) in THF/MeOH/water (3/1/1, 0.07M). After stirring at 25• C. overnight, the reaction mixture was quenched with AcOH and solvent was evaporated. EtOAc/water work up and trituration in hexane/ $CH_2Cl_2$ afforded the title compound in 82% yield. MS: m/z (M−1) 669

EXAMPLE 109

5-(benzyloxy)-2-methyl-1-(2-naphthylmethyl)-1H-indole-3-carboxylic acid

Step 1: An analogous procedure to step 2 example 108 using the main product of step 1 above and the appropriate bromide yielded the desired N-substituted indole in 71% yield after recrystallization.

Step 2: The ester from step 2 above (1 eq) in THF/MeOH (3/1) was heated to reflux with 4N KOH (2 eq). After 5 days solvent was evaporated and the residue partitioned between 1N HCl and $CHCl_3$. The organic extract was washed, dried and concentrated. The title compound was obtained in 92% yield after chromatographic purification and crystallization. MS: m/z (M−1) 420

EXAMPLE 110

5-({[5-(benzyloxy)-2-methyl-1-(2-naphthylmethyl)-1H-indol-3-yl]carbonyl}amino)isophthalic acid Step 1: The acid in Example 109 was converted in the corresponding amide following an analogous procedure to step 1 of Example 108. The product was contaminated with the aniline starting material which could only be partially removed by chromatography.

Step 2: Hydrolysis of the crude material following step 2 Example 108 provided the title compound after chromatographic purification (4% yield in Example 109).

EXAMPLE 111

1-benzyl-5-(benzyloxy)-2-methyl-1H-indole-3-carboxylic acid

Step 1: The minor product of step 1 (1 eq) Example 107 was dissolved in THF (0.1 M). KOH (2 eq) and 18-crown-6 (2 eq) were added and the resulting mixture was heated to reflux for 1.5 days. Work up as on step 2 Example 108 above provided the title compound in 32% yield. MS: m/z (M−1) 370

EXAMPLE 112

3-[(2-{5-(benzyloxy)-1-(4-chlorobenzyl)-2-[(2-naphthylsulfanyl)methyl]-1H-indol-3-yl}-2-oxoacetyl)amino]benzoic acid Step 1 The starting ethyl 5-benzyloxyindole-2-carboxylate (Scheme 21, step 1) was treated with LAH (1.3 eq) in THF (0.27M) at 0° C. under nitrogen for 1 h. Workup with NaOH and water followed by concentration afforded crude product (100%).

Step 2 The crude alcohol from step 1 was dissolved in DMF (0.38M), and treated with t-butyldimethylsilyl chloride (1.16 eq) and imidazole (1.26 eq) at 25° C. for 1 d. Workup and chromatographic purification afforded the pure product (93%).

Step 3 The silyl ether from step 2 was dissolved in methylene chloride (0.26M), and treated with BOC anhydride (1.24 eq), triethylamine (1.53 eq) and DMAP (0.21 eq) at 25° C. for 3 d. Workup and chromatographic purification afforded the pure product (99%).

Step 4 The N-BOC silyl ether from step 3 was treated with acetic acid/water/THF (3:1:1) (0.04M) at 25° C. for 1 d. Workup and chromatographic purification afforded the pure product (100%).

Steps 5 The alcohol from step 4 was dissolved in methylene chloride (0.2M), and under nitrogen at −40° C. treated with triethylamine (1.33 eq), and mesyl chloride (1.23 eq) for 1 h. In a separate dry flask was weighed naphthalene-2-thiol (1.31 eq), and THF (1M) was added, followed by lithium hexamethyldisilazide (1N in THF, 1 eq) and this mixture was stirred at 25° C. for 30 min. The resulting solution was then added dropwise, over 30 minutes, to the above mesylate solution, at −40° C. The reaction mixture was allowed to warm to 25° C., and stirred there for 4.5 h. Workup and chromatographic purification afforded the BOC thioether.

Step 6 The purified BOC thioether from step 5 was heated under nitrogen at 160–170° C. for 1.25 h, and recrystallized from ethyl acetate and hexanes to afford the free indole thioether in 64% yield.

Step 7 The indole thioether from step 6 was dissolved in DMF (0.2M), and treated with sodium hydride (1.1 eq) at 25° C. for 45 min. 4-Chlorobenzyl chloride (1.3 eq) and KI (cat.) were added, and the mixture was stirred at 25° C. for 3 d. Workup (ethyl acetate/water) and trituration (ethyl acetate/hexanes) afforded the pure product (52%).

Step 8 A solution of EtMgBr in ether (3 N, 2.17 eq) was cooled to −70° C. The product of step 7 in scheme 21 (1 eq) in ether (0.55M) was added and the reaction mixture was stirred at −70° C. for 2 h. After the addition of methyl oxalyl chloride (3 eq) in ether (1.5M) the reaction was stirred at −40° C. for 2 h, allowed to warm to 25° C. Quenched with sodium bicarbonate EtOAc/water work up and crystallization from hexane/EtOAc the desired ketone.

Step 9 The ester from step 8 was hydrolyzed using the general method in step 2 example 108 to yield the desired alpha keto acid.

Step 10 The indole thioether from step 9 was dissolved in dry methylene chloride (0.05M), and treated with oxalyl chloride (2.05 eq) at 0° C. for 1 h. In a separate dry flask were weighed 3-aminobenzoic acid (10 eq) and triethylamine (15 eq) in methylene chloride (0.5M). The resulting solution was then added dropwise, at 0° C., and the mixture was allowed to warm to 25° C. overnight. Workup (methylene chloride/aqueous HCl) and repeated purification by chromatography afforded the pure title compound product.

Step 11 The product from step 9 was hydrolyzed using the procedure from step 2 Example 108 to yield the desired compound in 28%. MS: m/z (M−1) 709

EXAMPLE 113

3-[(2-{5-(benzyloxy)-1-methyl-2-[(2-naphthylsulfanyl)methyl]-1H-indol-3-yl}-2-oxoacetyl)amino]benzoic acid Step 1 Following step 4 of the above procedure using methyl iodide followed by trituration (ethyl acetate/hexanes) afforded the pure product (72%).

Step 2 An analogous procedure to step 5 through step 11 above yielded 58% of the title compound. MS: m/z (M−1) 599

EXAMPLE 114

1-benzhydryl-5-[(cyclopentylcarbonyl)amino]-1H-indole-3-carboxylic acid

Step 1 5-nitroindole was alkylated as in Example 3 step 1 with the appropriate bromide to yield the desired N-alkylated product.

Step 2 The indole from step 1 (1.0 eq) was dissolved in DMF (0.4M) and treated with phosporous oxychloride (6.9 eq) at room temperature and then the mixture was stirred for 1 day at 80° C. at which time the reaction was poured onto ice and triturated with ethyl acetate/hexanes, followed by workup with sodium bicarbonate/chloroform yielded the C3 formylated product.

Step 3 The nitro indole from step 2 was reduced according to the procedure in Example 100, step 2 to yield the amino aldehyde.

Step 4 The indole from step 3 was acylated according to the procedure from Example 100, step 3.

Step 5 The indole from step 4 (1.0 eq), 2 methyl-2butene (45 eq), sodium dihydrogen phosphate (11.6 eq). were dissolved in t-BuOH (0.2M), water (0.2M) and then sodium chlorite (11.6 q) was added and the reaction was heated to 65 C. for 24 hours. The reaction was diluted with water, extracted 3 times with ethyl acetate, dried and concentrated and then purified by chromatography to yield the title compound.

EXAMPLE 115

2-1-benzhydryl-5-[(cyclopentylcarbonyl)amino]-1H-indol-3-yl}-2-oxoacetic acid

Step 1 Following the procedure of Example 69, 5-niroindole was acylated in the 3-position with ethylmagnesiumbromide and ethyloxalylchloride.

Step 2 The above intermediate was elaborated to the final product following steps 2–5 of Example 114 to afford the title compound.

EXAMPLE 116

Table I reports data for the compounds described in the examples above in cPLA2 inhibition assays (described below). In the data columns of Tables I and II, assay results are reported as a percent inhibition at the concentration specified.

Coumarin Assay 7-hydroxycoumarinyl 6-heptenoate was used as a monomeric substrate for cPLA2 as reported previously (Huang, Z. et al., 1994, Nalytical Biochemistry 222, 110–115). Inhibitors were mixed with 200 μL assay buffer (80 mM Heped, pH 7.5, 1 mM EDTA) containing 60 μM 7-hydroxycoumarinyl 6-heptenoate. The reaction was initiated by adding 4 μg cPLA2 in 50 μL assay buffer. Hydrolysis of the 7-hydroxycounarimyl 6-heptenoate ester was monitored in a fluorometer by exciting at 360 nm and monitoring emission at 460 nm. Enzyme activity is proportional to the increase in emission at 460 nm per minute. In the presence of a cPLA2 inhibitor, the rate of increase is less. The percent inhibition for corresponding concentrations of compounds herein in this Coumarin assay are provided below in Table I.

TABLE I

| Example | PERCENT INHIBITION @ | CONCENTRATION (micromolar) |
|---|---|---|
| 1 | 7 | 50 |
|  | 18 | 100 |
|  | 50 | 170 |
| 2 | 50 | 25 |
|  | 50 | 32 |
| 3 | 50 | 5 |
|  | 51 | 6.25 |
|  | 50 | 6.4 |
|  | 41 | 10 |
|  | 50 | 17.5 |
|  | 50 | 19 |
|  | 37 | 20 |
|  | 38 | 20 |
|  | 43 | 20 |
|  | 44 | 20 |
|  | 50 | 20 |
|  | 50 | 20 |
|  | 50 | 22 |
|  | 50 | 23 |
|  | 50 | 23.5 |
|  | 50 | 24 |
|  | 39 | 100 |
|  | 50 | 5 |
|  | 51 | 6.25 |
| 4 | 50 | 5 |
|  | 50 | 11 |
|  | 50 | 5 |
|  | 50 | 11 |
| 5 | 41 | 100 |
|  | 50 | 120 |
| 6 | 11 | 100 |
|  | 50 | 200 |
| 7 | 11 | 50 |
|  | 50 | 235 |
| 8 | 50 | 65 |
|  | 44 | 100 |
| 9 | 50 | 13 |
|  | 50 | 19 |
| 10 | 50 | 20 |
|  | 50 | 20 |
|  | 50 | 30 |
|  | 50 | 33.5 |
|  | 50 | 40 |
|  | 50 | 45 |
| 11 | 42 | 10 |
|  | 50 | 12 |
|  | 52 | 12.5 |
|  | 36 | 20 |
|  | 50 | 27.5 |
|  | 50 | 30 |
|  | 50 | 30 |
|  | 50 | 37 |

TABLE I-continued

| Example | PERCENT INHIBITION @ | CONCENTRATION (micromolar) |
|---|---|---|
| 12 | 50 | 0.35 |
|  | 50 | 0.35 |
|  | 50 | 0.38 |
|  | 50 | 0.38 |
|  | 50 | 0.38 |
|  | 50 | 0.39 |
|  | 50 | 0.4 |
|  | 50 | 0.4 |
|  | 50 | 0.4 |
|  | 50 | 0.44 |
|  | 50 | 0.45 |
|  | 64 | 0.5 |
|  | 86 | 1.25 |
| 13 | 50 | 0.39 |
|  | 50 | 0.4 |
|  | 50 | 0.48 |
|  | 50 | 0.55 |
|  | 50 | 0.6 |
|  | 50 | 0.65 |
|  | 50 | 0.65 |
|  | 50 | 0.7 |
|  | 50 | 0.75 |
|  | 50 | 0.95 |
|  | 73 | 2.5 |
|  | 81 | 6.25 |
| 14 | 50 | 0.7 |
|  | 50 | 0.95 |
|  | 50 | 0.95 |
| 15 | 50 | 0.65 |
|  | 50 | 0.65 |
|  | 50 | 0.72 |
|  | 50 | 0.76 |
|  | 50 | 0.85 |
|  | 90 | 6.25 |
| 16 | 50 | 0.125 |
|  | 61 | 0.125 |
|  | 71 | 0.125 |
|  | 50 | 0.14 |
|  | 50 | 0.14 |
|  | 50 | 0.14 |
|  | 50 | 0.17 |
|  | 50 | 0.17 |
|  | 69 | 0.25 |
|  | 98 | 6.25 |
| 17 | 50 | 0.7 |
|  | 50 | 0.8 |
|  | 50 | 0.85 |
|  | 50 | 0.98 |
| 18 | 50 | 1.2 |
|  | 50 | 1.3 |
|  | 50 | 1.9 |
|  | 50 | 2 |
|  | 50 | 2 |
|  | 50 | 2 |
| 19 | 50 | 2.2 |
|  | 50 | 4.2 |
|  | 50 | 5.8 |
|  | 52 | 6.25 |
|  | 50 | 7.8 |
|  | 50 | 9 |
|  | 50 | 11 |
|  | 50 | 12 |
| 20 | 50 | 25 |
|  | 50 | 32 |
| 21 | 50 | 20 |
|  | 50 | 20 |
| 22 | 50 | 38 |
|  | 50 | 40 |
| 23 | 50 | 10 |
|  | 58 | 20 |
| 24 | 42 | 100 |
|  | 50 | 100 |
| 25 | 50 | 13 |
|  | 50 | 17 |
| 26 | 50 | 2.4 |
|  | 50 | 2.5 |
| 27 | 50 | 6 |
|  | 50 | 6.4 |
| 28 | 50 | 4.2 |
|  | 50 | 4.4 |
| 29 | 50 | 2.5 |
|  | 50 | 3.4 |
|  | 87 | 6 |
| 30 | 50 | 8 |
|  | 46 | 20 |
|  | 50 | 21 |
|  | 50 | 24 |
| 31 | 50 | 11 |
|  | 50 | 18 |
| 32 | 50 | 4 |
|  | 50 | 4.4 |
| 33 | 50 | 4.4 |
|  | 50 | 4.9 |
| 34 | 50 | 2 |
|  | 57 | 2.5 |
| 35 | 23 | 10 |
|  | 42 | 20 |
|  | 50 | 41 |
| 36 | 50 | 0.22 |
|  | 60 | 0.25 |
|  | 50 | 0.32 |
|  | 50 | 0.45 |
| 37 | 50 | 0.4 |
|  | 50 | 0.5 |
|  | 50 | 0.55 |
|  | 50 | 0.65 |
| 38 | 50 | 0.3 |
|  | 50 | 0.45 |
|  | 50 | 0.57 |
|  | 50 | 0.59 |
|  | 50 | 0.6 |
|  | 50 | 0.6 |
|  | 50 | 0.6 |
|  | 50 | 0.6 |
|  | 50 | 0.6 |
|  | 50 | 0.64 |
|  | 50 | 0.7 |
|  | 50 | 0.7 |
|  | 50 | 0.85 |
|  | 50 | 0.85 |
|  | 50 | 1 |
|  | 50 | 1 |
| 39 | 50 | 0.39 |
|  | 50 | 0.7 |
|  | 50 | 0.73 |
|  | 50 | 0.75 |
|  | 50 | 0.75 |
|  | 50 | 0.8 |
|  | 50 | 0.9 |
|  | 50 | 0.9 |
|  | 50 | 1 |
|  | 50 | 1 |
|  | 50 | 1.2 |
|  | 50 | 1.3 |
|  | 50 | 1.6 |
| 40 | 50 | 2.5 |
|  | 55 | 2.5 |
|  | 50 | 3 |
|  | 50 | 3.6 |
| 41 | 50 | 2.5 |
|  | 50 | 3.8 |
|  | 50 | 4.3 |
|  | 50 | 5 |
| 42 | 50 | 2.2 |
|  | 50 | 3 |
|  | 50 | 3.8 |
| 43 | 50 | 12 |
|  | 50 | 14 |
| 44 | 50 | 1.65 |
|  | 50 | 1.7 |
|  | 50 | 1.75 |
|  | 50 | 1.9 |

TABLE I-continued

| Example | PERCENT INHIBITION @ | CONCENTRATION (micromolar) |
|---|---|---|
|  | 50 | 2.1 |
|  | 71 | 2.5 |
|  | 97 | 6.25 |
| 45 | 50 | 1.75 |
|  | 50 | 1.8 |
|  | 50 | 1.9 |
|  | 50 | 2 |
|  | 50 | 2.1 |
|  | 74 | 2.5 |
| 46 | 50 | 2.2 |
|  | 67 | 2.5 |
|  | 50 | 2.7 |
|  | 50 | 3.5 |
|  | 50 | 4.5 |
| 49 | 50 | 1.5 |
|  | 50 | 1.8 |
|  | 50 | 2.3 |
| 50 | 50 | 0.8 |
|  | 50 | 0.8 |
|  | 50 | 0.85 |
|  | 50 | 1.05 |
|  | 81 | 2.5 |
| 51 | 50 | 0.6 |
|  | 50 | 0.8 |
|  | 50 | 0.9 |
| 52 | 50 | 19 |
|  | 50 | 19 |
|  | 50 | 20 |
| 53 | 50 | 11 |
|  | 50 | 15.5 |
| 54 | 50 | 2.8 |
|  | 50 | 3.9 |
| 55 | 50 | 1.35 |
|  | 50 | 1.35 |
| 56 | 50 | 0.98 |
|  | 50 | 1.2 |
| 57 | 50 | 1.05 |
|  | 50 | 1.38 |
|  | 50 | 1.4 |
| 58 | 50 | 1.65 |
|  | 50 | 1.65 |
| 59 | 50 | 6 |
|  | 90 | 12.5 |
| 60 | 50 | 12.5 |
| 61 | 50 | 10 |
|  | 54 | 12.5 |
| 62 | 50 | 7 |
|  | 86 | 12.5 |
| 63 | 70 | 2.5 |
|  | 50 | 7 |
| 64 | 50 | 32 |
|  | 50 | 37 |
| 65 | 47 | 50 |
|  | 50 | 72 |
|  | 50 | 80 |
| 66 | 50 | 70 |
|  | 15 | 200 |
|  | 19 | 200 |
| 67 | 8 | 100 |
|  | 31 | 400 |
| 68 | 9 | 100 |
|  | 18 | 400 |
| 69 | 50 | 12.5 |
| 70 | 39 | 50 |
|  | 40 | 50 |
| 71 | 69 | 6 |
|  | 50 | 1.5 |
|  | 50 | 3.5 |
|  | 50 | 3.8 |
| 72 | 50 | 12.5 |
| 76 | 50 | 4 |
| 77 | 50 | 160 |
|  | 50 | 180 |
| 78 | 50 | 80 |
|  | 50 | 110 |
| 79 | 50 | 60 |
|  | 50 | 65 |
| 80 | 50 | 48 |
|  | 60 | 50 |
| 81 | 50 | 70 |
|  | 46 | 100 |
| 82A | 50 | 46 |
|  | 50 | 50 |
| 82B | 61 | 6.25 |
|  | 50 | 6.5 |
| 82C | 50 | 8 |
|  | 50 | 10 |
| 83 | 50 | 48 |
|  | 50 | 70 |
| 84 | 22 | 100 |
|  | 50 | 265 |
|  | 50 | 350 |
| 85 | 31 | 100 |
|  | 50 | 200 |
| 86A | 50 | 60 |
|  | 50 | 70 |
|  | 50 | 82 |
|  | 50 | 118 |
| 86B |  |  |
| 87A | 33 | 50 |
|  | 50 | 95 |
| 87B | 50 | 38 |
|  | 50 | 38 |
|  | 50 | 42.5 |
| 88 | 50 | 1.25 |
|  | 53 | 1.25 |
|  | 50 | 1.32 |
| 89 | 50 | 4.4 |
|  | 50 | 4.8 |
| 90 | 50 | 10.2 |
|  | 50 | 10.5 |
| 91 | 50 | 3.8 |
|  | 50 | 4.25 |
| 92 | 50 | 11 |
|  | 50 | 12.5 |
|  | 50 | 14.2 |
| 93 | 50 | 4.2 |
|  | 50 | 4.9 |
| 94 | 50 | 7 |
|  | 50 | 7.5 |
| 95 | 50 | 11.5 |
|  | 50 | 13 |
| 96 | 50 | 8 |
|  | 50 | 10.5 |
| 97 | 50 | 50 |
|  | 50 | 80 |
|  | 50 | 94 |
| 98 | 50 | 4.8 |
|  | 66 | 6.25 |
|  | 50 | 8.7 |
| 99 | 13 | 30 |
|  | 38 | 100 |
|  | 50 | 100 |
|  | 50 | 100 |
| 100 | 50 | 24 |
|  | 50 | 30 |
|  | 50 | 80 |
| 101 | 6 | 100 |
|  | 49 | 400 |
| 102 | 31 | 20 |
|  | 50 | 48 |
| 103 | 50 | 100 |
|  | 50 | 104 |
| 104 | 50 | 22 |
|  | 50 | 24 |
| 105 | 50 | 2.4 |
|  | 50 | 7 |
|  | 74 | 10 |
| 106 | 50 | 7 |
|  | 50 | 12 |
| 107 | 50 | 80 |
|  | 50 | 71 |

TABLE I-continued

| Example | PERCENT INHIBITION @ | CONCENTRATION (micromolar) |
|---|---|---|
|  | 43 | 50 |
|  | 50 | 37 |
|  | 50 | 37 |
| 108 | 67 | 6.25 |
|  | 15 | 20 |
|  | 50 | 48 |
|  | 46 | 50 |
|  | 46 | 50 |
| 109 | 28 | 50 |
|  | 25 | 50 |
| 110 | 50 | 47 |
|  | 50 | 46 |
| 111 | 16 | 50 |
|  | 15 | 50 |
| 112 | 53 | 2.5 |
| 113 | 50 | 7.5 |
|  | 50 | 8 |
| 114 | 45 | 100 |
|  | 50 | 152 |
|  | 50 | 170 |
| 115 | 89 | 50 |
|  | 20 | 100 |
|  | 50 | 250 |
| 117 | 50 | 1.6 |
| 118 | 50 | 0.6 |
| 119 | 50 | 2.5 |
| 120 | 50 | 1 |
| 121 | 20 | 1.6 |
| 122 | 64 | 1.25 |
| 123 | 50 | 1.2 |
| 124 | 50 | 1.3 |
| 125 | 50 | 0.8 |
| 126 | 50 | 5.5 |
| 127 | 50 | 1.1 |
| 128 | 50 | 0.9 |
| 129 | 50 | 1.1 |
| 130 | 50 | 2 |
| 131 | 50 | 0.6 |
| 132 | 50 | 0.4 |
| 133 | 50 | 0.3 |
| 134 | 50 | 0.8 |
| 135 | 50 | 0.7 |
| 136 | 50 | 0.4 |
| 137 | 50 | 0.8 |
| 138 | 50 | 0.4 |

Compounds of the present invention were also tested for in vivo activity in a rat paw edema test according to the procedure described below. The results are reported in Table II.

Rat Carrageenan-Induced Footpad Edema Test

Each compound was suspended in 0.3 ml absolute ethanol, 0.1 ml Tween-80 and 2.0 ml Dulbecco's PBS (without calcium or magnesium). To this mixture, 0.1 ml 1N NaOH was added. After solution was complete, additional amounts of PBS were added to adjust the concentration to 1 mg/ml. All compounds remained in solution. Compounds were administered i.v. in a volume of 5 ml/kg to male Sprague Dawley rats at the same time that edema was induced by injection of 0.05 ml of 1% Type IV carrageenan into the hind footpad. Footpad volume was measured before dosing with compound and 3 hours after dosing with carageenan.

TABLE II

| Example | ROUTE of ADMIN. | DOSE (mg/Kg) | PERCENT INHIBITION |
|---|---|---|---|
| 1 | IV | 5 | 2.51 |
|  | IV | 5 | 16.61 |
| 2 | IV | 5 | 15.87 |
| 3 | IV | 5 | 10.38 |
|  | PO | 5 | 21.5 |
|  | IV | 5 | 22.84 |
|  | IV | 5 | 14.86 |
|  | PO- | 20 | 19.56 |
|  | IV | 5 | 10.38 |
| 4 | IV | 5 | 24.13 |
|  | IV | 5 | 4.95 |
| 5 | IV | 5 | 8.88 |
|  | IV | 5 | 24.28 |
|  | IV | 5 | 0.09 |
| 7 | IV | 5 | −0.65 |
| 8 | IV | 5 | −5.7 |
| 9 | IV | 5 | 4.46 |
| 10 | IV | 5 | 25.32 |
| 11 | IV | 5 | 13.98 |
| 12 | PO | 2 | 0.19 |
|  | PO | 10 | −0.38 |
| 13 | PO | 2 | 25.99 |
|  | PO | 10 | 23.63 |
| 14 | PO | 2 | 11.53 |
|  | PO | 10 | 8.14 |
| 15 | PO | 2 | 7.05 |
|  | PO | 10 | 6.88 |
| 16 | PO | 2 | 3.8 |
|  | PO | 10 | 14.96 |
| 17 | PO | 2 | 19.29 |
|  | PO | 10 | 34.52 |
| 19 | IV | 5 | 21.17 |
|  | IV | 5 | 13.32 |
|  | IV | 5 | −0.09 |
| 21 | IV | 5 | 16.18 |
|  | IV | 5 | 19.01 |
|  | IV | 5 | 8.66 |
| 22 | IV | 5 | 9.22 |
|  | IV | 5 | 4.14 |
| 23 | IV | 5 | 15.71 |
|  | IV | 5 | 14.45 |
|  | IV | 5 | 2.12 |
| 24 | IV | 5 | 8.33 |
|  | IV | 5 | 16.28 |
|  | IV | 5 | 11.3 |
| 25 | IV | 5 | 2.73 |
|  | IV | 5 | 8.66 |
|  | IV | 5 | 16.02 |
| 26 | IV | 5 | 25.31 |
| 27 | IV | 5 | 6.48 |
| 28 | IV | 5 | 0.29 |
| 30 | IV | 5 | 13.89 |
|  | PO | 2 | −0.11 |
|  | PO | 10 | 13.25 |
| 37 | PO | 2 | −7.94 |
|  | PO | 10 | 3.36 |
| 38 | PO | 2 | 15.44 |
|  | PO | 10 | 26.32 |
| 39 | PO | 2 | 1.98 |
|  | PO | 10 | −7.16 |
| 40 | IV | 5 | 8.21 |
| 41 | IV | 5 | 10.1 |
| 42 | IV | 5 | 7.72 |
| 44 | IV | 5 | 11.9 |
| 45 | IV | 5 | 10.19 |
| 46 | IV | 5 | 4.58 |
| 49 | IV | 5 | 18.02 |
| 50 | PO | 2 | 5.44 |
|  | PO | 10 | 12.34 |
| 51 | PO | 2 | 3.23 |
|  | PO | 10 | 15.37 |
| 52 | PO | 2 | −6.75 |
|  | PO | 10 | 3.33 |
| 53 | PO | 2 | −1.81 |
|  | PO | 10 | 11.35 |
| 54 | PO | 2 | 2.47 |
|  | PO | 10 | 14.29 |
| 55 | PO | 2 | 7.02 |

TABLE II-continued

| Example | ROUTE of ADMIN. | DOSE (mg/Kg) | PERCENT INHIBITION |
|---|---|---|---|
|  | PO | 10 | 21.51 |
| 56 | PO | 2 | 4.22 |
|  | PO | 10 | 9.34 |
| 57 | PO | 2 | 10.44 |
|  | PO | 10 | 20.68 |
| 58 | PO | 2 | 13.85 |
|  | PO | 10 | 9.96 |
| 59 | IV | 5 | 2.9 |
| 61 | IV | 5 | 18.33 |
| 63 | IV | 5 | 19.59 |
| 65 | IV | 5 | 2.84 |
| 66 | IV | 5 | 25.34 |
| 67 | IV | 5 | 10.78 |
| 68 | IV | 5 | −4.3 |
| 76 | IV | 5 | 14.84 |
| 80 | IV | 5 | 10.18 |
| 82B | IV | 5 | 4.94 |
| 84 | IV | 5 | 6.15 |
| 85 | IV | 5 | 7.13 |
| 86A | IV | 5 | 7.4 |
| 87A | PO | 2 | 12.89 |
|  | PO | 10 | 25.44 |
| 87B | PO | 3 | 17.92 |
|  | PO | 10 | 31.4 |
| 89 | PO | 2 | 14.34 |
|  | PO | 10 | 16.38 |
| 90 | PO | 2 | −0.18 |
|  | PO | 10 | 2.7 |
| 91 | PO | 2 | 13.5 |
|  | PO | 10 | 14.67 |
| 92 | PO | 2 | 27.36 |
|  | PO | 10 | 21.34 |
| 93 | PO | 2 | −3.02 |
|  | PO | 10 | 9.91 |
| 94 | PO | 3 | 3.13 |
|  | PO | 10 | 4.46 |
|  | PO | 2 | 19.04 |
|  | PO | 10 | 27.45 |
| 95 | PO | 2 | 14.86 |
|  | PO | 10 | 23.19 |
| 96 | PO | 2 | 29.42 |
|  | PO | 10 | 21.99 |
| 97 | IV | 5 | 21.31 |
| 98 | IV | 5 | 18.39 |
| 99 | PO | 10 | 22.77 |
|  | PO | 2 | 24.51 |
| 100 | PO | 2 | 6.14 |
|  | PO | 10 | 20.7 |
| 101 | PO | 10 | 12.45 |
|  | PO | 2 | 11.17 |
| 102 | PO | 2 | 2.56 |
|  | PO | 10 | 8.48 |
| 103 | PO | 10 | 17.31 |
|  | PO | 2 | 16.5 |
| 104 | PO | 2 | 14.49 |
|  | PO | 10 | 6.01 |
| 105 | IV | 5 | 1.51 |
| 114 | PO | 2 | 12.15 |
|  | PO | 10 | 22.19 |
| 115 | PO | 2 | 1.24 |
|  | PO | 10 | 18.46 |

EXAMPLE 117

2-{4-[(1-benzhydryl-6-chloro-1H-indol-3-yl)
methyl]-2,6-dimethylphenoxy}acetic acid Step 1: To 1-benzhydryl-6-chloro-1H-indole (1.0 eq) and methyl 2-(4-formyl-2,6-dimethylphenoxy)acetate (0.6 eq) in $CH_2Cl_2$ (0.1M) at 0° C. was added neat triethysilane (3 eq) followed by triflouroacetic acid (3 eq). After 10 minutes at 0° C. the reaction was warmed to room temperature and stirred until the initially formed spot by TLC yields a new spot. The reaction was then quenched by the addition of saturated sodium bicarbonate, diluted with $CH_2Cl_2$ and washed with saturated sodium bicarbonate, water and brine, dried over magnesium sulfate and purified by column chromatography to yield 89% of the desired product.

Step 2 The resulting ester was hydrolyzed as in example 1 step 5 to yield the title compound after trituration and/or column chromatography. m/z (M−1)508.3

EXAMPLE 118

2-{4-[(1-benzhydryl-6-chloro-1H-indol-3-yl)
methyl]-3-methoxyphenoxy}acetic acid Step 1: This compound was prepared from the 1-benzhydryl-6-chloro-1H-indole and methyl 2-(4-formyl-3-methoxyphenoxy)acetate according to the procedure in Example 117 Step 1.

Step 2: The ester intermediate was hydrolyzed according to step 2 Example 117 to yield the title acid.

EXAMPLE 119

2-{4-[(1-benzhydryl-6-chloro-1H-indol-3-yl)methyl]
phenoxy}acetic acid

Step 1: This compound was prepared from the 1-benzhydryl-6-chloro-1H-indole and methyl 2-(4-formylphenoxy)acetate according to the procedure in Example 117 Step 1.

Step The ester intermediate was hydrolyzed according to step 2 Example 117 to yield the title acid.

EXAMPLE 120

2-{4-[(1-benzhydryl-6-chloro-1H-indol-3-yl)
methyl]-3-chlorophenoxy}acetic acid

Step 1: This compound was prepared from the 1-benzhydryl-6-chloro-1H-indole and methyl 2-(3-chloro-4-formylphenoxy)acetate according to the procedure in Example 117 Step 1 in 70% yield.

Step 2: The ester intermediate was hydrolyzed according to step 2 Example 117 to yield the title acid.

EXAMPLE 121

2-{4-[(1-benzhydryl-6-chloro-1H-indol-3-yl)
methyl]-2-methoxyphenoxy}acetic acid Step 1: This compound was prepared from the 1-benzhydryl-6-chloro-1H-indole and methyl 2-(4-formyl-2-methoxyphenoxy)acetate according to the procedure in Example 117 Step 1 in 71% yield.

Step 2: The ester intermediate was hydrolyzed according to step 2 Example 117 yield the title acid. m/z (M−1)510.2

EXAMPLE 122

(E)-4-{4-[(1-benzhydryl-6-chloro-1H-indol-3-yl)
methyl]phenoxy}-2-butenoic acid

Step 1: This compound was prepared from the 1-benzhydryl-6-chloro-1H-indole and (E)-4-(4-formylphenoxy)-2-butenoate according to the procedure in Example 117 Step 1 in 91% yield.

Step 2: The ester intermediate was hydrolyzed according to step 2 Example 117 to yield the title acid. m/z (M−1)506.3

EXAMPLE 123

4-{4-[(1-benzhydryl-6-chloro-1H-indol-3-yl)methyl]
anilino}-4-oxobutanooic acid

Step 1 This intermediate compound was prepared from the 1-benzhydryl-6-chloro-1H-indole and 4-nitrobenzaldehyde according to the procedure in Example 117 Step 1 in 42% yield.

Step 2-benzhydryl-6-chloro-3-(4-nitrobenzyl)-1H-indole was reduced by dissolving in THF (0.1M), subjecting it to 1 atmosphere of hydrogen gas in the presence of 10% platinum on carbon catalyst (25% w/w). When the starting material had all been converted to a new spot by TLC analysis the reaction was filtered and concentrated to yield the desired intermediate in nearly quantitative yield.

Step 3: To the intermediate above (1.0 eq) in $CH_2Cl_2$ (0.1M) at 0° C. was added triethylamine (1.5 eq) followed by 3-carbomethoxyproprionyl chloride(1.5 eq). The reaction was warmed to room temperature, stirred until complete disappearance of starting material as monitored by TLC, and then worked by the addition of saturated sodium bicarbonate, dilution with $CH_2Cl_2$, and washing the organic layer with water, saturated sodium bicarbonate and brine, dried, concentration and purified by column chromatography to yield the desired compound in 81% yield.

Step 4: The ester from step 3 was then hydrolyzed according to step 2 Example 117 to yield the title acid. m/z (M−1)521.3

EXAMPLE 124 sodium 3-{4-[(1-benzhydryl-6-chloro-1H-indol-3-yl)methyl]anilino}-3-oxopropanoic acid Step 1 The intermediate from example 117, step 1 was acylated with methyl malonyl chloride according to the procedure for step 1 of Example 117 in 82% yield.

Step 2 The ester was hydrolyzed according to step 2 for Example 123 to yield the title compound. m/z (M−1)507.2

EXAMPLE 125

2-{4-[(1-benzhydryl-6-chloro-1H-indol-3-yl)methyl]anilino}-2-oxoacetic acid

Step 1 The intermediate from example 117, step 1 was acylated with methyl oxalyl chloride according to the procedure for step 1 of Example 117 in 67% yield.

Step 2 The ester was hydrolyzed according to step 2 for Example 117 to yield the title compound. m/z (M−1)493.2

EXAMPLE 126

2-[(1-benzhydryl-6-chloro-1H-indol-3-yl)methyl]cyclopropanecarboxylic acid

Step 1: This intermediate compound was prepared from the 1-benzhydryl-6-chloro-1H-indole and ethyl 2-formyl-1-cyclopropanecarboxylate according to the procedure in Example 117 Step 1 in 53% yield.

Step 2: The ester was hydrolyzed according to step 2 for Example 117 to yield the title compound in 93% yield. m/z (M−1)1414.2

EXAMPLE 127

2-[(1-benzhydryl-6-chloro-5-fluoro-1H-indol-3-yl)methyl]cyclopropanecarboxylic acid Step 1: 6-chloro-5-flouroindole was N-alkylated with benzhydryl bromide according to the procedure in Example 69 step 2 to yield the target intermediate.

Step 2: The product from step 1 was C3 acylated with ethyl 2-formyl-1-cyclopropanecarboxylate according to the procedure in Example 117 Step 1 in 53% yield.

Step 3: The ester was hydrolyzed according to step 2 for Example 117 to yield the title compound in 73% yield. m/z (M−1)432.2

EXAMPLE 128

2-[(1-benzhydryl-5,6-dichloro-1H-indol-3-yl)methyl]cyclopropanecarboxylic acid

Step 1: 5,6-dichloroindole was N-alkylated with benzhydryl bromide according to the procedure in Example 69 step 2 to yield the target intermediate in 70% yield.

Step 2: The intermediate from step 1 was C3 acylated with ethyl 2-formyl-1-cyclopropanecarboxylate according to the procedure in Example 117 Step 1 in 62% yield.

Step 3: The ester was hydrolyzed according to step 2 for Example 117 to yield the title compound in 73% yield. m/z (M−1)448.2

EXAMPLE 129

2-({1-[bis(4-hydroxyphenyl)methyl]-6-chloro-1H-indol-3-yl}methyl)cyclopropanecarboxylic acid Step 1: 6-chloroindole was C3 alkylated with ethyl 2-formyl-1-cyclopropanecarboxylate according to the procedure in Example 117 Step 1.

Step 2: The intermediate from step 1 (2.0 eq.) was dissolved in THF (0.5M) and cooled to −40° C. and then triethylamine (2.0 eq) was added followed by methanesulfonyl chloride (2.0 eq). The reaction was stirred at this temperature until TLC analysis indicated no more starting alcohol, and then it was cannulated directly into a mixture of the c3 alkylated indole from step 1 (1.0 eq) in DMF (1.0M) at −20° C. that had been stirred for 30 minutes at room temperature with sodium hydride (4.0 eq of a 60% dispersion). The resulting mixture was warmed to room temperature overnight and quenched when the reaction was deemed complete by the addition of saturated ammonium chloride, diluted with ethyl acetate and washed with saturated ammonium chloride, saturated sodium bicarbonate and water (2x), dried, concentrated and purified by column chromatography.

Step 3: The intermediate from step 2 was dissolved in THF (1.0M) and treated with a solution of tetrabutylammonium flouride (2.5 eq) and stirred at room temperature until TLC analysis indicates that both silyl ethers had been cleaved. The reaction was then poured into saturated ammonium chloride and extracted with ethyl acetate (3x), the combined organic washed were washed with water, brine, dried and concentrated and purified by column chromatography to yield the intermediate in 73% yield.

Step 4: The ester from step 3 was hydrolyzed according to step 2 for Example 123 to yield the title compound in 92% yield. m/z (M−1)447.12

EXAMPLE 130

'4-[(1-benzhydryl-6-chloro-1H-indol-3-yl)methyl]-3-hydroxybenzoic acid

Step 1: This compound was prepared from the 1-benzhydryl-6-chloro-1H-indole and 4-hydroxy-2-methoxybenzaldehyde according to the procedure in Example 117 Step 1.

Step 2: The ester was hydrolyzed according to step 2 for Example 117 to yield the title compound

EXAMPLE 131

'4-[(1-benzhydryl-6-chloro-1H-indol-3-yl)methyl]-3-(3-hydroxypropoxy)benzoic acid Step 1: The intermediate from Example 130, step 1, was dissolved in DMF (1.0M), solid potassium carbonate (3 eq)

followed by 2-(3-bromopropoxy)tetrahydro-2H-pyran (1.5 eq) was added and the reaction was left to stir for 24 hours at room temperature. The workup consisted of diluting with half saturated ammonium chloride and ethyl acetate, extracting aqueous layer with ethyl acetate (2x), washing the organic layer with water (2x), drying, concentration followed by purification via column chromatography.

Step 2: The intermediate from step 1 was dissolved in THF (1.0M), treated with glacial acetic acid (2.0 eq) and heated at 45° C. for 24 hours, at which time the reaction was partitioned between saturated sodium bicarbonate and ethyl acetate, the combined organic layers where washed with water (2x), dried, concentrated and purified by column chromatography to yield 88% of the desired compound.

Step 3: The ester was hydrolyzed according to step 2 for Example 123 to yield the title compound. m/z (M−1)524.3

EXAMPLE 132

'4-({1-[(4-aminophenyl)(phenyl)methyl]-6-chloro-1H-indol-3-yl}methyl)-3-methoxybenzoic acid Step 1: This compound was prepared from 6 chloroindole and methyl 2-(4-formyl-2-methoxyphenoxy)acetate according to the procedure in Example 117 Step 1 in 61% yield.

Step 2: The intermediate from step 1 was N-alkylated according to the procedure for Example 129, step 2, with tert-butyl N-{4-[hydroxy(phenyl)methyl]phenyl }carbamate.

Step 3: The nitrogen protection was removed by heating the compound to 180° C. to yield 45% of the desired amino ester.

Step 4: The intermediate from step 3 was hydrolyzed following step 2 for Example 117 to yield the title compound in 78% yield. m/z (M−1)495.2

EXAMPLE 133

'4-({6-chloro-1-[(4-methoxyphenyl)(phenyl)methyl]-1H-indol-3-yl}methyl)-3-methoxybenzoic acid Step 1: The intermediate from Example 132, step 1, (1.0 eq) was dissolved in DMF (1.0M), cooled to 0° C., and treated with sodium hydride (1.5 eq) and stirred for 30 minutes to affect deprotonation. The 1-[bromo(phenyl)methyl]-4-methoxybenzene (1.5 eq), as a solution in DMF (2.0M), was added to the anion and the reaction was warmed to room temperature, when the reaction was deemed complete by TLC analysis it was partitioned between ethyl acetate and half saturated ammonium chloride, extracting the aqueous layer with ethyl acetate (2x), washing the organic layer with water (2x), drying, concentration followed by purification via column chromatography yielded the desired intermediate.

Step 2: The intermediate from step 1 was hydrolyzed following step 2 for Example 117 to yield the title compound. m/z (M−1)510.2

EXAMPLE 134

'4-({1-[bis(4-methoxyphenyl)methyl]-6-chloro-1H-indol-3-yl}methyl)-3-methoxybenzoic acid Step 1: The intermediate from Example 132 was N-alkylated with 1-[bromo(4-methoxyphenyl)methyl]-4-methoxybenzene according to the procedure described in Example 133, step 1, to yield the desired intermediate.

Step 2: The intermediate from step 1 was hydrolyzed following step 2 for Example 117 to yield the title compound. m/z (M−1)540.3

EXAMPLE 135

'4-({6-chloro-1-[(2-morpholinophenyl)(phenyl)methyl]-1H-indol-3-yl}methyl)-3-methoxybenzoic acid Step 1: The intermediate from Example 132 was N-alkylated according to the procedure for Example 129, step 2, with the appropriate electrophile.

Step 2: The intermediate form step 1 was hydrolyzed following step 2 for Example 117 to yield the title compound.

EXAMPLE 136

4-({6-chloro-1-[(2,4-dimethoxy-5-pyrimidinyl)(phenyl)methyl]-1H-indol-3-yl}methyl)-3-methoxybenzoic acid Step 1: The intermediate from Example 132 was N-alkylated according to the procedure for Example 129, step 2, with the appropriate electrophile to yield the desired intermediate in 16% yield.

Step 2: The intermediate from step 1 was hydrolyzed following step 2 for Example 117 to yield the title compound. m/z (M−1)542.3

EXAMPLE 137

'4-[(1-benzhydryl-6-chloro-1H-indol-3-yl)methyl]-3-methoxybenzoic acid

Step 1: This compound was prepared from the 1-benzhydryl-6-chloro-1H-indole and the appropriate aldehyde according to the procedure in Example 117 Step 1.

Step 2: The intermediate from step 1 was hydrolyzed following step 2 for Example 117 to yield the title compound. m/z (M−1)481.14

EXAMPLE 138

2-({4-[(1-benzhydryl-6-chloro-1H-indol-3-yl)methyl]-3-methoxybenzoyl}amino)acetic acid Step 1: The intermediate from Example 137, step 2, treated with glycine ethyl ester according to the procedure in Example 76 to yield the desired ester.

Step 2: The intermediate from step 1 was hydrolyzed following step 2 for Example 117 to yield the title compound. m/z (M−1)537.2

EXAMPLE 139

4-{[2-(1-benzhydryl-5-fluoro-2-methyl-1H-indol-3-yl)ethyl]sulfonyl}benzoic acid

Step 1: 2.0 g of 4-fluorophenylhydrazine hydrochloride (0.0123M, 1.0 eq.) and 0.714 g of acetone (0.0123M, 1.0 eq.) were dissolved in 20 mL of methylene chloride. To this 20 mL of a saturated solution of sodium bicarbonate was added and the two phase mixture was stirred vigorously for 16 hrs. TLC indicated a new spot at .Rf of +0.3 in 3:1 hexanes/ethyl acetate and no remaining starting indole. The two phase mixture was separated and the organic layer evaporated to dryness after drying over magnesium sulfate. The residue was co-evaporated with 25 mL of benzene to azeotrope any remaining water and this material was used in step 2 without any further purification.

Step 2: The residue from step 1 was dissolved in 50 mL of anhydrous methylene chloride. To the solution 2.0 g of zinc (II) chloride (0.0147M, 1.2 eq.) and the suspension was evaporated to dryness. The residue was then heated at 140° for 6 hrs. TLC indicated consumption of the product from step 1 and a new spot had formed at .Rf of +0.2. The reaction was cooled to room temperature and the residue partitioned between ethyl acetate (1000 mL) and water (75 mL). The organic layer was washed with water (50 mL), and brine (2×50 mL). The organic layer was separated, dried over magnesium sulfate and evaporated to dryness. The residue was purified via column chromatography (hexanes/ethyl acetate 9:1) to result in isolation of 750 mg of the title compound (41% yield).

Step 3: 750 mg of 5-fluoro-2-methyl-1H-indole (0.005M, 1.0 eq.) was dissolved in 10 mL of THF and cooled to −78° in a dry ice-acetone bath. 2.4 mL of a 2.5M solution of n-butyl lithium in hexanes (0.006M, 1.2 eq.) was added dropwise. After addition was complete the reaction was stirred for 30 min at −78°. Then 5.0 mL of a 1.0M solution of zinc (II) chloride in ethyl ether(0.005M, 1 eq.) was added rapidly. Once addition was complete the cooling bath was removed and the reaction warmed to room temperature. Once the reaction reached ambient temperature 1.13 g of methyl 4-vinylsulfonylbenzoate (0.005M, 1 eq.) dissolved in 10 mL of tetrahydrofuran was added and stirring continued for 1 hr after addition. TLC indicated a new spot at .Rf of −0.4 relative to starting indole in 3:1 hexanes/ethyl acetate. The reaction was quenched with 1 mL of saturated ammonium chloride solution, then diluted with 75 mL of ethyl acetate. The solution was washed with brine (2×50 mL), dried over magnesium sulfate and evaporated to a beige oil. The oil was purified via column chramatography (hexanes/ethyl acetate, 3:1) to result in isolation of 450 mg of a yellow solid (45% yield).

Step 4: The material from step 1 was alkylated with benzhydryl bromide as in Example 69 Step 2 To yield the ester of the title compound after column chromatography.

Step 5: The material from step 4 was hydrolyzed according to step 2 Example 117 to yield the title acid m/z (M−1) 526.

EXAMPLE 140

4-{[2-(1-benzhydryl-6-chloro-2-methyl-1H-indol-3-yl)ethyl]sulfonyl}benzoic acid

Step 1: The hydrazone intermediate was prepared from 3-chlorophenylhydrazine hydrochloride and acetone as described in step 1 Example 139.

Step 2: The hydrazone intermediate from step 1 was converted to the title indole as described in step 2 Example 139.

Step 3: This intermediate was made from 6-chloro-2-methyl-1H-indole according to the procedure in step 3 Example 139.

Step 3: The material from step 3 was alkylated with benzhydryl bromide as in Example 69 Step 2 to yield the ester of the title compound after column chromatography.

Step 5: The material from step 4 was hydrolyzed according to step 2 Example 117 to yield the title acid m/z (M−1) 542.

EXAMPLE 141

4-{[2-(1-benzhydryl-4,5-dichloro-2-methyl-1H-indol-3-yl)ethyl]sulfonyl}benzoic acid Step 1: The hydrazone intermediate was prepared from 3,4-dichlorophenylhydrazine hydrochloride and acetone as described in step 1 Example 1.

Step 2: The hydrazone intermediate from step 1 was converted to the title indole as described in step 2 Example 1.

Step 3: This intermediate was made from 4,5-dichloro-2-methyl-1H-indole according to the procedure in step 3 Example 139.

Step 4: The material from step 1 was alkylated with benzhydryl bromide as in Example 69 Step 2 to yield the ester of the title compound after column chromatography.

Step 5: The material from step 4 was hydrolyzed according to step 2 Example 117 to yield the title acid m/z (M−1) 574.

EXAMPLE 142

4-{[2-(1-benzhydryl-5,6-dichloro-2-methyl-1H-indol-3-y[)ethyl]sulfonyl}benzoic acid Step 1: The hydrazone intermediate was prepared from 3,4-dichlorophenylhydrazine hydrochloride and acetone as described in step 1 Example 139.

Step 2: The hydrazone intermediate from step 1 was converted to the title indole as described in step 2 Example 139.

Step 3: This intermediate was made from 5,6-dichloro-2-methyl-1H-indole according to the procedure in step 3 Example 139.

Step 4: The material from step 3 was alkylated with benzhydryl bromide as in Example 69 Step 2 to yield the ester of the title compound after column chromatography.

Step 5: The material from step 4 was hydrolyzed according to step 2 Example 117 to yield the title acid m/z (M−1) 574.

EXAMPLE 143

4-{[2-(1-benzhydryl-2-methyl-1H-indol-3-yl)ethyl]sulfonyl}benzoic acid

Step 1: 2-methylindole was reacted with methyl 4-vinylsulfonylbenzoate according to step 3 for Example 139 to yield the desired product in 73 yield.

Step 2 The intermediate from step 2 was alkylated with benzhydryl bromide according to Example 69, step 2 to yield the requisite compound in 25% yield Step 3 The intermediate from step 2 was hydrolyzed according to step 2 of example 117 to yield the title compound in 30% yield, m/z (M−1) 508.2.

EXAMPLE 144

4-{[2-(1-benzhydryl-5-methoxy-2-methyl-1H-indol-3-yl)ethyl]sulfonyl}benzoic acid Step 1: 5-methoxy-2-methylindole was reacted with methyl 4-vinylsulfonylbenzoate according to step 3 for Example 139 to yield the desired product in 62% yield.

Step 2 The intermediate from step 2 was alkylated with benzhydryl bromide according to Example 69, step 2 to yield the requisite compound in 23% yield.

Step 3 The intermediate from step 2 was hydrolyzed according to step 2 of example 117 to yield the title compound in 56% yield, m/z (M−1) 538.2.

EXAMPLE 145

4-[2-(1-benzhydryl-5-bromo-2-methyl-1H-indol-3-yl)ethoxy]benzoic acid

Step 1: To 4-bromophenylhydrazine hydrochloride(1.0 eq.) in dichloromethane (0.44M) at room temperature was added an equal amount of saturated sodium bicarbonate followed by ethyl leviolinate (1.0 eq.). The reaction stirred for 3 hours. The mixture was diluted with ethyl acetate until the organic layer became the top layer. The layers were separated and the organic layer was washed with water and brine, dried over magnesium sulfate and concentrated to yield the desired product and a small amount of side product in a combined 92% yield.

Step 2: The resulting hydrazone intermediate (1.0 eq) and solid $ZnCl_2$ (1.5 eq) were taken up in dichlormethane (0.20M) and swirled for 15 minutes. The solvent was removed under vacuum and the remaining material was heated to 140° C. and monitored by TLC. Upon completion the heat was removed and ethyl acetate was added to the reaction vessel. The organic material was washed with saturated sodium bicarbonate, dried over magnesium sulfate and concentrated to yield 65% of the desired product.

Step 3: To the resulting indole intermediate (1.0 eq.) in DMF (0.20M) at 0° C. was added NaH (1.25 eq.). After stirring for 15 minutes a solution of benzhydryl bromide (1.1 eq.) in DMF (0.23M) was added. Upon disappearance of starting material as monitored by TLC the mixture as diluted with ethyl acetate, washed with water and brine, dried over magnesium sulfate, concentrated and purified by column chromatography to yield 72% of the desired product.

Step 4: To the resulting indole intermediate (1.0 eq.) in THF (0.04M) at 0° C. was added a 1.0M solution of $LiAlH_4$ (2.0 eq.). Following the disappearance of starting material as monitored by TLC the reaction was worked up in the following manner, n mL water, n mL 15% NaOH, n mL water where n is grams $LiAlH_4$. Following each addition the mixture stirred for 5 minutes. Magnesium sulfate was added followed by filtration and concentrated to yield 95% of the desired product.

Step 5: The resulting indole intermediate (1.0 eq.), 4-methoxy benzoate (1.0 eq.) and resin bound triphenylphosphine (1.5 eq) were taken up in dichlormethane (0.03M). After stirring at room temperature for one hour DIAD was added (1.1 eq.). Upon disappearance of starting material, as monitored by TLC, the reaction mixture was filtered. The filtrate was washed with water, brine, dried over magnesium sulfate, concentrated and purified by column chromatography to yield 74% of the desired product.

Step 6. The resulting ester intermediate was hydrolyzed according to step 2 example 117 to give the title acid in 93% yield m/z (M−1) 538.2

EXAMPLE 146

4-{[2-(1-benzhydryl-5-chloro-2-methyl-1H-indol-3-yl)ethyl]sulfany}benzoic acid

Step 1—To 4-Mercaptobenzoic acid(1.0 eq) in DMF (0.32M) was added $K_2CO_3$ (2.0 eq) followed by bromoacetaldehyde diethyl acetal (1.0 eq), and the reaction mixture was stirred overnight at 25° C. TLC showed a new spot. The reaction mixture was diluted with ethyl acetate, washed with water, and brine, and the solvent was removed. Trituration with 20% ethyl acetate in hexanes gave the desired product in 81% yield.

Step 2—To the above compound (1.0 eq) in $CH_2Cl_2$ (0.24M) was added DMF followed by oxalyl chloride (1.1 eq). After stirring for 2 h at 25° C., $Et_3N$ (2.0 eq) and MeOH (3.0 eq) were added, and stirring was continued. The reaction was monitored by TLC. After all the starting material was consumed, the solvent was evaporated to yield 96% of the requisite product.

Step 3—To the compound from step 3 (1.0 eq) in $CHCl_3$ (0.32M) was added 2O (2.0 eq) followed by the dropwise addition of trifluoroacetic acid (2.0 eq). The reaction mixture was stirred at room temperature overnight. TLC showed the disappearance of the starting material. The reaction mixture was diluted with chloroform, washed with saturated sodium bicarbonate, and brine, and dried over sodium sulfate. The solvent was evaporated to give the aldehyde in 76% yield.

Step 4—To 5-chloro-2-methylindole (1.0 eq) in DMF (0.36M) at 0° C. was added NaH (1.2 eq, 60%), and the brown solution was stirred at 0 to −5° C. for 1 h. Benzhydryl bromide (1.1 eq) was added, and the reaction mixture was allowed to come to 25° C. and stirred overnight. The reaction was then quenched with water, diluted with ethyl acetate, washed with water, and brine, dried over sodium sulfate, and purified by column chromatography to yield 25% of the desired product.

Step 5—To a mixture of the product of step 4 (1.0 eq) and the product of step 3 (1.06 eq) in $CH_2Cl_2$ (0.06M) at 0° C. was added triethylsilane (3.0 eq) followed by trifluoroacetic acid (3.0 eq). After being stirred at 0° C. for 1 h, the reaction mixture was quenched with saturated sodium bicarbonate, diluted with $CH_2Cl_2$, washed with water and brine, and dried over sodium sulfate and purified by column chromatography to yield 25% of the desired product.

Step 6—The ester 9 (1.0 eq) was hydrolyzed following Example 117, step 2 to yield the title compound in 78% yield after trituration.

EXAMPLE 147

4-{[2-(1-benzhydryl-5-chloro-2-methyl-1H-indol-3-yl)ethyl]sulfonyl}benzoic acid

Step 1—To the product of step 6, Example 146 (1.0 eq) in acetone, methanol and water (0.3M), was added oxone (1.0 eq). After being stirred 1 d at 25° C., the reaction mixture was diluted with $CHCl_3$, washed with water and brine, and dried over sodium sulfate and purified by column chromatography to give both the sulfone (36%) and the sulfoxide (29%).

Step 2—The sulfone from step 1 was hydrolyzed according to the procedure of step 2, Example 117 to yield the title compound in 79% yield after trituration.

EXAMPLE 148

4-{[2-(1-benzhydryl-5-chloro-2-methyl-1H-indol-3-yl)ethyl]sulfinyl}benzoic acid

Step 1—The sulfoxide from step 1, Example 147, was hydrolyzed according to the procedure of step 2, Example 117 to yield the title compound in 80% yield after trituration.

EXAMPLE 149

4-[2-(1-benzhydryl-5-chloro-2-methyl-1H-indol-3-yl)ethoxy]benzoic acid

Step 1—To methyl 4-hydroxybenzoate(1.0 eq) in DMF (0.83M) was added $K_2CO_3$ (2.0 eq) followed by bromoacetaldehyde diethyl acetal (1.0 eq) and the reaction mixture was stirred at 110° C. for 2 days. TLC showed a new spot. The reaction mixture was diluted with ethyl acetate, washed with 1N NaOH, water, and brine, dried over sodium sulfate, and solvent was removed to afford the product in 84% yield. This material was used in the next step without further purification.

Step 2—To the product of step 1 (1.0 eq) and 5-chloro-2-methyl indole (1.0 eq) in $CH_2Cl_2$ (0.12M) was added triethylsilane (3.0 eq) followed by trifluoroacetic acid (3.0 eq). After being stirred overnight at room temperature, added water and trifluroacetic acid (1.0 eq) to the reaction mixture, stirred at room temperature for two days, diluted with $CH_2Cl_2$, washed with 1N NaOH, water, brine, dried over sodium sulfate. Trituration of the material with $CH_2Cl_2$ and hexanes afforded the desired product in 92% yield Step 3—To the product from step 3(1.0 eq) in DMF (0.36M) at 25° C. was added NaH (1.2 eq, 60% dispersion in oil), and the brown solution was stirred at 0 to –5° C. for 1 h and then benzhydryl bromide was added (1.1 eq), and then the reaction mixture was stirred overnight. It was then quenched with water, diluted with ethyl acetate, washed with water and brine, dried over sodium sulfate and purified by column chromatography to yield 72% of the requisite product.

Step 4—The ester from above (1.0 eq) was hydrolyzed according to the procedure in Example 117, step 2 to give the title compound in 80% yield after trituration.

EXAMPLE 150

4-[2-(1-benzhydryl-5-chloro-2-formyl-1H-indol-3-yl)ethoxy]benzoic acid

Step 1—To the product of step 3, Example 149 (1.0 eq) in $CCl_4$ (0.2M) was added N-bromosuccinimide (2.0 eq) and a catalytic amount of benzoyl peroxide. The solution was heated to reflux for 3 h, cooled to 25° C., filtered, and the solid was washed with $CCl_4$. The filtrate was concentrated to a foam, which was dried. The foam was dissolved in acetone, and $Ag_2CO_3$ (1.1 eq.) was added followed by water and the reaction mixture was stirred overnight at room temperature. It was filtered and washed with acetone. The filtrate was concentrated to a residue, to which was added water. This mixture was extracted with ethyl acetate, washed with brine, dried over sodium sulfate and then chromatographic purification on the residue gave the desired product in 85% yield.

Step 2—The compound from step 1 was hydrolyzed according to Example 117, step 2 to yield the title compound in 78% yield after trituration.

EXAMPLE 151

4-{2-[1-benzhydryl-5-chloro-2-(hydroxymethyl)-1H-indol-3-yl]ethoxy}benzoic acid

Step 1—To a solution of the product from step 1, Example 150 (1.0 eq) in THF and MeOH (0.033M) was added $NaBH_4$ (5.0 eq), and the reaction mixture was stirred overnight at 25° C. The reaction mixture was quenched with 1N HCl and water, diluted with ethyl acetate, washed with brine, and dried over sodium sulfate. Chromatographic purification afforded the desired alcohol in 99% yield.

Step 2—The compound from step 1 was hydrolyzed according to Example 117, step 2 to yield the title compound in 99% yield after trituration.

EXAMPLE 152

4-{2-[1-benzhydryl-5-chloro-2-(methoxymethyl)-1H-indol-3-yl]ethoxy}benzoic acid

Step 1—To the product from step 1, Example 151 (1.0 eq) in dichloroethane (0.023M) was added methanesulfonyl chloride (1.3 eq) and triethylamine (1.6 eq), and the reaction mixture was stirred at 25° C. for 2 h. Methanol and triethylamine (10 eq) were added to the reaction mixture and it was then heated to reflux overnight. Solvent was removed, and the residue was dissolved in ethyl acetate, washed with saturated sodium bicarbonate, brine, and dried over sodium sulfate. Evaporation of the solvent provided the desired ether in 100% yield.

Step 2—The compound from step 1 was hydrolyzed according to Example 117, step 2 to yield the title compound in 91% yield after trituration.

EXAMPLE 153

4-(2-{1-benzhydryl-5-chloro-2-[(phenylsulfonyl)methyl]-1H-indol-3-yl}ethoxy)benzoic acid Step 1—To the product from step 1, Example 151 (1.0 eq) in dichloroethane (0.023M) was added methanesulfonyl chloride (1.3 eq) and triethylamine (1.6 eq), and the reaction mixture was stirred at 25° C. for 2 h. Triethylamine (5.0 eq) and thiophenol (2.2 eq) were added, and the reaction mixture was heated at reflux overnight. The reaction was then washed with 1N NaOH, water, and brine, dried over sodium sulfate and purified by column chromatography to yield 56% of the desired product.

Step 2—To the compound from step 1 (1.0 eq) in acetonitrile (0.02M) was added powdered molecular sieves, followed by N-methyl morpholine N-oxide (NMO) (3.0 eq), and the mixture was stirred for a few minutes. TPAP (tetrapropylammonium perruthenate, 0.1 eq) was added, and the mixture was stirred at 25° C. for 0.5 hr and then at 50° C. overnight. Solvent was removed and column chromatographic purification provided the desired product in 94% yield.

Step 3—The compound from step 2 was hydrolyzed according to Example 117, step 2 to yield the title compound in 80% yield after trituration.

EXAMPLE 154

4-(2-{1-benzhydryl-5-chloro-2-[(methylsulfonyl)methyl]-1H-indol-3-yl}ethoxy)benzoic acid Step 1—To the product from step 1, Example 151 (1.0 eq) in dichloroethane (0.023M) was added methanesulfonyl chloride (1.3 eq) and triethylamine (1.6 eq), and the reaction mixture was stirred at 25° C. for 2 h. The solvent was removed and the residue was dissolved in DMF. NaSMe (2.2 eq) was added, and the reaction mixture was stirred at 25° C. overnight. It was diluted with ethyl acetate, washed with 1N NaOH, water and brine, dried over $Na_2SO_4$ and purified by column chromatography to afford thje requisite product in 71% yield.

Step 2—To the product of step 1 (1.0 eq) in acetonitrile (0.016M) was added powdered molecular sieves, followed by N-methyl morpholine N-oxide (NMO) (3.0 eq), and the mixture was stirred for a few minutes. TPAP (tetrapropylammonium perruthenate, 0.1 eq) was added, and the mixture was stirred at 25° C. for 0.5 hr and then at 50° C. overnight. Solvent was removed and column chromatographic purification provided the desired product in 80% yield.

Step 3—The compound from step 2 was hydrolyzed according to Example 117, step 2 to yield the title compound in 91% yield after trituration.

EXAMPLE 155

4-[2-(1-benzhydryl-5-chloro-2-{[(2-nitrobenzyl)oxy]methyl}-1H-indol-3-yl)ethoxy]benzoic acid Step 1—To a solution of the product of step 1, Example 151 (0.28 mmol) in 1,2-dichloroethane (3 mL) under argon, was added methane sulfonyl chloride (0.31 mmol) and triethylamine (0.34 mmol). The resulting solution was stirred at ambient temperature for 3 hours. 2-nitrobenzyl alcohol (0.86 mmol) and triethylamine (0.86 mmol) were added and the reaction heated at 65° C. The reaction was monitored by TLC. After 48 hours, the reaction was diluted with water and extracted with dichloromethane, washed with brine, dried over sodium sulfate, and solvent removed via rotary evaporation. The residue was purified via flash chromatography on silica gel eluting with 8–15% ethyl acetate in hexane to yield 37% of desired product.

Step 2—The product from step 1 was stirred in a 3:1:1 mixture of tetrahydrofuran, methanol, and 1N lithium hydroxide at 40° C. for 24 hours. The solution was diluted with water, extracted with ethyl acetate, washed with brine, and dried over sodium sulfate. The residue was purified via prep TLC eluting with 30% ethyl acetate in hexane with 0.1% acetic acid to yield 20% of the title compound. m/z (M+1) 648.1

EXAMPLE 156

4-[2-(1-benzhydryl-5-chloro-2-{[(2,6-difluorobenzyl)oxy]methyl}-1H-indol-3-yl)ethoxy]benzoic acid Step 1—This compound was prepared from analogously to step 1 of example 155 using 2,6-difluorobenzyl alcohol and it yielded the desired product in a quantitative yield.

Step 2—The product from above was treated as in step 2 of example 155 to yield 50% of the title compound. m/z (M−1) 639.1.

EXAMPLE 157

4-({2-[1-benzhydryl-5-chloro-2-(hydroxymethyl)-1H-indol-3-yl]ethyl}sulfonyl)benzoic acid Step 1: Ethyl 5-chloro-2-indole-carboxylate (1 eq) was dissolved in THF (0.45M) under $N_2$. This solution was cooled to 0° C. for fifteen minutes and then 1.1 eq LiAlH$_4$ (1M in THF) was added. The resulting dark brown solution was allowed to return to rt with stirring and kept overnight. Then water (1/25 of the volume of the LiAlH$_4$ solution) was added slowly, followed by 15% NaOH$_{(aq)}$ (1/25 of the volume of the LiAlH$_4$ solution) solution. Finally, water (1/25 of the volume of the LiAlH$_4$ solution) was added along with a large amount of MgSO$_4$. Solution was filtered and the solid was washed with EtOAc and the filtrate was collected. Solvent was stripped off to give (5-chloro-1H-indol-2-yl)methanol (yellow solid) in 85% yield.

Step 2: Two solutions were prepared under $N_2$. The first consisted of a 19M solution (based on imidazole) of DMF containing 1.2 eq tert-butyldimethylsilyl chloride, and 2.5 eq imidazole. The second was 1 eq (5-chloro-1H-indol-2-yl) methanol dissolved in DMF (2.5M). The second solution ((5-chloro-1H-indol-2-yl)methanol in DMF) was added to the first solution and some smoke/steam was evolved. Formed a red-brown solution and was left stirring at rt overnight. Reaction was quenched with a saturated sodium bicarbonate aqueous solution and extracted with a 4:1 mixture of ethyl acetate and diethyl ether. Organic phase was washed with water and brine and dried over Na$_2$SO$_4$. Solvent was removed to give 2-({[tert-butyl(dimethyl)silyl]oxy}methyl)-5-chloro-1H-indole (orange solid) in 99% yield.

Step 3: 2-({[tert-butyl(dimethyl)silyl]oxy}methyl)-5-chloro-1H-indole (1 eq) was dissolved in ether (0.38M) and the solution was cooled to 0° C. Oxalyl chloride (2M in CH$_2$Cl$_2$) (1.2 eq) was added to the above cold solution with vigorous stirring. Precipitation occurred. The suspension was kept stirred at 0° C. for 30 minutes. Then MeOH (3/5 volume of oxalyl chloride solution) was added to the reaction mixture, followed by NEt$_3$ (6/5 volume of oxalyl chloride solution). The resulting mixture was then diluted with MeOH (6/5 volume of oxalyl chloride solution) before it was poured into water (4× volume of oxalyl chloride solution). Extract with EtOAc. Organic phase washed with brine, dried over Na$_2$SO$_4$, and concentrated to give methyl [2-({[tert-butyl(dimethyl)silyl]oxy}methyl)-5-chloro-1H-indol-3-yl](oxo)acetate (brown solid) in 65% yield.

Step 4: Methyl [2-({[tert-butyl(dimethyl)silyl] oxy}methyl)-5-chloro-1H-indol-3-yl](oxo)acetate (1 eq), Ph$_2$CHBr (2 eq) and Cs$_2$CO$_3$ (1.5 eq) were mixed in dry acetonitrile (0.13M) under $N_2$. The mixture was heated with stirring to reflux for 3 hrs. The reaction mixture was cooled to rt and filtered and solvent was removed. Resulting residue was purified using a column with 1:4Hexane/CH$_2$Cl$_2$ as eluent to give methyl [1-benzhydryl-2-({[tert-butyl (dimethyl)silyl]oxy }methyl)-5-chloro-1H-indol-3-yl](oxo) acetate (yellow-brown solid) in 60% yield.

Step 5: Methyl [1-benzhydryl-2-({[tert-butyl(dimethyl) silyl]oxy }methyl)-5-chloro-1H-indol-3-yl](oxo)acetate (1 eq) was dissolved in THF (0.46M), then BH$_3$.Me$_2$S (2M in THF) (2 eq) was added to it. The resulting mixture was refluxed with stirring overnight under $N_2$. The reaction mixture was cooled to rt, then quenched slowly with 1N NaOH$_{(aq)}$. Followed by regular work-up (eg. EtOAc extraction, brine wash, etc.). Removed the solvent and purified using a column with CH$_2$Cl$_2$ as eluent to give 2-[1-benzhydryl-2-({[tert-butyl(dimethyl)silyl]oxy} methyl)-5-chloro-1H-indol-3-yl]ethanol (yellow solid) in 72% yield.

Step 6: A solution was made with 1 eq 2-[1-benzhydryl-2-({[tert -butyl(dimethyl)silyl]oxy}methyl)-5-chloro-1H-indol-3-yl]ethanol and CH$_2$Cl$_2$ (0.12M). Then 0.76 eq of 1,3-bis(diphenylphosphino)propane was added and the solution was cooled to 0° C. under $N_2$. Then 1.3 eq of CBr$_4$ was added to give a light yellow solution. The reaction was allowed to return to room temperature. After three hours and 15 minutes the solvent was removed. Purified using a flash column with silica gel and 1:5 EtOAc/Hexane as eluent to give 1-benzhydryl-3-(2-bromoethyl)-2-({[tert-butyl (dimethyl)silyl]oxy}methyl)-5-chloro-1H-indole (yellow-brown gum) in 90% yield.

Step 7: 1-benzhydryl-3-(2-bromoethyl)-2-({[tert-butyl (dimethyl)silyl]oxy}methyl)-5-chloro-1H-indole (1 eq) was mixed with Methyl 4-mercaptobenzoate (2 eq) and KC$_2$CO$_3$ (1.9 eq) in DMF (0.09M). The resulting mixture was stirred at rt under $N_2$ overnight. Water was then added, followed by regular work-up (eg. EtOAc extration, brine wash, etc) and column purification (1:6 EtOAc/Hexane as eluent) to give methyl 4-({2-[1-benzhydryl-2-({[tert-butyl(dimethyl)silyl] oxy}methyl)-5-chloro-1H-indol-3-yl]ethyl}sulfanyl) benzoate (yellow oil) in 81% yield.

Step 8: Methyl 4-({2-[1-benzhydryl-2-({[tert-butyl (dimethyl)silyl]oxy]methyl)-5-chloro-1H-indol-3-yl] ethyl}sulfanyl)benzoate (1 eq) was dissolved in ACN (0.1M), then molecular sieve (3/4 mass of benzoate) and 4-methylmophorlin N-oxide (NMO, 3 eq) were added under $N_2$. After 10 min, n-Pr$_4$NRuO$_4$ (TPAP, 0.07 eq) was added to it. The resulting mixture was heated to 40° C. with stirring and kept for 2 hours. Cooled to room temperature and filtered. Removed the solvent and residue was purified with a column (1:5 EtOAc/Hexane as eluent) to give methyl 4-({2-[1-benzhydryl-2-({[tert-butyl(dimethyl)silyl]oxy}methyl)-5-chloro-1H-indol-3-yl]ethyl}sulfonyl)benzoate (yellow-white powder) in 49% yield.

Step 9: Methyl 4-({2-[1-benzhydryl-2-({[tert-butyl(dimethyl)silyl]oxy}methyl)-5-chloro-1H-indol-3-yl]ethyl}sulfonyl)benzoate (1 eq) was dissolved in THF (0.3M), followed by nBu₄NF (1M in THF) (1.2 eq). The resulting mixture was stirred at rt for 3 hrs, then quenched with $NH_4Cl_{(aq)}$. Extracted with EtOAc and washed with brine. Purified with prep plate and 1:3 EtOAc/Hexane as eluent to give methyl 4-({2-[1-benzhydryl-5-chloro-2-(hydroxymethyl)-1H-indol-3-yl]ethyl}sulfonyl)benzoate (light brown gum) in 95% yield.

Step 10: Methyl 4-({2-[1-benzhydryl-5-chloro-2-(hydroxymethyl)-1H-indol-3-yl]ethyl}sulfonyl)benzoate (1 eq) was dissolved in THF (0.07M). Then MeOH (2.5× the volume of THF) was added, followed by a 1N NaOH solution (2 eq). The reaction was stirred overnight and the solvent was then removed. The resulting residue was dissolved in water and 1N HCl was added until solution was acidic. The resulting white precipitate was collected by filtration and it was the title compound in 76% yield. m/z (M−1) 557.6

EXAMPLE 158

4-(2-{1-benzhydryl-5-chloro-2-[(2-pyridinylmethoxy)methyl]-1H-indol-3-yl}ethoxy)benzoic acid Step 1: A mixture of ethyl 4-hydrobenzoate (150 mg, 0.9 mmol) and triphenylphosphine polymer bound (1 g, 3 mmol triphenylphosphine/g resin) in 15 mL of $CH_2Cl_2$ was stirred at room temperature for 1 hour. Then the product from step 5 of Example 157 (1.0 eq) was added followed by diethyl azodicarboxylate (174 mg, 1.0 mmol). The reaction mixture was stirred overnight. The resin was then filtered off and the filtrate was washed with water, dried over magnesium sulfate and purified by preparative thin layer chromatography (30% ethyl acetate/hexanes as the developing solvents) to yield a gummy solid.

Step 2—The gummy solid was dissolved in 10 mL of tetrahydrofuran and tetrabutylammonium fluoride (1.0M in tetrahydrofuran, 0.8 mL, 0.8 mmol) was added. After stirring at room temperature for 30 minutes, the reaction mixture was diluted with water, extracted with $CH_2Cl_2$, dried over magnesium sulfate and purified by preparative thin layer chromatography (30% ethyl acetate/hexanes as the developing solvents) to yield 200 mg (41%) of ethyl 4-{2-[1-benzhydryl-5-chloro-2-(hydroxymethyl)-1H-indol-3-yl]ethoxy}benzoate as a white solid.

Step 3: 2-Picolyl chloride hydrochloride (164 mg, 1 mmol) was added to potassium hydride (228 mg of 40% KH, 2 mmol, in mineral oil, washed with hexanes) in 5 mL of dry N,N-dimethylformamide at room temperature. Ethyl 4-{2-[1-benzhydryl-5-chloro-2-(hydroxymethyl)-1H-indol-3-yl]ethoxy}benzoate (140 mg, 0.25 mmol) in 3 mL of N,N-dimethylformamide was added via syringe. After stirring at room temperature for 2 hours, the reaction was quenched with iced water, extracted with $CH_2Cl_2$, dried over magnesium sulfate and purified by preparative thin layer chromatography (20% methanol/$CH_2Cl_2$ as the developing solvents) to yield 16 mg (11%) of the desired product as a pale yellow solid. m/z (M−1) 600.9.

Step 4—The ester from above was hydrolyzed using the procedure from Example 117, step 2 to yield the title compound in 89% yield.

EXAMPLE 159

4-(2-{1-benzhydryl-5-chloro-2-[(4-pyridinylmethoxy)methyl]-1H-indol-3-yl}ethoxy)benzoic acid Step 1—4-Picolyl chloride hydrochloride (164 mg, 1 mmol) was dissolved in a mixture of aqueous sodium bicarbonate and ether in a separatory funnel. The resulting mixture was shaken for a while and the ether layer was separated, dried over magnesium sulfate, filtered, and evaporated to give 4-picolyl chloride. The chloride, 60% sodium hydride in mineral oil (80 mg, 2.0 mmol), and the product from step 2, Example 158 (140 mg, 0.25 mmol) were dissolved in 10 mL of dry N,N-dimethylformamide and the mixture was stirred at room temperature for 1 day. The reaction was then quenched with iced water, extracted with $CH_2Cl_2$, dried over magnesium sulfate and purified by preparative thin layer chromatography (15% methanol/$CH_2Cl_2$ as the developing solvents) to yield 46 mg (31%) of the desired product as a pale yellow solid. m/z (M−1) 601.0.

Step 2—The ester from above was hydrolyzed using the procedure from Example 117, step 2 to yield the title compound in 85% yield.

EXAMPLE 160

4-(2-{1-benzhydryl-2-[(benzyloxy)methyl]-5-chloro-1H-indol-3-yl}ethoxy)benzoic acid Step 1: A solution of ethyl and the product from step 2, Example 158 (140 mg, 0.25 mmol) in tetrahydrofuran (10 mL) was treated with 60% sodium hydride in mineral oil (40 mg, 1.0 mmol) and heated to a gentle reflux for 15 minutes. After cooling to room temperature, benzyl bromide (170 mg, 1.0 mmol) was added in one portion. The resulting mixture was heated to a gentle reflux for 20 minutes. After cooling to room temperature the reaction was quenched by careful addition of iced water and then partitioned between water and $CH_2Cl_2$. The organic layer was dried over magnesium sulfate and purified by preparative thin layer chromatography (20% ethyl acetate/hexanes as the developing solvents) to yield 100 mg (67%) of the desired ester as a gummy solid.

Step 2: The above ester intermediate (100 mg, 0.16 mmol) was dissolved in 8 mL of tetrahydrofuran/methanol/water (2:1:1). Lithium hydroxide monohydrate (100 mg, 2.38 mmol) was added and the reaction was stirred at 40° C. for 1 hour. Most of organic solvents were removed and the remaining aqueous solution was acidified by acetic acid. The precipitate was collected by filtration, washed well with water, and dried in vacuuo to yield 75 mg of the title acid (80%) as an off-white solid. m/z (M−1) 600.0.

EXAMPLE 161

4-[2-(1-benzhydryl-5-chloro-2-{[(4-fluorobenzyl)oxy]methyl}-1H-indol-3-yl)ethoxy]benzoic acid Step 1: The ester intermediate was prepared from ethyl 4-{2-[1-benzhydryl-5-chloro-2-(hydroxymethyl)-1H-indol-3-yl]ethoxy}benzoate and 4-fluorobenzyl bromide according to the procedure in Step 1 Example 160 in 92% yield.

Step 2: The ester intermediate was hydrolyzed according to

Step 2 Example 160 to give the title acid as a white solid in 91% yield. m/z (M−1) 617.9

EXAMPLE 162

4-[2-(1-benzhydryl-5-chloro-2{[(2,4-difluorobenzyl)oxy]methyl}-1H-indol-3-yl)ethoxy]benzoic acid Step 1: The ester intermediate was prepared from methyl 4-{2-[1-benzhydryl-5-chloro-2-(hydroxymethyl)-1H-indol- 3-yl]ethoxy}benzoate and 2,4-difluorobenzyl bromide according to the procedure in Step 1 Example 160 in 63% yield.

Step 2: The ester intermediate was hydrolyzed according to

Step 2 Example 160 to give the title acid as a white solid in 93% yield. m/z (M−1)635.8.

EXAMPLE 163

4-[2-(1-benzhydryl-5-chloro-2{[(4-cynobenzyl)oxy]methyl}-1H-indol-3-yl)ethoxy]benzoic acid Step 1: The ester intermediate was prepared from methyl 4-{2-[1-benzhydryl-5-chloro-2-(hydroxymethyl)-1H-indol-3-yl]ethoxy}benzoate and 4-cyanobenzyl bromide according to the procedure in Step 1 Example 160 in 66% yield.

Step 2: The ester intermediate was hydrolyzed according to

Step 2 Example 160 to give the title acid as a white solid in 82% yield. m/z (M−1)625.0.

EXAMPLE 164

4-{2-[1-benzhydryl-5-chloro-2-({[(E)-3-phenyl-2-propenyl]oxy}methyl)-1H -indol-3-yl)ethoxy] benzoic acid Step 1: The ester intermediate was prepared from methyl 4-{2-[1-benzhydryl-5-chloro-2-(hydroxymethyl)-1H-indol-3-yl]ethoxy}benzoate and cinnamyl bromide according to the procedure in Step 1 Example 160 in 40% yield.

Step 2: The ester intermediate was hydrolyzed according to

Step 2 Example 160 to give the title acid as an off-white solid in 71% yield. m/z (M−1)626.0.

EXAMPLE 165

3-{4-[2-(1-benzhydryl-5-chloro-2-{[(4-fluorobenzyl)oxy]methyl}-1H-indol-3-yl)ethoxy]phenyl}propanoic acid Step 1—The product of step 1, example 167 (110 mg, 0.2 mmol) in tetrahydrofuran (15 mL) was treated with 60% sodium hydride in mineral oil (40 mg, 1.0 mmol) and heated to a gentle reflux for 15 minutes. After cooling to room temperature, 4-fluorobenzyl bromide (190 mg, 1.0 mmol) was added in one portion. The resulting mixture was heated to a gentle reflux for 30 minutes. The reaction was quenched by careful addition of water followed by acetic acid. The reaction mixture was then partitioned between water and $CH_2Cl_2$, dried over magnesium sulfate and purified by preparative thin layer chromatography to yield the desired compound.

Step 2—The ester from above was hydrolyzed according to step 2 Example 160 to yield 75 mg (58%) of the title acid as a white solid. m/z (M−1)645.8.

EXAMPLE 166

3-{4-[2-(1-benzhydryl-5-chloro-2-{[(2,6-difluorobenzyl)oxy]methyl}-1H-indol-3-yl)ethoxy] phenyl}propanoic acid Step 1—The ester of the title acid was prepared from the product of step 1, example 167 and 2,6-difluorobenzyl bromide according to the procedure in Example 160, step 1.

Step 2—The ester from above was hydrolyzed according to step 2 Example 160 to yield the title acid as a white solid in 75% yield. m/z (M−1) 645.8.

EXAMPLE 167

3-(4-{2-[1-benzhydryl-5-chloro-2-(hydroxymethyl)-1H-indol-3-yl]ethoxy}phenyl)propanoic acid Step 1—Methyl 3-(4-hydroxyphenyl)propionate (1.1 eq) was added to polymer-supported triphenylphosphine in $CH_2Cl_2$(0.2M) and stirred for 20' the product of Example 157 step 2 (1.0 eq) and diethyl azodicarboxylate (1.1 eq) were added. The resulting mixture was stirred at room temperature overnight. The solid was removed by filtration. The filtrate was columned by using $CH_2Cl_2$ as eluent to yield 68% of the desired product. m/z(M+H)668.0

Step 2: The product from above (1 eq) was dissolved in THF(0.1M), followed by $nBu_4NF$ (1M in THF) (2 eq). The resulting mixture was stirred at room temperature for 3 hrs, then strip-off solvent. The residue was columned with $EtOAc/CH_2Cl_2$ (1:4) as eluent to give the ester intermediate as white solid.

Step 3: The resulting ester intermediate was (1.0 eq) was dissolved in THF:MeOH (1:1) (0.1M), then added 1N NaOH. The mixture was kept stirred overnight at room temperature. The solvent was stripped off and the residue was dissolved in water to form a basic solution, which was neutralized with diluted HCl solution to precipitate the product. The solid was collected by filtration, washed with water, rinsed with hexane, then dried to give the desired product in 94% yield. m/z(M−H)537.9

EXAMPLE 168

3-[4-({2-[1-benzhydryl-5-chloro-2-(hydroxymethyl)-1H-indol-3-yl]ethyl}sulfonyl)phenyl]propanoic acid Step 1—The product from Example 157, step 6(1 eq) was mixed with Methyl-3-(4-mercaptolphenyl)propionate (2 eq) and $K_2CO_3$ in DMF(0.1M). The resulting mixture was stirred at room temperature under $N_2$ for 2 hrs, then was added water, followed by EtOAc extraction, brine wash, and column purification ($CH_2Cl_2$ as eluent) to give 74% of the desired product as brownish gum. m/z(M+$NH_4$)701.2

Step 2—The product of step 1 (1 eq) was dissolved in acetonitrile(0.1M), then molecular sieve (powder, 4 A,) and 4-methylmophorlin N-oxide(NMO)(4 eq) were added under $N_2$. After 5 min, n-$Pr_4NRuO_4$(TPAP)(0.05 eq) was added to it. The resulting mixture was heated to 40° C. with stirring and kept for 3 hrs. Strip-off the solvent, residue was columned with $CH_2Cl_2$ to 1% $EtOAc/CH_2Cl_2$ as eluent to give 87% of the desired product as yellowish oil. m/z(M+$NH_4$) 733.2

Step 3: the compound above was deprotected according to the procedure in Example 167 Step 2.

Step 4: The ester intermediate was hydrolyzed according to step 3 of Example 167 to yield the title compound. m/z(M−H)585.7

EXAMPLE 169

3-(4-{[2-(1-Benzhydryl-5-chloro-2-methyl-1H-indol-3-yl)ethyl]sulfonyl}phenyl)propanoic acid Step 1—5-Chloro-2-methyl-1H-indol (1.0 eq) was dissolved in ether (1.0M) and the solution was cooled to 0° C. Oxalyl chloride (1.2 eq) in ether (1.0M) was added to the above cold solution with vigorous stirring. Precipitation occurred. The suspension was kept stirred at 0° C. for 30'. Then MeOH was added to the reaction mixture, followed by $NEt_3$. The resulting mixture was then diluted with MeOH before it was poured into water. Extract with EtOAc. Organic phase was washed with brine, dried over $Na_2SO_4$, then concentrated. Collect the precipitate to obtain 90.6% of the desired product. m/z(M−H)249.9

Step 2—Methyl (5-chloro-2-methyl-1H-indol-3-yl)(oxo)acetate (1.0 eq), $Ph_2CHBr$ (2.0 eq) and $Cs_2CO_3$(1.2 eq) were mixed in dry acetonitrile (0.1M). The mixture was heated with stirring to reflux for 2 hours (TLC). The reaction mixture was cooled to room temperature and was added water and extracted with EtOAc. Organic phase was concentrated and the residue was passed through a column with $CH_2Cl_2$ as eluent, then concentrated. The residue was triturated with $Et_2O$ and hexane to give 57.7% of the desired product. m/z(M+H) 418.1

Step 3—Methyl (1-Benzhydryl-5-chloro-2-methyl-1H-indol-3-yl)(oxo)acetate (1.0 eq) was dissolved in THF (0.2M), then $BH_3Me_2S$ (2.0 eq) was added to it. The resulting mixture was refluxed with stirring overnight under $N_2$. The reaction mixture was cooled to room temperature, then quenched slowly with NaOH. Followed by EtOAc extraction, brine wash, drying over $Na_2SO_4$. Striping-off the solvent to give 95% of the desired product. m/z(M+H) 376.1

Step 4—2-(1-Benzhydryl-5-chloro-2-methyl-1H-indol-3-yl)ethanol (1.0 eq) was dissolved in dry $CH_2Cl_2$(0.2M). Then 1,3-bis(diphenylphosphino)propane (0.75 eq) was added and the solution was cooled to 0° C. under $N_2$. Then $CBr_4$ (1.25 eq) was added to give a light yellow solution. The reaction was allowed to return to room temperature and stirred for 3 hours. The solvent was then stripped off. The residue was purified with a flash column chromatography with $CH_2Cl_2$ as eluent to give quantitatively the desired product, which was carried on to next step.

Step 5—1-Bromo-2-(1-Benzhydryl-5-chloro-2-methyl-1H-indol-3-yl)ethane from above was mixed with Methyl-3-(4-mercaptolphenyl) propionate (1.5 eq) and $K_2CO_3$ (1.5 eq) in DMF(0.6M). The resulting mixture was stirred at room temperature under $N_2$ for 2 hours, then was added water, followed by EtOAc extraction and column purification ($CH_2Cl_2$ as eluent) to yield 82% of the desired product. m/z(M+H)554.4

Step 6—Methyl 3-(4-{[2-(1-benzhydryl-5-chloro-2-methyl-1H-indol-3-yl)ethyl]sulfanyl}phenyl)propanoate (1.0 eq) was dissolved in acetonitrile (0.01M), then molecular sieve (powder, 4 A,) and 4-methylmophorlin N-oxide (NMO, 3.0 eq) were added under $N_2$. After 5 min, n-$Pr_4NRuO_4$ (TPAP, 0.05 eq) was added to it. The resulting mixture was heated to 40° C. with stirring and kept for 3 hours. Strip-off the solvent, residue was columned with $CH_2Cl_2$ to 1%EtOAc/$CH_2Cl_2$ as eluent to yield 25% of the desired product. m/z(M+H)586.1

Step 7—The ester fromabove was hydrolyzed according to step 2, Example 117 to yield 95% of the title product as pinkish white solid, m/z(M−H) 569.8

EXAMPLE 170

3-(4 {[2-(1-benzhydryl-5-chloro-2-methyl-1H-indol-3-yl)ethyl]sulfanyl}phenyl)propanoic acid Step 1—The product from step 5, Example 169 was hydrolyzed according to step 2 of Example 117 to yield the title acid. m/z(M−H) 537.9

EXAMPLE 171

3-{4-[2-(1-Benzhydryl-5-chloro-2-methyl-1H-indol-3-yl)ethoxy]phenyl}propanoic acid (10)

Step 1: Methyl 3-(4-hydroxyphenyl)propionate (1.1 eq) was added to polymer-supported triphenylphosphine in $CH_2Cl_2$ (0.2M) and stirred for 20' before the product of step 3, Example 169(1.0 eq) and diethyl azodicarboxylate (1.1 eq) were added. The resulting mixture was stirred at room temperature overnight. The solid was removed by filtration. The filtrate was columned by using $CH_2Cl_2$ as eluent to yield 68% of the desired product.

Step 2: The resulting ester intermediate was hydrolyzed according to the procedure in Example 117, step 2. m/z(M+H)523.5

| Example No. | % Inhibition | Conc (uM) |
| --- | --- | --- |
| Example 139 | 50 | 1.6 |
| Example 140 | 50 | 2.5 |
| Example 141 | 50 | 1.4 |
| Example 142 | 50 | 1.4 |
| Example 143 | 50 | 3 |
| Example 144 | 50 | 12 |
| Example 145 | 50 | 2.6 |
| Example 146 | 50 | 1.6 |
| Example 147 | 50 | 2.4 |
| Example 148 | 50 | 2.8 |
| Example 149 | 50 | 2.5 |
| Example 150 | 50 | 2.5 |
| Example 151 | 50 | 3.3 |
| Example 152 | 50 | 3.3 |
| Example 153 | 50 | 3 |
| Example 154 | 50 | 5.5 |
| Example 155 | 50 | 2.2 |
| Example 156 | 50 | 1 |
| Example 157 | 50 | 3.8 |
| Example 158 | 50 | 1.7 |
| Example 159 | 50 | 4.2 |
| Example 160 | 50 | 2 |
| Example 161 | 50 | 1.8 |
| Example 162 | 50 | 1.5 |
| Example 163 | 50 | 1.25 |
| Example 164 | 50 | 3.5 |
| Example 165 | 50 | 0.8 |
| Example 166 | 58 | 0.31 |
| Example 167 | 50 | 1.3 |
| Example 168 | 50 | 2.4 |
| Example 169 | 50 | 0.45 |
| Example 170 | 50 | 0.5 |
| Example 171 | 50 | 0.4 |

The compounds of this invention inhibit Cytosolic Phospholipase A2 (cPLA2) activity which is required for supplying arachidonic acid substrate to cyclooxygenase −1 or 2 and 5-lipoxygenase, which in turn initiates the production of prostaglandins and leukotrienes, respectively. In addition, cPLA2 activity is essential for producing the lysophospholipid precursor to Platelet Activating Factor (PAF). Thus, these compounds are useful in the treatment and prevention of disease states in which leukotrienes, prostaglandins or PAF are involved. Moreover, in diseases where more than one of these agents plays a role, a cPLA2 inhibitor is efficacious than leukotriene, prostaglandin or PAF receptor antagonists and also more effective than cyclooxygenase or 5-lipoxygenase inhibitors.

Therefore, the compounds, pharmaceutical compositions and regimens of the present invention are useful in treating and preventing the disorders treated by cyclooxygenase-2, cycloxygenase-1, and 5-lipoxygenase inhibitors and also are antagonists of the receptors for PAF, leukotrienes or prostaglandins. Diseases treatable by compounds, formulations and regimens of this invention include, but are not limited to, pulmonary disorders including diseases such as asthma, chronic bronchitis, and related obstructive airway diseases; allergies and allergic reactions such as allergic rhinitis, contact dermatitis, allergic conjunctivitis, and the like;

inflammation such as arthritis or inflammatory bowel diseases; skin disorders such as psoriasis, atopic eczema, acne, ultraviolet (UV) damage, burns and dermatittis; cardiovascular disorders such as atherosclerosis, angina, myocardial ischaemia, hypertension, platelet aggregation, and the like; and renal insufficiency induced by immunological or chemical. The drugs may also be cytoprotective, preventing damage to the gastrointestinal mucosa by noxious agents. The compounds are also useful in the treatment of adult respiratory distress syndrome, endotoxin shock and ischeamia induced injury including myocardial or brain injury.

These compounds are especially useful in the treatment of arthritic disorders, including but not limited to rheumatoid arthritis, spondyloarthropathies, gouty arthritis, osteoarthritis, systemic lupus erythematosus and juvenile arthritis. The compounds of this invention are further useful in the treatment of post-operative inflammation, including that following ophthalmic surgery such as cataract surgery or refractive surgery The compounds of this invention can be used as an antipyretic agent and in combination with other antipyretic agents known in the art.

The compounds of this invention may be utilized in methods of treating pain, particularly the pain associated with inflammation. Specific methods include, but are not limited to, those for treating centrally mediated pain, peripherally mediated pain, musculo-skeletal pain, lumbosacral pain, structural or soft tissue injury related pain, progressive disease related pain, such as oncology and degenerative disorders, neuropathic pain, which can include both acute pain, such as acute injury or trauma, pre- and post-surgical, migraine pain, dental pain, etc., chronic pains, such as neuropathic pain conditions of diabetic peripheral neuropathy, post-herpetic neuralgia and fibromyalgia, and inflammatory conditions such as osteoarthritis or rheumatoid arthritis, sequela to acute injury or trauma and cancer-related pain.

Compositions and compounds of this invention are also useful in the treatment of menstrual cramps, preterm labor, tendonitis, bursitis, allergic neuritis, cytomegalovirus infection, apoptosis, including HIV-induced apoptosis, lumbago, liver disease including hepatitis.

The methods and compositions herein are also useful in treating gastrointestinal conditions such as inflammatory bowel disease, Crohn's disease, gastritis, irritable bowel syndrome and ulcerative colitis and for the prevention of treatment of cancer such as colorectal cancer. The compounds and compositions of the present invention are also useful for the prevention or treatment of benign and malignant tumors/neoplasia including cancers such as colorectal cancer, brain cancer, bone cancer, epithelial cell-derived neoplasia (epithelial carcinoma) such as basal cell carcinoma, adenocarcinoma, gastrointestinal cancer, including lip cancer, mouth cancer, esophogeal cancer, small bowel cancer and stomach cancer, colon cancer, liver cancer, bladder cancer, pancreatic cancer, ovarian cancer, cervical cancer, lung cancer, breast cancer, and skin cancers, such as squamous cell and basal cell cancers, prostate cancer, renal cell carcinoma, and other known cancers that effect epithelial cells throughout the body. Neoplasias for which compositions of the invention are particularly useful are gastrointestinal cancer, Barrett's esophagus, liver cancer, bladder cancer, pancreas cancer, ovarian cancer, prostatic cancer, cervical cancer, lung cancer, breast cancer, and skin cancer, such as squamous cell and basal cell cancers. The compounds and methods of this invention can also be used to treat the fibrosis occuring with radiation therapy. Such compositions can be used to treat subjects having adenomatous polyps, including those with familial adenomatous polyposis (FAP). Additionally, such compositions can be used to prevent polyps from forming in patients at risk of FAP. Compounds of this invention will be useful in the treatment of cancers based on anti-angiogenic effects.

Further uses of this invention include treating inflammation in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury including brain edema, myocardial ischemia, and the like. Also included are treatment of ophthalmic diseases, such as retinitis, conjunctivitis, retinopathies, uveitis, ocular photophobia, and of acute injury to the eye tissue. Treatments herein of pulmonary inflammation, such as that associated with viral infections and cystic fibrosis, and in bone resorption such as that accompanying osteoporosis. These compounds and compositions are useful for the treatment of certain central nervous system disorders, such as cortical dementias including Alzheimer's disease, neurodegeneration, and central nervous system damage resulting from stroke, ischemia and trauma. The compounds of this invention may also be useful in the treatment of Parkinson's disease.

It will be understood that methods of treating or preventing the maladies listed herein comprise administering to a mammal subject to or experiencing the malady, which may also be referred to as a mammal in need thereof, a pharmaceutically effective amount of a compound of this invention, or a pharmaceutically acceptable salt thereof.

Methods of treating pain comprise administering to a mammal subject to such pain a pharmaceutically effective amount of a compound of this invention alone or in combination with one or more additional pharmaceutically effective agents for the treatment of pain or inflammation or the related underlying medical condition. Examples of drug agents which may be combined with the present compounds are analgesics, anti-angiogenic agents, anti-neoplastic agents, These compounds may also be combined with antiepileptic compounds that have pain alleviating properties, such as gabapentin and pregabalin.

One such combination method of this invention comprises administering to a mammal in need thereof a pharmaceutically effective amount of a compound of this invention and a pharmaceutically effective amount of a nontoxic N-methyl-D-aspartate (NMDA) receptor antagonist and/or an agent that blocks at least one major intracellular consequence of NMDA receptor activation. Examples of NMDA receptor antagonists useful in these methods include dextromethorphan, dextrorphan, amantadine and memantine, or the pharmaceutically acceptable salts thereof.

Another method herein of treating inflammation and inflammatory disorders comprises the co-administration to a mammal in need thereof of an inhibitor of induced nitric oxide synthase with a compound of this invention. Administration of this combination is useful for prophylactic or therapeutic administration in a mammal experiencing or subject to an abnormally low level of nitric oxide synbthase (NOS) activity, particularly those subject to hypertension or an elevated risk of pulmonary hypertension, ischemic stroke, myocardial infarction, heart failure, progressive renal disease, thrombosis, reperfusion injury, or a nervous system degenerative disorder, such as Alzheimer's disease, or those chronically exposed to hypoxic conditions.

The methods of this invention also include those for treating or preventing a neoplasia disorder in a mammal, including a human, in need of such treatment or prevention. The method comprises treating the mammal with a therapeutically effective amount of a compound of this invention in combination with an MMP inhibitor. These two components may further be optionally combined with one or more agents selected from an antiangiogenesis agent, an antineoplastic agent, an adjunctive agent, an immunotherapeutic agent, an analgesic agent; and/or a radiotherapeutic agent. One such multiple component therapy comprises administering to the mammal in need thereof a compound of this invention, a matrix metalloproteinase inhibitor and an antineoplastic agent.

The methods and combinations of this invention may be used for the treatment or prevention of neoplasia disorders including acral lentiginous melanoma, actinic keratoses, adenocarcinoma, adenoid cycstic carcinoma, adenomas, adenosarcoma, adenosquamous carcinoma, astrocytic tumors, bartholin gland carcinoma, basal cell carcinoma, bronchial gland carcinomas, capillary, carcinoids, carcinoma, carcinosarcoma, cavernous, cholangiocarcinoma, chondosarcoma, choriod plexus papilloma/carcinoma, clear cell carcinoma, cystadenoma, endodermal sinus tumor, endometrial hyperplasia, endometrial stromal sarcoma, endometrioid adenocarcinoma, ependymal, epitheloid, Ewing's sarcoma, fibrolamellar, focal nodular hyperplasia, gastrinoma, germ cell tumors, glioblastoma, glucagonoma, hemangiblastomas, hemangioendothelioma, hemangiomas, hepatic adenoma, hepatic adenomatosis, hepatocellular carcinoma, insulinoma, intaepithelial neoplasia, interepithelial. squamous cell neoplasia, invasive squamous cell carcinoma, large cell carcinoma, leiomyosarcoma, lentigo maligna melanomas, malignant melanoma, malignant mesothelial tumors, medulloblastoma, medulloepithelioma, melanoma, meningeal, mesothelial, metastatic carcinoma, mucoepidermoid carcinoma, neuroblastoma, neuroepithelial adenocarcinoma nodular melanoma, oat cell carcinoma, oligodendroglial, osteosarcoma, pancreatic polypeptide, papillary serous adenocarcinoma, pineal cell, pituitary tumors, plasmacytoma, pseudosarcoma, pulmonary blastoma, renal cell carcinoma, retinoblastoma, rhabdomyosarcoma, sarcoma, serous carcinoma, small cell carcinoma, soft tissue carcinomas, somatostatin-secreting tumor, squamous carcinoma, squamous cell carcinoma, submesothelial, superficial spreading melanoma, undifferentiated carcinoma, uveal melanoma, verrucous carcinoma, vipoma, well differentiated carcinoma, and Wilm's tumor.

Antineoplastic agents useful in the combination therapies herein include anastrozole, calcium carbonate, capecitabine, carboplatin, cisplatin, Cell Pathways CP-461, docetaxel, doxorubicin, etoposide, fluorouracil, fluoxymestrine, gemcitabine, goserelin, irinotecan, ketoconazole, letrozol, leucovorin, levamisole, megestrol, mitoxantrone, paclitaxel, raloxifene, retinoic acid, tamoxifen, thiotepa, topotecan, toremifene, vinorelbine, vinblastine, vincristine, selenium (selenomethionine), ursodeoxycholic acid, sulindac sulfone, exemestane and eflornithine (DFMO), 1-[4-(2-Azepan-1yl-ethoxy)-benzyl]-2-(4-hydroxy-phenyl)-3-methyl-1H-indol-5-ol (TSE-424) and 2-(4-Hydroxy-phenyl)-3-methyl-1-(4-(2-piperidin-1-yl-ethoxy)-benzyl]-1H-indol-5-ol (ERA-923).

This invention also includes methods of utilizing the compounds herein in combination with a proteinaceous interleukin-1 inhibitor, such as an IL-1 receptor antagonist (IL-1ra), for preventing or treating inflammatory diseases in a mammal. Acute and chronic interleukin-1 (IL-1)-mediated inflammatory diseases of interest in these methods include, but is not limited to acute pancreatitis; ALS; Alzheimer's disease; cachexia/anorexia; asthma; atherosclerosis; chronic fatigue syndrome, fever; diabetes (e.g., insulin diabetes); glomerulonephritis; graft versus host rejection; hemohorragic shock; hyperalgesia, inflammatory bowel disease; inflammatory conditions of a joint, including osteoarthritis, psoriatic arthritis and rheumatoid arthritis; ischemic injury, including cerebral ischemia (e.g., brain injury as a result of trauma, epilepsy, hemorrhage or stroke, each of which may lead to neurodegeneration); lung diseases (e.g., ARDS); multiple myeloma; multiple sclerosis; myelogenous (e.g., AML and CML) and other leukemias; myopathies (e.g., muscle protein metabolism, esp. in sepsis); osteoporosis; Parkinson's disease; pain; pre-term labor; psoriasis; reperfusion injury; septic shock; side effects from radiation therapy, temporal mandibular joint disease, tumor metastasis; or an inflammatory condition resulting from strain, sprain, cartilage damage, trauma, orthopedic surgery, infection or other disease processes.

This invention also provides a method of administering one or more of the compounds of this invention to a female in need thereof to substantially prevent or reducing changes in the female's reproductive system associated with onset or continuation of labor. Also provided is a method of substantially preventing or reducing uterine contractility either occurring during pregnancy or associated with menorrhagia. These methods may optionally include coadministration of a compound of this invention with a progestogen, a progestin or a progestational agent.

All patents and literature references cited herein are incorporated as if fully set forth herein.

What is claimed:

1. A compound of the formulae:

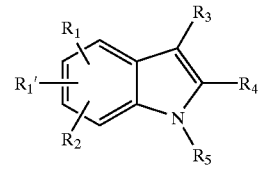

wherein:

R$_1$ and R$_1$, are independently selected from the group consisting of H, halogen, —CF$_3$, —OH, —C$_1$-C$_{10}$ alkyl, —S—C$_1$-C$_{10}$ alkyl, C$_1$-C$_{10}$ alkoxy, —CN, —NO$_2$, —NH$_2$, phenyl, —O-phenyl, —S-phenyl, benzyl, —O-benzyl, —S-benzyl; and a moiety of the formulae:

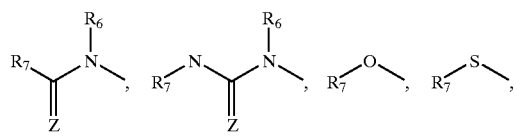

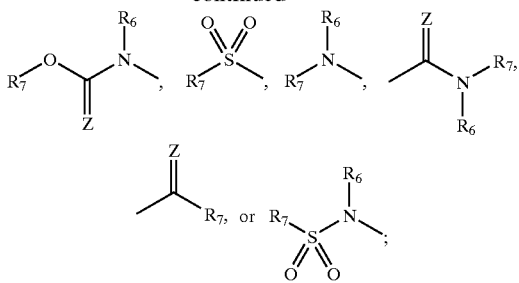

Z is O or S;

R$_6$ is selected from the group consisting of H, —CF$_3$, C$_1$–C$_{10}$ alkyl, C$_1$–C$_{10}$ alkoxy, phenyl, —O-phenyl, —S-phenyl, benzyl, —O-benzyl, and —S-benzyl, the phenyl and benzyl rings of these group members being optionally substituted by from 1 to 3 substituents selected from halogen, C$_1$–C$_{10}$ alkyl, C$_1$–C$_{10}$ alkoxy, —CHO, —NO$_2$, —NH$_2$, —CN, —CF$_3$, and —OH;

R$_7$ is selected from the group consisting of —(CH$_2$)$_n$—COOH, —(CH$_2$)$_n$—N—(C$_1$–C$_6$ alkyl)$_2$, —(CH$_2$)$_n$—NH—(C$_1$–C$_6$ alkyl), —CF$_3$, C$_1$–C$_6$ alkyl, C$_3$–C$_5$ cycloalkyl, C$_1$–C$_6$ alkoxy, —NH—(C$_1$–C$_6$ alkyl), —N—(C$_1$–C$_6$ alkyl)$_2$, (CH$_2$)$_n$phenyl, phenyl, —O-phenyl, benzyl, —O-benzyl, adamantyl, —(CH$_2$)$_n$-phenyl-O-phenyl, —(CH$_2$)$_n$-phenyl-CH$_2$-phenyl, —(CH$_2$)$_n$-O-phenyl-CH$_2$-phenyl, and —(CH$_2$)$_n$-phenyl-(O—CH$_2$-phenyl)$_2$, the rings of these group members being optionally substituted by from 1 to 3 substituents selected from halogen, C$_1$–C$_6$ alkyl, C$_1$–C$_6$ alkoxy, —N$_2$, —NO$_2$, —CF$_3$, CO$_2$H, and —OH;

n is an integer from 0 to 3;

R$_2$ is selected from the group consisting of H, halogen, —CN, —CHO, —CF$_3$, —OH, C$_1$–C$_{10}$ alkyl, C$_1$–C$_{10}$ alkoxy, —CHO, —CN, —NO$_2$, —NH$_2$, —NH—C$_1$–C$_6$ alkyl, —N(C$_1$–C$_6$ alkyl)$_2$, —N—SO$_2$—C$_1$–C$_6$ alkyl, and —SO$_2$—C$_1$–C$_6$ alkyl;

R$_3$ is selected from the group consisting of —COOH, —C(O)—COOH, —(CH$_2$)$_n$—C(O)—COOH, —(CH$_2$)$_n$—COOH, —(CH$_2$)$_n$—CH=CH—COOH,

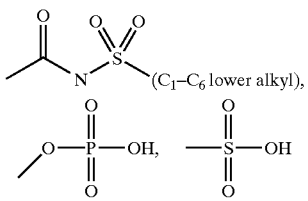

and a moiety of the formulae —L$^1$—M$^1$;

wherein

L$^1$ is a bridging or linking moiety selected from a chemical bond, —(CH$_2$)$_n$—, —S—, —O—, —SO$_2$—, —C(O)—, —CH$_2$)$_n$—C(O)—, —(CH$_2$)$_n$—C(O)—(CH$_2$)$_n$—, —(CH$_2$)$_n$—O—(CH$_2$)$_n$—, —C(Z)—N(R$_6$)—, —C(Z)—N(R$_6$)—(CH$_2$)$_n$—, —C(O)—C(Z)—N(R$_6$)—, —C(O)—C(Z)—N(R$_6$)—(CH$_2$)$_n$—, —C(Z)—NH—SO$_2$—, —C(Z)—NH—SO$_2$—(CH$_2$)$_n$—, —(CH$_2$)$_n$—S—(CH$_2$)$_n$—, —(CH$_2$)$_n$—SO—(CH$_2$)$_n$—, —(CH$_2$)$_n$—SO$_2$—(CH$_2$)$_n$—, or —(CH$_2$)$_n$—CH=CH—(CH$_2$)$_n$—O—;

n is an integer from 0 to 3;

M$^1$ is selected from the group consisting of —COOH, —(CH$_2$)$_n$—COOH, —(CH$_2$)$_n$—C(O)—COOH, tetrazole,

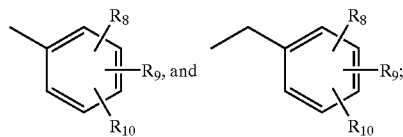

R$_8$ is —COOH, —(CH$_2$)$_n$—COOH, or —(CH$_2$)$_n$—C(O)—COOH;

R$_9$ is H;

R$_{10}$ is H;

n is an integer from 0 to 3;

R$_4$ is selected from the group consisting of H, —CF$_3$, C$_1$–C$_6$ lower alkyl, C$_1$–C$_6$ lower alkoxy, C$_3$–C$_{10}$ cycloalkyl, —C$_1$–C$_6$ alkyl-C$_3$–C$_{10}$ cycloalkyl, —CHO, halogen, and a moiety of the formula —L$^2$—M$^2$:

L$^2$ indicates a linking or bridging group of the formulae —(CH$_2$)$_n$—, —S—, —O—, —C(O)—, —(CH$_2$)$_n$—C(O)—, —(CH$_2$)$_n$—C(O)—(CH$_2$)$_n$—, —(CH$_2$)$_n$—O—(CH$_2$)$_n$—, —(CH$_2$)$_n$—S—(CH$_2$)$_n$—, C(O)C(O)X, or —(CH$_2$)$_n$—N—(CH$_2$)$_n$;

where X is O or N n is an integer from 0 to 3;

M$^2$ is selected from the group consisting of H, C$_1$–C$_6$ lower alkyl, C$_1$–C$_6$ lower alkoxy, C$_3$–C$_{10}$ cycloalkyl, phenyl and benzyl, the cycloalkyl, phenyl and benzyl rings being optionally substituted by from 1 to 3 substituents selected from halogen, C$_1$–C$_{10}$ alkyl, C$_1$–C$_{10}$ alkoxy, —NO$_2$, —NH$_2$, —CN, and —CF$_3$;

R$_5$ is a moiety of the formulae —(CH$_2$)$_n$—A, wherein A is the moiety:

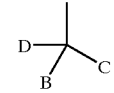

wherein

D is H;

B and C are each phenyl, each optionally substituted by from 1 to 3 substituents selected from the group consisting of H, halogen, —CN, —CHO, —CF$_3$, —OH, —C$_1$–C$_6$ alkyl, C$_1$–C$_6$ alkoxy, —NH$_2$, —N(C$_1$–C$_6$)$_2$, —NH(C$_1$–C$_6$), —N—C(O)—(C$_1$–C$_6$), and —NO$_2$;

or a pharmaceutically acceptable salt thereof.

2. A compound of claim 1, or a pharmaceutically acceptable salt thereof, wherein R$_4$ is hydrogen and R$_1$, R$_2$, R$_3$, R$_5$, R$_6$, R$_7$, R$_8$, R$_9$, R$_{10}$, Z, L$^1$, M$^1$, L$^2$, M$^2$, n, Y, Z, B, C, and D are as described in claim 1.

3. A compound of claim 1, or a pharmaceutically acceptable salt thereof, having the formulae:

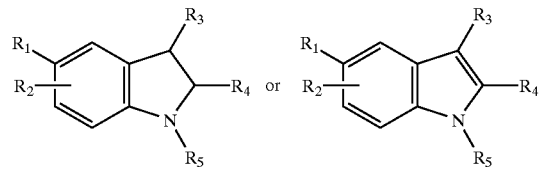

wherein R$_2$, R$_3$, R$_4$, R$_5$, R$_6$, R$_7$, R$_8$, R$_9$, R$_{10}$, Z, L$^1$, M$^1$, L$^2$, M$^2$, n, Y, Z, B, C, and D are as defined in claim 1.

4. A compound of the formulae:

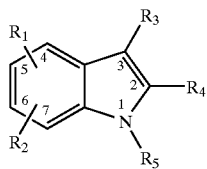

wherein:

$R_1$ is selected from the group consisting of H, halogen, —$CF_3$, —OH, —$C_1$-$C_{10}$ alkyl, —S—$C_1$-$C_{10}$ alkyl, $C_1$-$C_{10}$ alkoxy, —CN, —$NO_2$, —$NH_2$, 13 HN($C_1$-$C_6$), —N($C_1$-$C_6$)$_2$, phenyl, —O-phenyl, —S-phenyl, benzyl, —O-benzyl, and —S-benzyl, the phenyl and benzyl rings of these group members being optionally substituted by from 1 to 3 substituents selected from halogen, $C_1$-$C_6$ alkyl, $C_1$-$C_6$ alkoxy, —$NO_2$, —$NH_2$, —CN, —$CF_3$, and —OH;

$R_2$ is selected from the group consisting of H, halogen, —$CF_3$, —OH, —$C_1$-$C_{10}$ alkyl, $C_1$-$C_{10}$ alkoxy, —CHO, —CN, —$NO_2$, —$NH_2$, —NH—$C_1$-$C_6$ alkyl, —N($C_1$-$C_6$ alkyl)$_2$, —N—$SO_2$—$C_1$-$C_6$ alkyl, and —$SO_2$—$C_1$-$C_6$ alkyl;

$R_3$ is a moiety selected from the groups of:

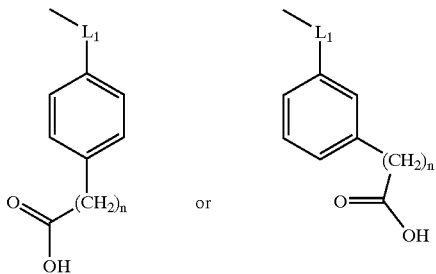

wherein $L^1$ is a bridging or linking moiety selected from a chemical bond, —$(CH_2)_{n'}$—, —$(CH_2)_{n'}$—C(O)—$(CH_2)_{n'}$—, —$(CH_2)_{n'}$—O—$(CH_2)_{n'}$—, —$(CH_2)_{n'}$—S—$(CH_2)_{n'}$—, —$(CH_2)_{n'}$—SO—$(CH_2)_{n'}$—, —$(CH_2)_{n'}$—$SO_2$—$(CH_2)_{n'}$—, and —$(CH_2)_{n'}$—CH=CH—$(CH_2)_{n'}$—O—;

where n' is an integer from 0 to 3;

n in each instance is independently selected as an integer from 0 to 3;

$R_4$ is selected from H or —$C_1$-$C_6$ alkyl;

$R_5$ is a moiety of the formulae —$(CH_2)_n$—A, wherein A is the moiety:

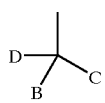

wherein

D is H;

B and C are phenyl, each optionally substituted by from 1 to 3 substituents selected from H, halogen, —$CF_3$, —OH, —$C_1$-$C_6$ alkyl, $C_1$-$C_6$ alkoxy, and —$NO_2$;

or a pharmaceutically acceptable salt thereof.

5. A compound of the formulae:

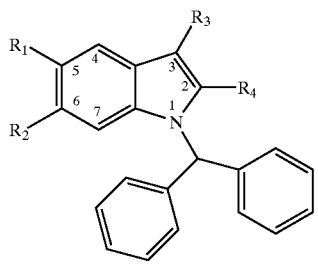

wherein:

$R_1$ is selected from the group consisting of H, halogen, —$CF_3$, —OH, —CN, —$NO_2$, —$NH_2$, —HN($C_1$-$C_6$), —N($C_1$-$C_6$)$_2$, phenyl, —N—$SO_2$—$C_1$-$C_6$ alkyl, and —$SO_2$—$C_1$-$C_6$ alkyl;

$R_2$ is selected from the group consisting of H, halogen, —$CF_3$, —OH, —CN, —$NO_2$, —$NH_2$, —NH—$C_1$-$C_6$ alkyl, —N($C_1$-$C_6$ alkyl)$_2$, —N—$SO_2$—$C_1$-$C_6$ alkyl, and —$SO_2$—$C_1$-$C_6$ alkyl;

$R_3$ is a moiety selected from the groups of:

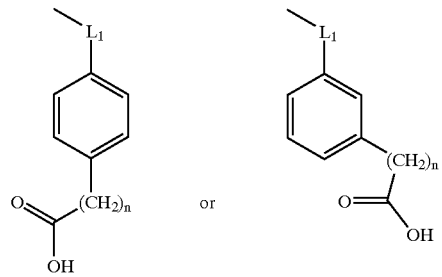

wherein $L^1$ is a bridging or linking moiety selected from a chemical bond, —$(CH_2)_{n'}$—, —$(CH_2)_{n'}$—C(O)—$(CH_2)_{n'}$, —$(CH_2)_{n'}$—O—$(CH_2)_{n'}$—, —$(CH_2)_{n'-S-}(CH_2)_{n'}$—, —$(CH_2)_{n'}$—SO—$(CH_2)_{n'}$—, —$(CH_2)_{n'}$—$SO_2$—$(CH_2)_{n'}$—, and —$(CH_2)_{n'}$—CH=CH—$(CH_2)_{n'}$—O—;

n' in each instance is independently selected as an integer from 0 to 3;

$R_4$ is selected from the group consisting of H, —$C_1$-$C_6$ alkyl, $(CH_2)_n$C(O)$NH_2$, —$(CH_2)_n$—O—($C_1$-$C_6$ alkyl), —$(CH_2)_n$—O—$CH_2$-phenyl, —$(CH_2)_n$—N—($C_1$-$C_6$ alkyl), and —$(CH_2)_n$—N—$CH_2$-phenyl, the phenyl rings of which are optionally substituted by 1 or 2 groups selected from H, halogen, —$CF_3$ and —$C_1$-$C_6$ alkyl;

n is an integer from 0–3;

or a pharmaceutically acceptable salt thereof.

6. A pharmaceutical composition comprising a compound of claim 1, or a pharmaceutically acceptable salt thereof, and a pharmaceutically acceptable carrier or excipient.

7. A method for treating inflammation in a mammal, the method comprising administering to a mammal in need thereof a therapeutically effective amount of a compound of claim 1, or a pharmaceutically acceptable salt thereof.

8. The method of claim 7 wherein the inflammation is caused by arthritis.

9. The method of claim 7 wherein the inflammation is caused by inflammatory bowel diseases.

10. The method of claim 7 wherein the inflammation is caused by asthma.

11. A compound of claim 1 selected from the group consisting of:

a) 4-[(1-benzhydryl-5-{[(butylamino)carbonyl]amino}-1H-indol-3-yl)methyl]-3-methoxybenzoic acid;
b) 4-({1-benzhydryl-5-[(methylsulfonyl)amino]-1H-indol-3-yl}methyl)-3-methoxybenzoic acid;
c) 4-({1-benzhydryl-5-[(cyclopentylcarbonyl)amino]-1H-indol-3-yl}methyl)-3-methoxybenzoic acid;
d) 4-[(1-benzhydryl-5-nitro-1H-indol-3-yl)methyl]-3-methoxybenzoic acid;
e) 4-[(1-benzhydryl-5-fluoro-1H-indol-3-yl)methyl]-3-methoxybenzoic acid;
f) 4-[(1-benzhydryl-5-methyl-1H-indol-3-yl)methyl]-3-methoxybenzoic acid;
g) 4-[(1-benzhydryl-5-cyano-1H-indol-3-yl)methyl]-3-methoxybenzoic acid; and
h) 4-{[1-benzhydryl-5-(methylsulfonyl)-1H-indol-3-yl]methyl}-3-methoxybenzoic acid;

or a pharmaceutically acceptable salt thereof.

12. A compound of claim 1 selected from the group consisting of:

a) 4-[(1-benzhydryl-5-nitro-1H-indol-3-yl)methyl]benzoic acid;
b) 4-[(1-benzhydryl-5-bromo-1H-indol-3-yl)methyl]benzoic acid; and
c) 4-[(1-benzhydryl-5-{[(cyclopentyloxy)carbonyl]amino}-1H-indol-3-yl)methyl]benzoic acid;

or a pharmaceutically acceptable salt form thereof.

13. A compound of claim 1 selected from the group consisting of:

a) N-{4-[(1-benzhydryl-5-bromo-1H-indol-3-yl)methyl]benzoyl}(trifluoro)methanesulfonamide;
b) 3-[({1-benzhydryl-5-[(cyclopentylcarbonyl)amino]-1H-indol-3-yl}methyl)amino]benzoic acid;
c) 3-{1-benzhydryl-5-[(cyclopentylcarbonyl)amino]-1H-indol-3-yl}propanoic acid; and
d) (E)-3-{1-benzhydryl-5-[(cyclopentylcarbonyl)amino]-1H-indol-3-yl}-2-propenoic acid;

or a pharmaceutically acceptable salt form thereof.

14. A compound of claim 1 selected from the group consisting of:

a) 4-{[1-benzhydryl-5-({[4-(trifluoromethyl)phenyl]sulfonyl}amino)-1H-indol-3-yl]methyl}-3-methoxybenzoic acid;
b) 4-[(1-benzhydryl-5-{[(4-chloro-3-nitrophenyl)sulfonyl]amino}-1H-indol-3-yl)methyl]-3-methoxybenzoic acid;
c) 4-[(1-benzhydryl-5-{[(dimethylamino)sulfonyl]amino}-1H-indol-3-yl)methyl]-3-methoxybenzoic acid;
d) 4-{[1-benzhydryl-5-({[4-(trifluoromethoxy)phenyl]sulfonyl}amino)-1H-indol-3-yl]methyl}-3-methoxybenzoic acid;
e) 4-[(1-benzhydryl-5-{[(2-methylphenyl)sulfonyl]amino}-1H-indol-3-yl)methyl]-3-methoxybenzoic acid;
f) 3-[({1-benzhydryl-5-[(cyclopentylcarbonyl)amino]-1H-indol-3-yl}carbonyl)amino]benzoic acid; and
g) 3-[({1-benzhydryl-5-[(cyclopentylcarbonyl)amino]-1H-indol-3-yl}carbonyl)amino]propanoic acid;

or a pharmaceutically acceptable salt form thereof.

15. A compound of claim 1:

2-{4-[(1-benzhydryl-6-chloro-1H-indol-3-yl)methyl]-2,6-dimethylphenoxy}acetic acid;

or a pharmaceutically acceptable salt thereof.

16. A compound of claim 1 selected from the group consisting of:

a) 4-{[2-(1-benzhydryl-5-fluoro-2-methyl-1H-indol-3-yl)ethyl]sulfonyl}benzoic acid; and
b) 4-{[2-(1-benzhydryl-6-chloro-2-methyl-1H-indol-3-yl)ethyl]sulfonyl}benzoic acid;

or a pharmaceutically acceptable salt form thereof.

17. A compound of claim 1 selected from the group consisting of:

a) 4-{[2-(1-benzhydryl-4,5-dichloro-2-methyl-1H-indol-3-yl)ethyl]sulfonyl}benzoic acid;
b) 4-{[2-(1-benzhydryl-5,6-dichloro-2-methyl-1H-indol-3-yl)ethyl]sulfonyl}benzoic acid;
c) 4-{[2-(1-benzhydryl-2-methyl-1H-indol-3-yl)ethyl]sulfonyl}benzoic acid;
d) 4-{[2-(1-benzhydryl-5-methoxy-2-methyl-1H-indol-3-yl)ethyl]sulfonyl}benzoic acid;
e) 4-[2-(1-benzhydryl-5-bromo-2-methyl-1H-indol-3-yl)ethoxy]benzoic acid;
f) 4-{[2-(1-benzhydryl-5-chloro-2-methyl-1H-indol-3-yl)ethyl]sulfanyl}benzoic acid;
g) 4-{[2-(1-benzhydryl-5-chloro-2-methyl-1H-indol-3-yl)ethyl]sulfonyl}benzoic acid;
i) 4-{[2-(1-benzhydryl-5-chloro-2-methyl-1H-indol-3-yl)ethyl]sulfinyl}benzoic acid; and
j) 4-[2-(1-benzhydryl-5-chloro-2-methyl-1H-indol-3-yl)ethoxy]benzoic acid;

or a pharmaceutically acceptable salt form thereof.

18. A compound of claim 1 selected from the group consisting of:

a) 4-[2-(1-benzhydryl-5-chloro-2-formyl-1H-indol-3-yl)ethoxy]benzoic acid;
b) 4-{2-[1-benzhydryl-5-chloro-2-(hydroxymethyl)-1H-indol-3-yl]ethoxy}benzoic acid;
c) 4-{2-[1-benzhydryl-5-chloro-2-(methoxymethyl)-1H-indol-3-yl]ethoxy}benzoic acid;
d) 4-(2-{1-benzhydryl-5-chloro-2-[(phenylsulfonyl)methyl]-1H-indol-3-yl}ethoxy)benzoic acid;
e) 4-(2-{1-benzhydryl-5-chloro-2-[(methylsulfonyl)methyl]-1H-indol-3-yl}ethoxy)benzoic acid;
f) 4-[2-(1-benzhydryl-5-chloro-2-{[(2-nitrobenzyl)oxy]methyl}-1H-indol-3-yl)ethoxy]benzoic acid;
g) 4-[2-(1-benzhydryl-5-chloro-2-{[(2,6-difluorobenzyl)oxy]methyl}-1H-indol-3-yl)ethoxy]benzoic acid;
h) 4-({2-[1-benzhydryl-5-chloro-2-(hydroxymethyl)-1H-indol-3-yl]ethyl}sulfonyl)benzoic acid;
i) 4-(2-{1-benzhydryl-5-chloro-2-[(2-pyridinylmethoxy)methyl]-1H-indol-3-yl}ethoxy)benzoic acid; and
j) 4-[2-(1-benzhydryl-5-chloro-2-{[(4-fluorobenzyl)oxy]methyl}-1H-indol-3-yl)ethoxy]benzoic acid;

or a pharmaceutically acceptable salt thereof.

19. A compound of claim 1 selected from the group consisting of:

a) 4-[2-(1-benzhydryl-5-chloro-2-{[(2,4-difluorobenzyl)oxy]methyl}-1H-indol-3-yl)ethoxy]benzoic acid;
b) 4-[2-(1-benzhydryl-5-chloro-2-{[(4-cynobenzyl)oxy]methyl}-1H-indol-3-yl)ethoxy]benzoic acid;
c) 4-{2-[1-benzhydryl-5-chloro-2-({[(E)-3-phenyl-2-propenyl]oxy}methyl)-1H-indol-3-yl)ethoxy]benzoic acid;
d) 3-(4-{2-[1-benzhydryl-5-chloro-2-(hydroxymethyl)-1H-indol-3-yl]ethoxy}phenyl)propanoic acid;
e) 3-[4-({2-[1-benzhydryl-5-chloro-2-(hydroxymethyl)-1H-indol-3-yl]ethyl}sulfonyl)phenyl]propanoic acid;
f) 3-(4-{[2-(1-Benzhydryl-5-chloro-2-methyl-1H-indol-3-yl)ethyl]sulfonyl}phenyl)propanoic acid;
g) 3-(4-{[2-(1-benzhydryl-5-chloro-2-methyl-1H-indol-3-yl)ethyl]sulfanyl}phenyl)propanoic acid; and
h) 3-{4-[2-(1-Benzhydryl-5-chloro-2-methyl-1H-indol-3-yl)ethoxy]phenyl}propanoic acid;

or a pharmaceutically acceptable salt thereof.

* * * * *